United States Patent
Konopka et al.

(10) Patent No.: US 12,286,720 B2
(45) Date of Patent: *Apr. 29, 2025

(54) ELECTROCHEMICAL METHODS, DEVICES AND COMPOSITIONS

(71) Applicant: Iontra Inc, Centennial, CO (US)

(72) Inventors: Daniel A. Konopka, Denver, CO (US); Jason A. Seedig, Castle Rock, CO (US)

(73) Assignee: Iontra Inc, Centennial, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/701,522

(22) Filed: Mar. 22, 2022

(65) Prior Publication Data

US 2022/0282392 A1 Sep. 8, 2022

Related U.S. Application Data

(63) Continuation of application No. 16/897,168, filed on Jun. 9, 2020, now Pat. No. 11,280,018, which is a
(Continued)

(51) Int. Cl.
*H01M 10/44* (2006.01)
*C07D 233/58* (2006.01)
(Continued)

(52) U.S. Cl.
CPC ........... *C25D 13/18* (2013.01); *C07D 233/58* (2013.01); *C08G 69/32* (2013.01); *C25D 3/665* (2013.01);
(Continued)

(58) Field of Classification Search
CPC ............................ H01M 10/44; H02J 7/00711
(Continued)

(56) References Cited

U.S. PATENT DOCUMENTS 1,582,617 A * 4/1926 Mohn .................... C23C 18/54
  205/291
3,431,480 A * 3/1969 Wales ................... H01M 10/44
  320/139

(Continued)

FOREIGN PATENT DOCUMENTS

CA  2929515 A  5/2015
CN  1272076 A  11/2000
(Continued)

OTHER PUBLICATIONS

Couple -verb; Oxford English Dictionary, Available at https://www.oed.com/dictionary/couple_v?tab=meaning_and_use& hide-all-quotations=true#8116447 [Accessed on Jun. 27, 2024] (Year: 2024).*
(Continued)

*Primary Examiner* — Harry D Wilkins, III
(74) *Attorney, Agent, or Firm* — Gregory P. Durbin; Polsinelli PC

(57) ABSTRACT

The disclosure provides a method comprising inducing a first current between a source of a countercharge and a first electrode, the first current being through an electrolyte. A second current is induced across the first electrode, the second current being transverse to the first current, and the second current inducing a relativistic charge across the first electrode.

13 Claims, 38 Drawing Sheets

Related U.S. Application Data continuation of application No. 15/649,633, filed on Jul. 13, 2017, now Pat. No. 10,697,083.

(60) Provisional application No. 62/361,650, filed on Jul. 13, 2016.

(51) Int. Cl.

| | |
|---|---|
| *C08G 69/32* | (2006.01) |
| *C25D 3/66* | (2006.01) |
| *C25D 5/00* | (2006.01) |
| *C25D 5/18* | (2006.01) |
| *C25D 13/02* | (2006.01) |
| *C25D 13/12* | (2006.01) |
| *C25D 13/18* | (2006.01) |
| *C25D 13/22* | (2006.01) |
| *C25D 15/00* | (2006.01) |
| *C25D 17/00* | (2006.01) |
| *C25D 17/02* | (2006.01) |
| *C25D 21/12* | (2006.01) |
| *H01M 4/00* | (2006.01) |
| *H01M 10/0564* | (2010.01) |
| *C25D 3/38* | (2006.01) |
| *H01M 4/139* | (2010.01) |
| *H01M 10/0525* | (2010.01) |
| *H01M 10/06* | (2006.01) |

(52) U.S. Cl.
CPC .............. *C25D 5/18* (2013.01); *C25D 5/611* (2020.08); *C25D 5/617* (2020.08); *C25D 5/623* (2020.08); *C25D 5/67* (2020.08); *C25D 13/02* (2013.01); *C25D 13/12* (2013.01); *C25D 13/22* (2013.01); *C25D 15/00* (2013.01); *C25D 17/00* (2013.01); *C25D 17/02* (2013.01); *C25D 21/12* (2013.01); *H01M 4/00* (2013.01); *H01M 10/0564* (2013.01); *H01M 10/44* (2013.01); *C25D 3/38* (2013.01); *H01M 4/139* (2013.01); *H01M 10/0525* (2013.01); *H01M 10/06* (2013.01)

(58) Field of Classification Search
USPC ....................................................... 205/114
See application file for complete search history.

(56) References Cited

U.S. PATENT DOCUMENTS

| | | | | |
|---|---|---|---|---|
| 3,482,217 A * | 12/1969 | Finney | ............... | G11C 27/00 347/159 |
| 3,769,181 A * | 10/1973 | Biora | ............... | C25D 5/22 205/241 |
| 3,923,550 A * | 12/1975 | von Krusenstierna | | H01M 10/4214 429/229 |
| 4,159,231 A * | 6/1979 | Smith | ............... | C25B 11/054 205/333 |
| 4,608,138 A * | 8/1986 | Kobayashi | ............... | C25D 5/024 204/DIG. 9 |
| 5,039,381 A | 8/1991 | Mullarkey | | |
| 5,242,556 A * | 9/1993 | Masuzawa | ............... | B23H 3/02 204/DIG. 9 |
| 5,558,757 A * | 9/1996 | H ubel | ............... | C25D 17/10 204/229.5 |
| 5,731,101 A * | 3/1998 | Sherif | ............... | C07C 2/861 429/339 |
| 5,833,835 A * | 11/1998 | Gimaev | ............... | B23H 3/02 204/DIG. 9 |
| 5,949,213 A | 9/1999 | Lanni | | |
| 6,368,965 B1 * | 4/2002 | Lopatin | ............... | H01L 21/76877 257/E21.585 |
| 6,797,144 B2 * | 9/2004 | Su | ............... | H01L 21/76877 205/660 |
| 6,835,299 B1 * | 12/2004 | Tchugunov | ............... | B23H 7/18 205/672 |
| 6,884,335 B2 * | 4/2005 | Webb | ............... | H01L 21/2885 205/291 |
| 7,041,203 B2 * | 5/2006 | Sullivan | ............... | H01M 10/345 320/135 |
| 7,628,902 B2 * | 12/2009 | Knowlton | ............... | H01L 21/2885 205/136 |
| 7,837,841 B2 * | 11/2010 | Chen | ............... | C25D 17/001 205/104 |
| 8,048,280 B2 * | 11/2011 | Mayer | ............... | H01L 21/76877 205/186 |
| 8,182,932 B2 * | 5/2012 | Hatano | ............... | B32B 15/01 428/929 |
| 8,333,941 B1 * | 12/2012 | Atanassov | ............... | C01G 33/00 252/500 |
| 8,475,636 B2 * | 7/2013 | Mayer | ............... | C23C 18/1601 204/229.4 |
| 9,761,861 B1 | 9/2017 | Holme et al. | | |
| 2002/0025763 A1 * | 2/2002 | Lee | ............... | B24B 37/042 451/63 |
| 2002/0169516 A1 * | 11/2002 | Brussee | ............... | B23H 3/02 700/162 |
| 2003/0038036 A1 * | 2/2003 | Collins | ............... | H01L 21/76877 257/E21.585 |
| 2003/0075451 A1 * | 4/2003 | Kanda | ............... | H01L 21/2885 257/E21.175 |
| 2004/0200731 A1 * | 10/2004 | Sullivan | ............... | C25B 15/00 205/628 |
| 2005/0201176 A1 * | 9/2005 | Zangari | ............... | H01F 1/0063 |
| 2005/0261565 A1 * | 11/2005 | Lane | ............... | A61B 5/274 600/394 |
| 2006/0131175 A1 * | 6/2006 | Anton | ............... | C25D 5/18 205/104 |
| 2006/0163055 A1 * | 7/2006 | Vereecken | ............... | C25D 21/12 257/E21.175 |
| 2007/0034529 A1 * | 2/2007 | Bard | ............... | G01N 27/3277 205/334 |
| 2007/0240993 A1 * | 10/2007 | Nakato | ............... | C25D 3/56 204/229.4 |
| 2008/0018303 A1 | 1/2008 | Scheucher | | |
| 2008/0035489 A1 * | 2/2008 | Allardyce | ............... | C23C 18/1608 205/291 |
| 2008/0202922 A1 * | 8/2008 | Zhong | ............... | C25D 5/009 204/273 |
| 2008/0253922 A1 * | 10/2008 | Trimmer | ............... | C22C 19/05 420/419 |
| 2009/0301891 A1 * | 12/2009 | Locktman | ............... | C25D 17/28 205/125 |
| 2010/0122908 A1 | 5/2010 | Takeguchi | | |
| 2011/0062028 A1 | 3/2011 | Lippert et al. | | |
| 2011/0104534 A1 | 5/2011 | Wei et al. | | |
| 2011/0256807 A1 * | 10/2011 | Feng | ............... | C25F 5/00 134/1 |
| 2012/0061244 A1 * | 3/2012 | Hubel | ............... | C25D 17/002 205/640 |
| 2012/0091495 A1 * | 4/2012 | Hatanaka | ............... | H01L 33/60 205/112 |
| 2012/0126716 A1 * | 5/2012 | Hirakawa | ............... | G09G 3/22 315/246 |
| 2013/0001198 A1 * | 1/2013 | Arvin | ............... | G01N 27/403 205/83 |
| 2013/0036930 A1 * | 2/2013 | Sullivan | ............... | C25D 13/22 149/3 |
| 2013/0112564 A1 * | 5/2013 | Kleiman-Shwarsctein | ............... | C25D 7/126 205/104 |
| 2013/0137242 A1 * | 5/2013 | He | ............... | C25D 7/123 204/229.4 |
| 2013/0187724 A1 | 7/2013 | Jaakkola et al. | | |
| 2013/0220819 A1 * | 8/2013 | Hall | ............... | C25D 5/627 205/104 |
| 2014/0084849 A1 * | 3/2014 | Lee | ............... | H02J 7/00711 320/137 |

(56) References Cited

U.S. PATENT DOCUMENTS

| | | | |
|---|---|---|---|
| 2014/0144781 A1* | 5/2014 | He | C25D 17/007 204/229.4 |
| 2015/0147604 A1 | 5/2015 | Baba | |
| 2015/0171455 A1* | 6/2015 | Mills | H01M 8/0656 429/422 |
| 2016/0013462 A1 | 1/2016 | Cui et al. | |
| 2016/0261005 A1 | 9/2016 | Rustomji et al. | |
| 2016/0365600 A1 | 12/2016 | Lohmann et al. | |
| 2017/0179538 A1 | 6/2017 | Christensen et al. | |
| 2017/0179546 A1* | 6/2017 | Castaneda | H01M 10/48 |
| 2018/0010258 A1* | 1/2018 | Fujiwara | C25D 21/12 |
| 2018/0016697 A1* | 1/2018 | Konopka | C25D 15/00 |
| 2018/0019496 A1* | 1/2018 | Konopka | H01M 4/00 |
| 2019/0131622 A1* | 5/2019 | Dasgupta | H01M 4/382 |
| 2019/0221895 A1* | 7/2019 | Konopka | H02J 7/04 |

FOREIGN PATENT DOCUMENTS

| | | | | |
|---|---|---|---|---|
| CN | 101057007 | A | 10/2007 | |
| CN | 101899695 | A | 12/2010 | |
| CN | 104862750 | A | 8/2015 | |
| CN | 205152362 | U | 4/2016 | |
| EP | 0368470 | A1 | 5/1990 | |
| JP | H11111267 | A | 4/1999 | |
| JP | 2001037093 | A | 2/2001 | |
| JP | 2001-123291 | A | 5/2001 | |
| JP | 2002-362046 | A | 12/2002 | |
| JP | 2003-100790 | A | 4/2003 | |
| JP | 2009-242861 | A | 10/2009 | |
| JP | 2010-122908 | A | 6/2010 | |
| JP | 2011-066447 | A | 3/2011 | |
| JP | 2011-195898 | A | 10/2011 | |
| JP | 2012028290 | A | 2/2012 | |
| JP | 2012069319 | A | 4/2012 | |
| JP | 2017099164 | A | 6/2017 | |
| KR | 20010033089 | A | 4/2001 | |
| KR | 20120008891 | A | 2/2012 | |
| WO | 2009060248 | A2 | 5/2009 | |
| WO | WO 2015/164592 A1 * | | 10/2015 | H01M 10/44 |
| WO | WO-2017184482 A1 * | | 10/2017 | H01M 10/052 |
| WO | WO-2019140401 A1 * | | 7/2019 | H01M 10/052 |

OTHER PUBLICATIONS

Coupling; Oxford English Dictionary, Available at https://www.oed.com/dictionary/coupling_n?tab=meaning_and_use& hide-all-quotations=true#8119062 [Accessed on Jun. 27, 2024] (Year: 2024).*

Kovac, Z., The Effect of Superimposed A.C. on D.C. in Electrodeposition of Ni - Fe Alloys, Journal of The Electrochemical Society, 118(1): 51-57, 1971 (8 pages).

Park, J., et al. "Micro-Patterned Lithium Metal Anodes with Suppressed Dendrite Formation for Post Lithium-Ion Batteries", Advanced Materials Interfaces, 2016; vol. 3, No. 11,https://doi.org/10.1002/admi.201600140, 9 pages.

Ryou, M.H., et al., "Mechanical surface modification of lithium metal: Towards improved Li metal anode performance by directed Li plating", Advanced Functional Materials, 25(6), 834-841. https://doi.org/10.1002/adfm.201402953, 8 pages.

Lacressonniere, F., et al. "Influence of a charging current with a sinusoidal perturbation on the performance of a lead-acid battery", IEEE Xplore, Oct. 2005, 152(5): 1365-1370, DOI: 10.1049/ip-epa:20050008, 6 pages.

International Search Report and Written Opinion mailed May 5, 2019 in PCT/US2019/013533 (Agent's File Reference No. 076157-614810), 16 pages.

* cited by examiner

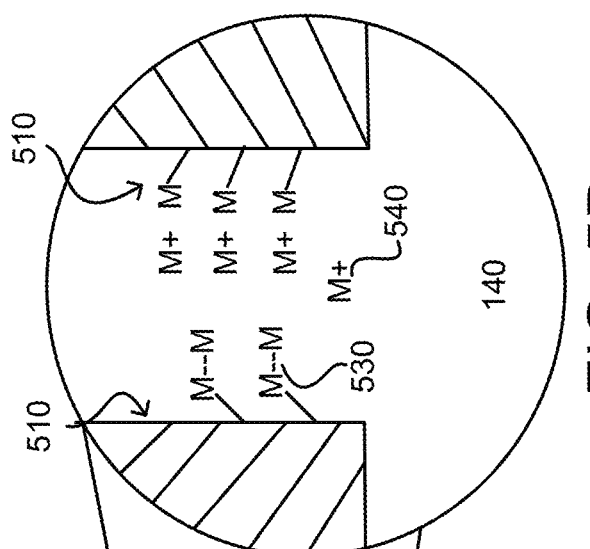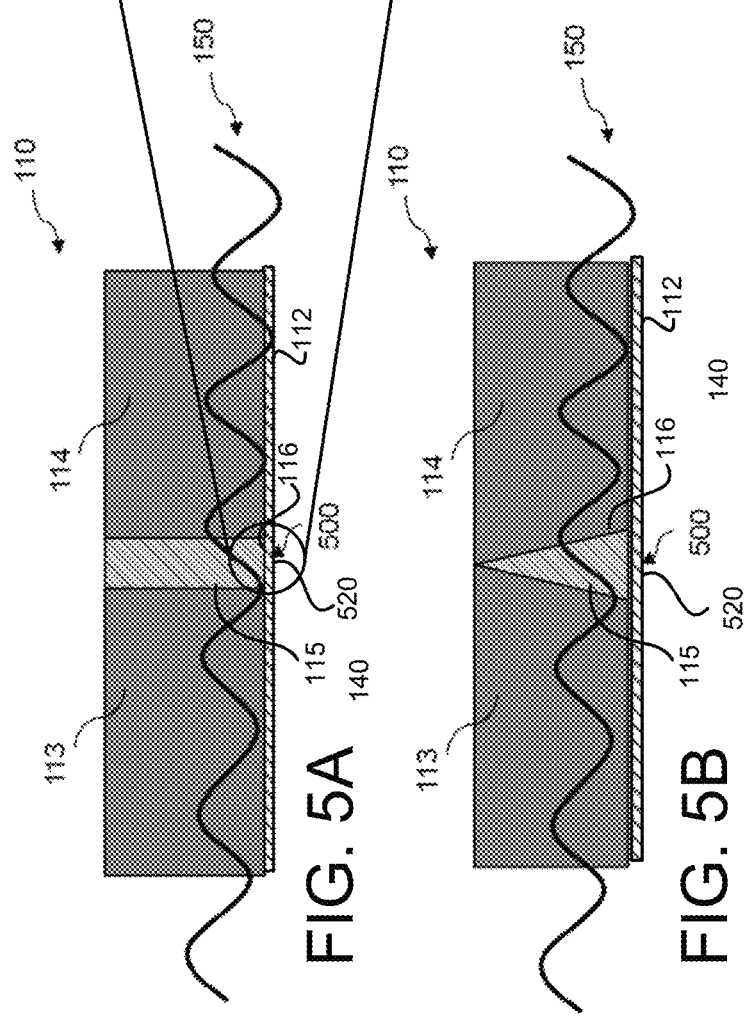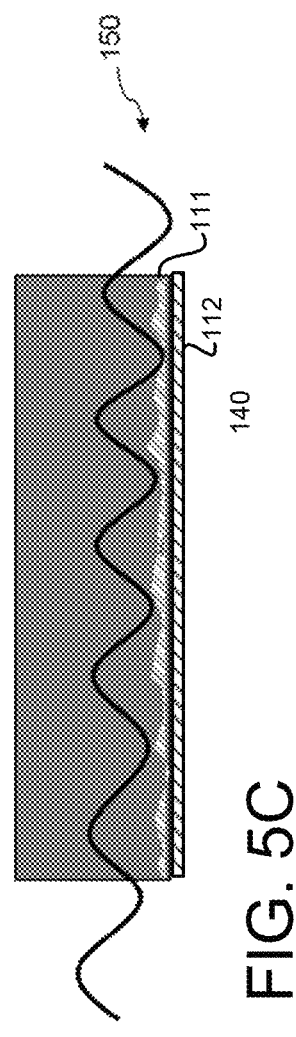

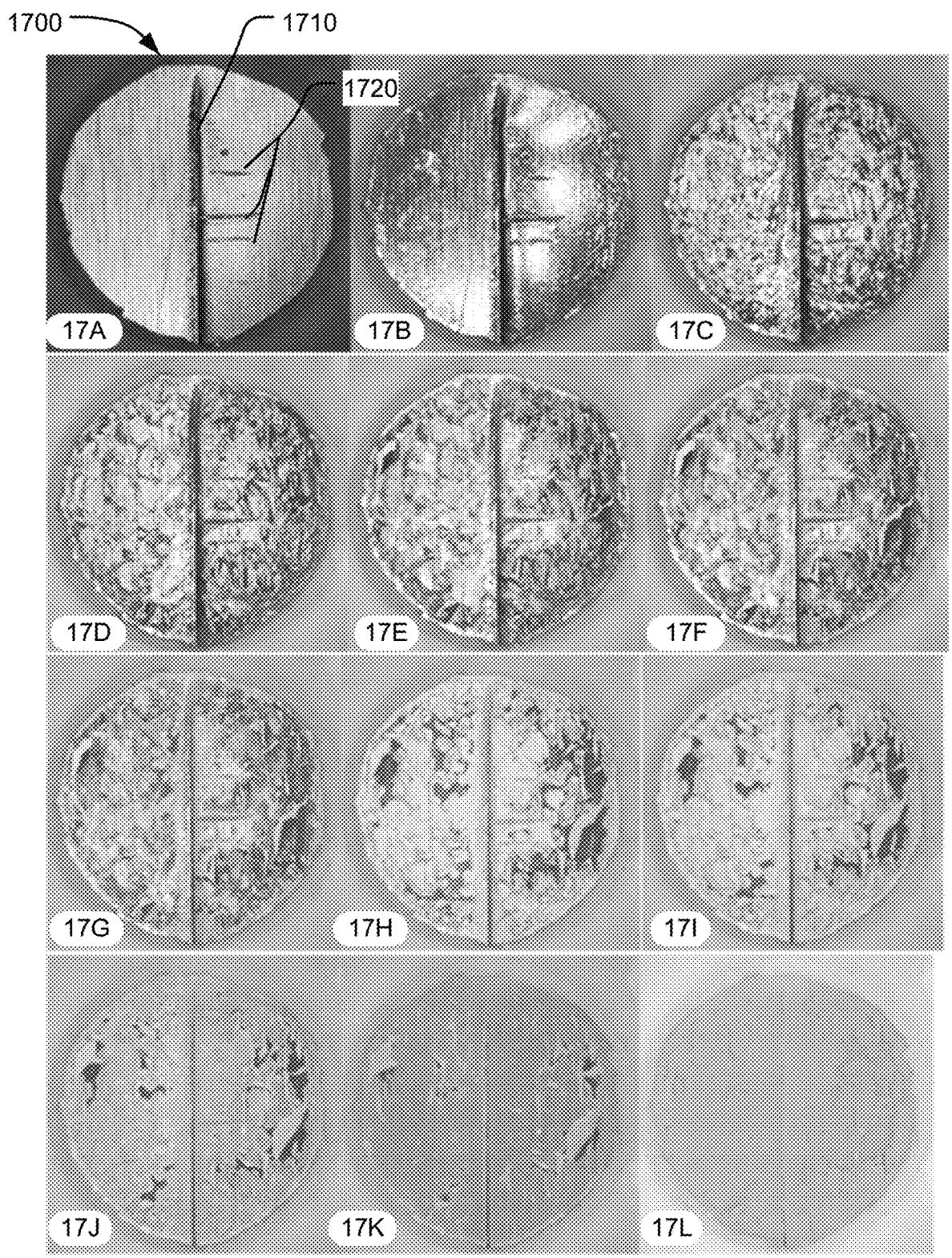
FIGS. 17A-L

ELECTROCHEMICAL METHODS, DEVICES AND COMPOSITIONS

CROSS-REFERENCE TO RELATED APPLICATIONS

The present application is a continuation of U.S. Nonprovisional application Ser. No. 16/897,168 filed Jun. 9, 2020 entitled "Electrochemical Methods, Devices and Compositions," which is a continuation of U.S. Nonprovisional application Ser. No. 15/649,633 filed Jul. 13, 2017 entitled "Electrochemical Methods, Devices and Compositions," now U.S. Pat. No. 10,697,083, which claims priority to U.S. Provisional Application No. 62/361,650 filed Jul. 13, 2016 entitled "Electrochemical Methods, Devices and Compositions," both of which are hereby incorporated by reference in their entirety.

The present continuation application is related to U.S. Nonprovisional application Ser. No. 15/649,569 filed Jul. 13, 2017 entitled "Electrochemical Methods, Devices and Compositions," now U.S. Pat. No. 10,480,094, which also claims priority to U.S. Provisional Application No. 62/361,650 filed Jul. 13, 2016 entitled "Electrochemical Methods, Devices and Compositions," both of which are hereby incorporated by reference in their entirety.

TECHNICAL FIELD

Aspects of the present disclosure involve electrochemistry, and particularly materials bonding, surface repair, electroplating, corrosion and electrocatalysis.

BACKGROUND

Traditional material fusion techniques, such as welding, have serious limitations. For example, often fusion techniques cannot be applied to materials with heat or electricity constraints. In one specific example, support beams are vulnerable to warping and possible failure when heated to temperatures needed for traditional welding. In another example, objects near sensitive electronics and volatile chemicals cannot be fused, re-fused or restored by conventional means (smelting, brazing, and welding) until separated from such sensitive equipment or materials. These methods also cannot be used on metallic materials which require contiguous, uniform properties.

Welding is a common method for fusing together metal pieces by heating the surfaces to the point of melting using a blowtorch, electric arc, or other means, and uniting the metal pieces by pressing, hammering, or the like. Metals tend to be either machinable or weldable, which poses a widespread challenge in the manufacturing industry. For example, many advanced alloys are machinable, but conventional welding would alter their precise grain structures and destroy the properties of the alloy. Welded and heat-treated joints experience changes to their material properties with consequences to stress and strain distribution, heat conduction, static dissipation, etc. As such, the conventional welding is not compatible with all industrially relevant metals.

Alternatively, electrodeposition is a process for coating a thin layer of one metal on top of a substrate, often to modify its surface properties. Although electrodeposition does not require the high temperatures of welding for melting metal surface, the thin layers of metal obtained from electrodeposition cannot join and unite metal pieces in a mechanically strong or durable way.

It is with these issues in mind, among others, that aspects of the present disclosure were conceived.

SUMMARY

The following embodiments and aspects thereof are described and illustrated with systems, tools and methods meant to be exemplary and illustrative, not limiting in scope. In various embodiments, one or more of the above-described problems have been reduced or eliminated, while other embodiments are directed to other improvements.

Provided herein is a method comprising inducing a first current between a source of a countercharge and a first electrode, the first current being through an electrolyte. A second current is induced across the first electrode. The second current is transverse to the first current, and the second current inducing a relativistic charge across the first electrode. The method may further comprise applying a signal cancellation to reduce a far-field radiation from the first electrode.

The present disclosure also provides a method comprising inducing an electric field between a source of a countercharge and a first electrode, the electric field having field lines through an electrolyte. A potential is induced across a surface of the first electrode. The induced potential bends the field lines proximate the surface such that metal from the electrolyte follows a path of the bent field lines to deposit the metal onto the surface.

The present disclosure further provides a method comprising inducing a potential across a surface of an electrode in the presence of a chemical potential between an electrolyte and the surface of the electrode. The induced potential relativistically charges the surface of the electrode.

The present disclosure provides a corroding electrode comprising one or more metal species selected from the group consisting of metal particles, metal ions, and combinations thereof. The corroding electrode dissolves when a first current is applied between the corroding electrode and a first electrode through an electrolyte, thereby suspending the one or more metal species into the electrolyte.

Provided herein is a device comprising a source of a countercharge, and a first electrode in electrical communication through an electrolyte with the source of a countercharge; wherein a first current is induced through the electrolyte between the source of a countercharge and the first electrode; and wherein a second current is induced across the first electrode, the second current being transverse to the first current, and the second current inducing a relativistic charge across the first electrode.

The present disclosure may also provide a device comprising a source of a countercharge, and a first electrode in electrical communication through an electrolyte with the source of a countercharge. An electric field is induced between the source of a countercharge and the first electrode. The electric field has field lines through the electrolyte. A potential is induced across a surface of the first electrode. The induced potential bends the field lines proximate the surface such that metal from the electrolyte follows a path of the bent field lines to deposit the metal onto the surface.

The present disclosure provides an electrode, wherein a potential is induced across a surface of the electrode in the presence of a chemical potential between an electrolyte and the surface of the electrode. The induced potential relativistically charges the surface of the electrode. This electrode may be a first electrode in any method or device described herein.

The present disclosure further provides a device comprising a main control unit comprising a power supply and a power modulator; an electrode applicator unit, comprising at least one source of a countercharge and a plurality of channels for flowing an electrolyte through the electrode applicator unit, the electrode applicator unit being connected to the main control unit; a current collector cable connected to the main control unit; and a power control unit connected to the main control unit. The power control unit applies a first current between a first electrode and the at least one source of a countercharge through the electrolyte, the power control unit inducing a second current across the first electrode, the second current being transverse to the first current, and the second current inducing a relativistic charge across the first electrode.

The present disclosure provides an apparatus, comprising: a source of countercharge; an electrode; an electrolyte in contact with the electrode and through which a first current between the source of countercharge and electrode flows; and a waveform generating device coupled with the electrode, the waveform generating device inducing an electric waveform across the electrode in the presence of the current.

The present disclosure provides a method, comprising applying a first current between a source of countercharge and an electrode; and applying an electric waveform across the electrode, the electric waveform having an energy density greater than 0 mA/cm$^2$ and less than 300 mA/cm$^2$ and a frequency between 35 kHz and 10 GHz.

Additional embodiments and features are set forth in part in the description that follows, and in part will become apparent to those skilled in the art upon examination of the specification, or may be learned by the practice of the embodiments discussed herein. A further understanding of certain embodiments may be realized by reference to the remaining portions of the specification and the drawings, which forms a part of this disclosure.

BRIEF DESCRIPTION OF THE DRAWINGS

Example embodiments are illustrated in referenced figures of the drawings. It is intended that the embodiments and figures disclosed are to be illustrative rather than limiting.

FIGS. 5A-5D depict several first electrodes with features filled by operation of the methods described herein. In FIG. 5A, a second current 150 transverse a first electrode 110 having a void 500 between a first portion 113 and a second portion 114. The second current 150 produces a relativistic charge 112 on the first electrode 110, whereby metal is bonded to a first edge 115 and a second edge 116 to fill a gap 520 in the void 500. FIG. 5B depicts a process similar to FIG. 5A, where the void 500 is a high-aspect ratio feature in the first electrode 110. In FIG. 5C, a rough surface 111 of the first electrode 110 is filled. FIG. 5D is an inset of FIG. 5A showing the formation of a new metal-metal bond 530 between a metal 540 in the electrolyte 140, and a metal edge 510 of the first edge 115 in the void 500.

FIG. 6A shows the process without a second current 150; that is, a conventional electrodeposition. FIG. 6B shows application of a second current 150, without a DC offset on non-uniform surfaces. FIG. 6C shows the angles 151, 152, 153 of the second current 150 relative to the void 500. Arrows 611, 612, 613 indicate directions of induced growth.

FIG. 14B was conducted under a second current having a waveform of 5 MHz, 10 Vpp sinusoidal.

FIGS. 17A-17L depict an electrochemical corrosion followed by crack-filling and planar surface deposition. FIG. 17A shows the electrode 1700 with a surface having a cut 1710 and horizontal indentations 1720. FIGS. 17B and 17C show electrochemical corrosion and roughening. FIGS. 17D-17L show the result of an electrochemical process using a second current, providing in smooth, planar surface.

FIG. 18A shows the sample at ×200 magnification and FIG. 18B shows the same sample at ×2000 magnification.

FIG. 19B is a microscopic view of the surface at ×800 magnification. Lighter areas at 10 μm Cu powder, darker areas are $CuSO_4$. Pellet pressed at 80 kpsi for 30 min.

FIG. 38A shows the elements present. FIG. 38B was a composite of the iron, aluminum, and carbon signals, showing the codeposition of aluminum and iron at the surface of the steel substrate. FIGS. 38C-E are the two-dimensional elemental maps for iron, aluminum, and carbon, respectively.

FIG. 39A is a scanning electron micrograph of the sample. FIGS. 39B and 39C are the two-dimensional elemental maps for aluminum and iron in the sample, respectively. FIG. 39D shows the elements present in the sample.

FIG. 40H shows an electron micrograph composite of the electron micrograph (FIG. 40A), and the two-dimensional elemental contents for iron (FIG. 40B), zinc (FIG. 40C), carbon (FIG. 40D), chlorine (FIG. 40E), and oxygen (FIG. 40F), showing the codeposition of zinc and iron to form the alloy. FIG. 40G shows the elemental distribution in the sample.

FIGS. 44A & 44B show copper sheets joined with the transverse current parallel to the junction. FIGS. 44C & 44D show copper sheets joined with transverse current perpendicular to the junction. Here, a shiny finish was obtained, but the junction displayed greater bending fatigue. FIG. 44E shows a sample deposited without the transverse current as close to the junction and with a 5-V DC offset, which displayed good strength and a rough finish.

DETAILED DESCRIPTION

Figure 1:
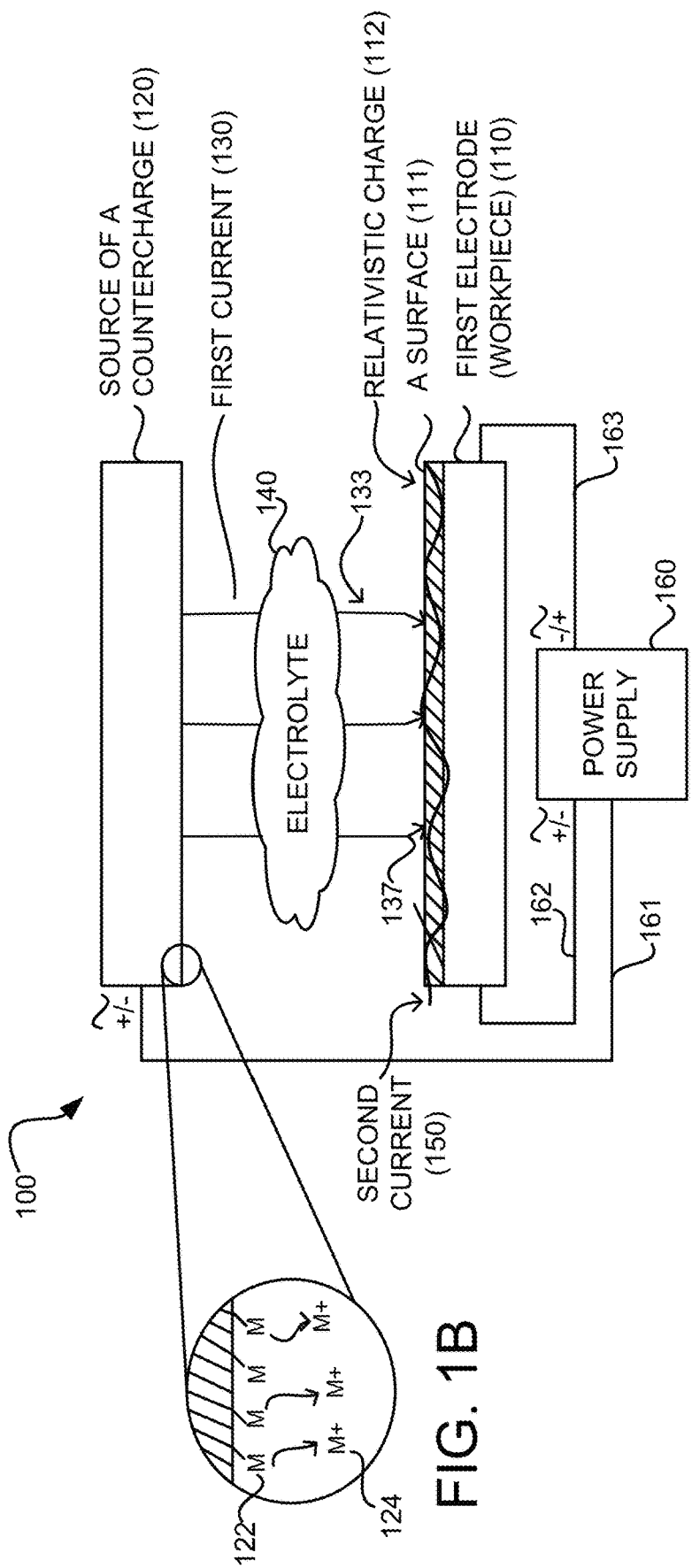
FIG. 1A depicts a device 100 comprising a source of a countercharge 120, and a first electrode 110 in electrical communication with the source of a countercharge 120 through an electrolyte 140. A first current 130 is induced through the electrolyte 140 between the source of a countercharge 120 and the first electrode 110. A second current 150 is induced across the first electrode 110, the second current 150 being transverse to the first current 130, and the second current 150 inducing a relativistic charge 112 across a surface 111 of the first electrode 110. The device also comprises a power supply 160 in electrical communication 161 with the source for a countercharge 120 and in electrical communication 162, 163 with the first electrode 110.
FIG. 1B is an inset of FIG. 1A, showing an embodiment where the source of countercharge 120 is a corroding electrode. When the first current 130 is induced between the corroding electrode 120 and the first electrode 110 through the electrolyte 140, metal 122 from the corroding electrode 120 is released as metal species (M+) 124 into the electrolyte 140.

Provided herein are methods, devices and compositions which electrochemically bond or rearrange metals on surfaces. Generally, the methods and devices operate by inducing a first current between a source of a countercharge and a first electrode through an electrolyte. The electrolyte is adjacent to the surface of the first electrode, forming an electrode-electrolyte interface, where metal from the electrolyte contacts the surface of the first electrode to form new metal-metal bonds during the electrochemical process.

The first electrode may be the workpiece where new metal-metal bonds are formed between metal on the surface and metal from the electrolyte, and is typically charged as a cathode. When a second, transverse current is induced across the first electrode, electrons at the surface of the experience a forward compression and rearward expansion of their electric field. This compression and expansion generates a relativistic charge propagating outward from the electron's center at the speed of light. The relativistic charge then bends the field lines of the first current, directing metal from the electrolyte to form new metal-metal bonds in cracks and crevices, pits and voids, and high-aspect surface features on the workpiece.

In contrast, in the example of a metal component with a crack conventional electrodeposition covers the top surface of the component and domes over the crack, entombing a permanent crack. The method described herein, distinctly, fills in the gap and eliminates the crack, producing a flat joint and a workpiece with a flat backside. Moreover, metal at the boundaries of the crack may be bonded to metal from the electrolyte in a mechanically robust way. In another embodiment, the methods disclosed herein fill in a through-hole drilled into a workpiece, eliminating many steps from any suitable conventional process. In other embodiments, the metal may be electroformed onto a negative mold. Conventionally, problems arise at the boundaries between molded segments. The method disclosed here joins these molded segments with mechanically strong bonds.

The opposite effect may be attained by selecting the appropriate transverse current, deterring filing effects. For example, a current may be selected to prevent material from entering a gap in the workpiece, much as a current may be selected to corrode a region of a workpiece to roughen it for better adhesion in deposition.

The methods and devices described may operate by inducing an electric field between a source of a countercharge and a first electrode where the electric field is through the electrolyte. The first electrode may be workpiece on which or to which some operation, such as depositing material, bonding, polishing, plating, or corrosion being performed, according to the techniques discussed.

An electric potential is induced across a surface of the first electrode. The induced potential bends the field lines proximate the surface so metal from the electrolyte follows a path of the bent field lines to deposit the metal onto the surface. In one specific example, the induced potential affects the field lines. These bent field lines ultimately intersect the surface, including irregularities in the surface, at 90 degrees to the portion of the surface being intersected. Viewed another way, the bent field lines of the first current alter the trajectory of the metal from the electrolyte as it deposits onto and is bonded to the surface, so the metal has a lower probability of reaching the overall surface at 90° on its approach, but rather conforms to the contours, irregularities, and exhibits a leveling behavior on the surface.

The induced potential of the transverse current can be controlled by tuning the waveform, including its voltage, amperage and frequency. Multiple waveforms can even be combined to tune into different features or substances comprising the surface of the workpiece. The extent of metal bonding can be monitored in real-time, so the transverse current and first current can be modulated to continue metal bonding, electropolishing, or other electrochemical processes on the workpiece. This electrochemical process can also be run in reverse, where corrosion of the workpiece sends metal species into the electrolyte. From either embodiment, the present methods and devices represent a radical departure from conventional metal fusing techniques or previously known electrodeposition methods.

Specifically, conventional metal joining techniques use an adhesive with material properties different from those of the substrate. Sometimes sheet metal is joined by using advanced glues combined with crimping or rivets for strength, but these methods are limited to thin substrates. Fusion techniques such as welding use large amounts of power for heat and/or pressure to melt metal at junctions.

The welding techniques are cumbersome and dangerous. Many resistance welding processes require an inert shielding gas to remove oxygen from the weld area. Gas compression is very inefficient and energy intensive, accounting for up to 10% of industrial electricity consumption. To avoid overheating, welding is limited to a single spot or multiple spots only if sufficiently spaced. Resistance welding also involves intense UV radiation, deadly voltages and currents, toxic fumes, noise, and flammability concerns.

Welding has severe limitations to which metals to which it can be applied. Welding dissimilar metals, even different grades of alloy having the same base metal, results in cracking and poor adhesion at the joint. Many grades of common metals are non-weldable because of small concentrations of other elements which respond differently to intense heat, such as aircraft grade aluminum (7075-T6), which contains ~10% of other elements including Zn and Cu.

Figures 6A, 6B:
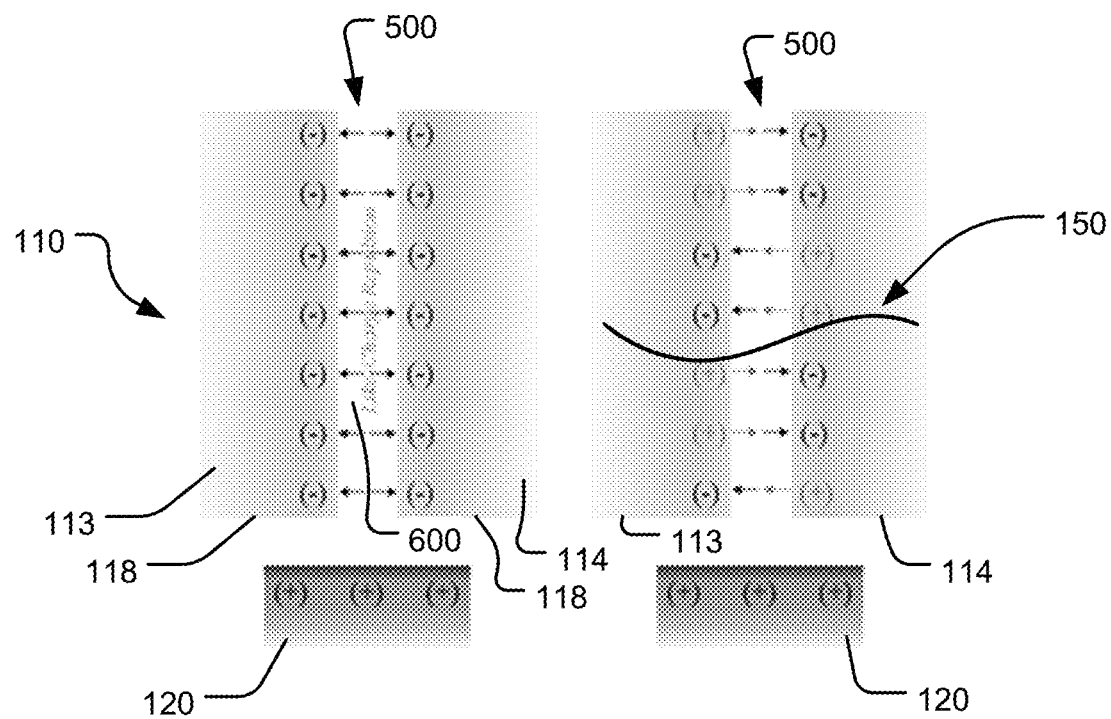
FIGS. 6A-6C depict an electric field 600 inside a void 500 between two portions 113, 114 of the first electrode 110.

Conventional electrodeposition may be used where welding fails, but not without its own limitations. Conventional electrodeposition does not form mechanically strong bonds between adjacent workpieces, due to metal surface tension, contact resistance, and stored stress resistance (e.g. as shown at FIG. 6A). Conventional electrodeposition also employs large, typically aqueous, baths of plating solution and direct current applied between an anode and a workpiece—an immersed, conductive cathode to be metal-plated. Plating baths must be of very large volume (hundreds of gallons) for even small workpieces to maintain homogenous reactant concentrations, adequate spacing between the anode and workpiece, and complete peripheral anodic boundaries around the plated object to ensure a uniform electric field, and uniform plating on all sides of the object.

As conventional deposition occurs, the concentration of dissolved metal species decreases approaching the electrode surface. Areas like trenches and voids do not experience as much convection. They have lower reactant concentrations and slower deposition rates compared to open surfaces. When this happens, like-charge repulsion increases. So long as positive metal ions are abundant in solution to neutralize two adjacent negatively-charged edges, metal depositing at each edge may grow toward one another, even to electrical contact. However, the growth of the two edges into each other does not form a bond between them. They may grow until the original surfaces abut each other, but the original gaps still exists as a weak fracture that prevents mechanical resilience.

If the concentration of metal ions drops, the negative charges of each edge are not neutralized and the two edges are repulsed from each other. With rough deposits, contact is poor, so edges are rough when they initially come into electric contact. The total contact area is low. This geometry contributes to contact resistance between metal edges that grow together and presents an energy barrier to forming strong mechanical contact. The energy to overcome the different stresses stored in each edge also increase.

During conventional electroplating, disproportionately more material deposits onto areas of curvature than on planar surfaces. A smooth, even finish is usually desired, so chemical and engineering controls must be built into electroplating processes to reduce this effect. Controls usually involve running the plating process at reduced current densities, using multiple, distributed anodes to shift the electric field density, and using organic additives.

For conventional electrodeposition and plating, surfaces must be preprocessed to achieve favorable outcomes. Acid strikes and polishing clean workpiece surfaces and remove native oxides that would otherwise prevent newly deposited material from bonding. Low current densities are used to avoid rough deposits. These steps represent a significant portion of the chemical resources and time in conventional electroplating and deposition.

The present disclosure may be understood by reference to this detailed description, taken with the drawings as described above. It is noted that, for illustrative clarity, certain elements in various drawings may not be drawn to scale, may be represented schematically or conceptually, or otherwise may not correspond exactly to certain physical configurations of embodiments.

I. Method

Figure 3:
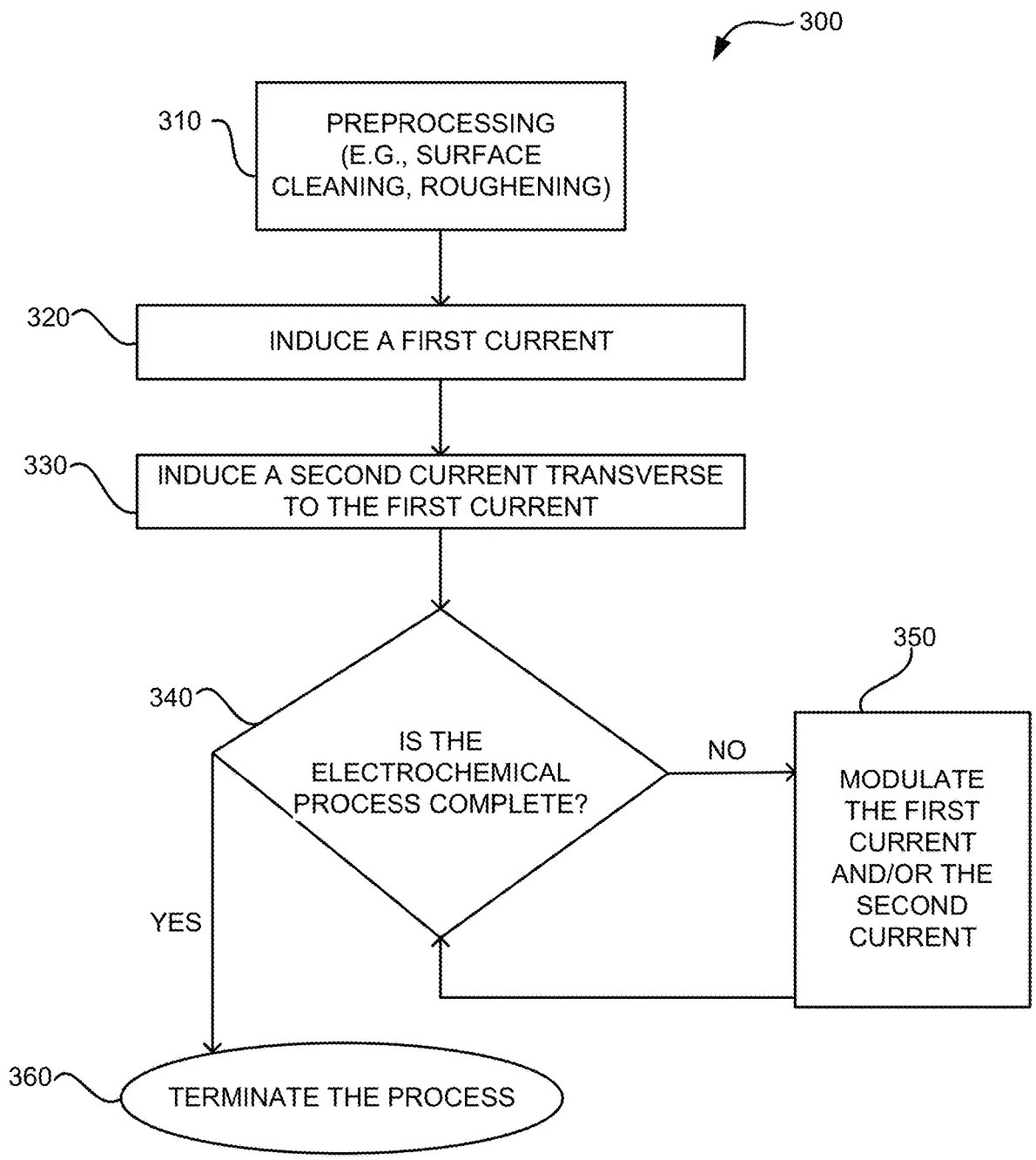
FIG. 3 is a flowchart of the methods described. The workpiece may be preprocessed (e.g., surface cleaning, roughening, etc.) (310), before inducing a first current (320) and inducing a second current (330). If the electrochemical process is incomplete (340), the first current and/or the second current may be modulated (350). If the electrochemical process is complete (340), the process terminates (350).

In view of the introduction, as well as issues and limitations relative to conventional processes, provided herein are electrochemical apparatus and methods for depositing and rearranging metals on surfaces. FIG. 1 illustrates an example device for practicing the method discussed herein. FIG. 3 illustrates an example method according to the present disclosure. Referring to FIGS. 1 and 3, a workpiece 110 may be preprocessed (e.g., surface cleaning, roughening, etc.) (310), before inducing a first current (320) and inducing a second current (330), which may be an alternating or non-DC current across the workpiece. If the electrochemical process is incomplete (340), the first current and/or the second current may be modulated (350). If the electrochemical process is complete (340), the process terminates (360). The completeness of a reaction can be assessed by any method known to one of skill in the art, including spectrometry and microscopy, as well as methods newly disclosed herein, which monitor deposition in real-time.

Referring in more detail to FIG. 1, the device 100 involves a source of a countercharge 120, and a first electrode 110 (which may be the workpiece) in electrical communication with the source of a countercharge 120 through an electrolyte 140. A first current 130 is induced through the electrolyte 140 between the source of a countercharge 120 and the first electrode 110. A second current 150 is induced across the first electrode 110, the second current 150 being transverse to the first current 130, and the second current 150 inducing a relativistic charge 112 across a surface 111 of the first electrode 110. In some embodiments, the device includes a power supply 161 in electrical communication 161 with the source for a countercharge 120 and in electrical communication 162, 163 with the first electrode 110. The power supply, which may involve more than one physical power supplier, may provide and control the first current 130 and the second current 150.

Figure 2:
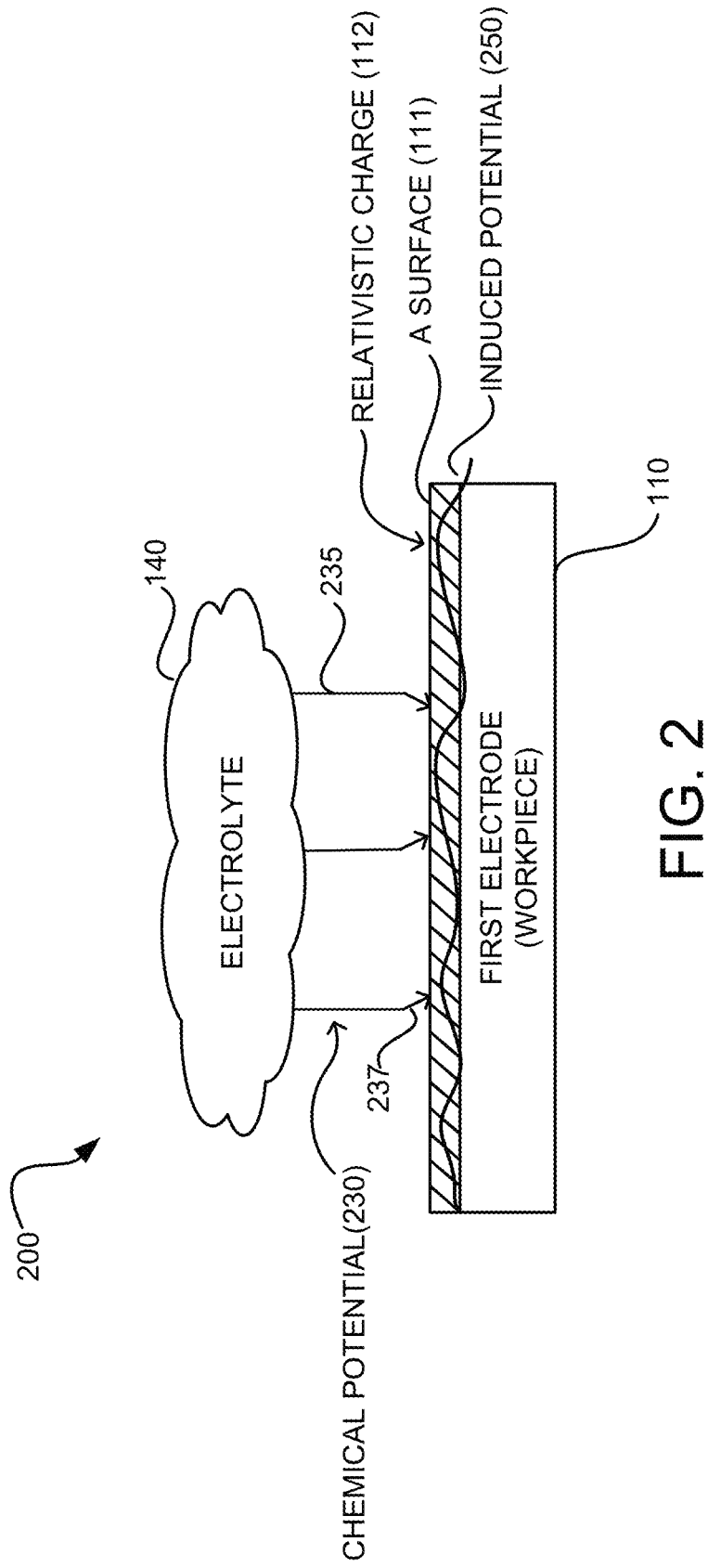
FIG. 2 depicts a first electrode 110, wherein a potential 250 is induced across a surface 111 of the first electrode 110 in the presence of a chemical potential 230 between an electrolyte 140 and the surface 111 of the first electrode 110. The induced potential 250 relativistically charges 112 the surface 111 of the first electrode 110.

Alternatively, the methods according to this disclosure may be contemplated in a device according to FIG. 2. In this embodiment, a first electrode 110 has a potential 250 induced across its surface 111 in the presence of a chemical potential 230 between an electrolyte 140 and the surface 111. The induced potential 250 relativistically charges 112 the surface 111 of the first electrode 110. The induced potential bends the field lines proximate the surface such that metal from the electrolyte follows a path of the bent field lines to deposit and bond the metal onto the material surface.

A. First Electrode (e.g., Workpiece)

The first electrode, in many possible examples discussed, may also be the workpiece, or workpieces, or the cathode in an electrochemical process. The first electrode may include more than one discrete piece, for example, when one is joining or bonding separate metal pieces.

At the first electrode, negative charge is isolated at a surface nearest the electrolyte, while positive charge is pushed to the first electrode's farthest surfaces. The first electrode is polarized with negative and positive charges when a current (for example, a first current or a transverse current) is applied, or when an electric or chemical potential is induced across the first electrode. The methods according to this disclosure manipulate electron density on the workpiece to guide metal deposition, and the like.

Figure 4A:
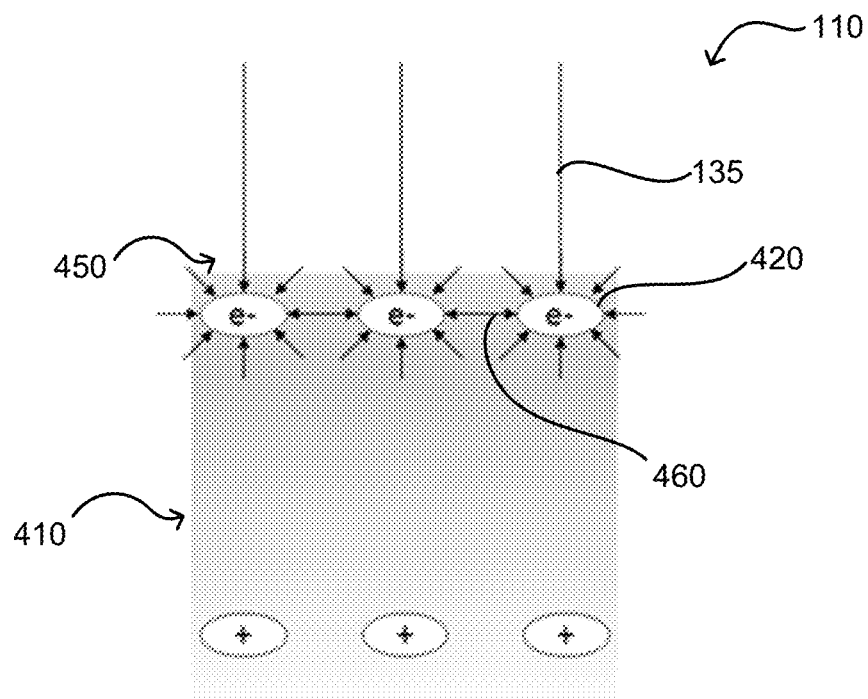
FIG. 4A depicts capacitive charge separation 410 in a first electrode 110. Electric field lines 135 are represented by black arrows pointing toward negative charges (electrons, 420).
Figure 4B:
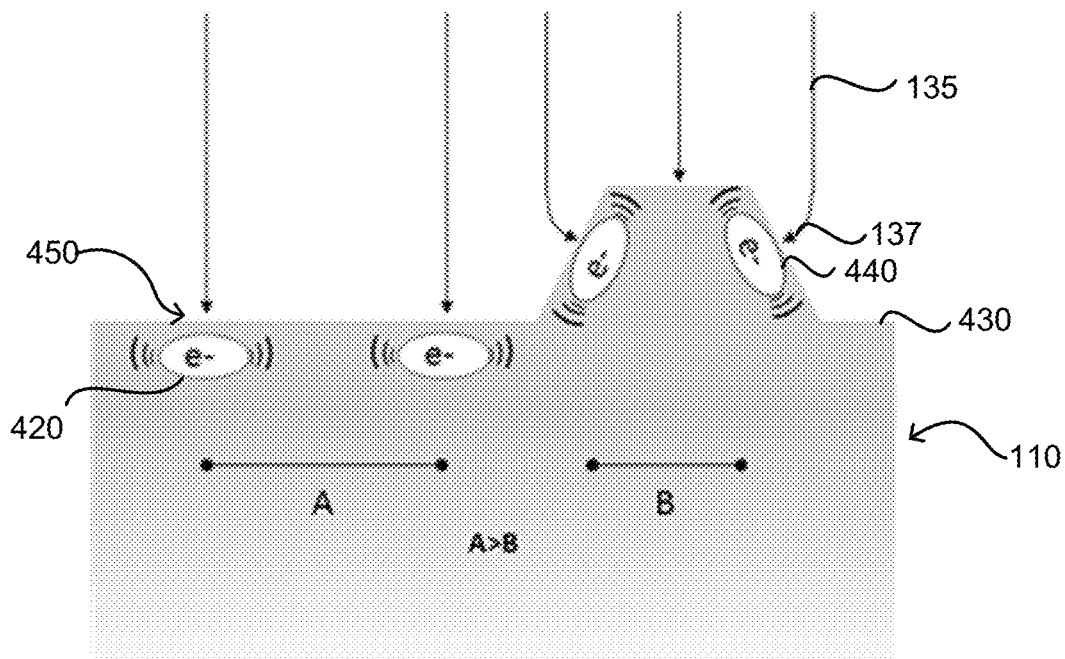
FIG. 4B depicts electron distribution 450 among the electrons 420 on smooth areas 430 and rough areas 440 of the surface 111 of the first electrode 110.

The charge density of a polarized workpiece absent the influence of a second current can be understood referring to FIGS. 4A and 4B, which illustrate the effects of smoothness and roughness on the substrate. Negatively charged sides 440 have a higher density of electrons 420, which distribute themselves evenly across the surface 111, due to the equal repulsion 460 of their individual electric fields. This repulsion effect 460 occurs parallel to the tangential point of an electron's position at a surface 111. So smooth surfaces 430 experience the most uniform charge distribution (FIG. 4A), whereas any curvature, such as a rough topography, increases charge density (FIG. 4B). As curvature 440 increases, the repulsive forces of local electrons are less in-plane, allowing closer proximity (FIG. 4B).

Continuing to reference FIGS. 4A and 4B, the electric field lines 135 may originate at the source for a countercharge 120 and terminate at the negatively charged surface 111 of the first electrode 110. The surface 111 becomes negatively charged under operation of a current or an induced potential. Electrons 420 have an electric field in all directions (FIG. 4A), while electron-electron repulsion 460 occurs parallel to the surface 111 (FIG. 4B). Due to electron distribution 450, electric field lines 135 terminate perpendicular to a tangent of the surface 111 and deviate from their original vector (137) to maintain this behavior at curves 440. The increased charge density at non-planar areas of the first electrode results in greater electrochemical activity relative to smooth areas. The distance A between electrons 420 in smooth regions 430 is greater than the distance B between electrons 420 in rugged regions 440.

The workpiece may have voids and gaps, which affect the electron distribution at the surface. Referring now to FIGS. 5A, 5B and 5D, the first electrode 110 may have a void 500 with a metal edge 510. The relativistic charge 112 may cause a metal-metal bond 530 to form between metal 540 from the electrolyte 140 and the metal edge 510 to fill the void 500. In various aspects, the void 500 may be a crack, crevice, or fracture in the first electrode. The void 500, of FIG. 5A is in the form of a gap 520 between a first portion 113 of the first electrode 110, the first portion 113 having a first edge 115 of the metal edge 510, and a second portion 114 of the first electrode 110, the second portion 114 with a second edge 116 of the metal edge 510 proximate the first edge 114. The relativistic charge 112 may cause the metal-metal bond 530 to form between metal from the first edge 114 and metal 540 from the electrolyte 140 and between metal from the second edge 116 and metal 540 from the electrolyte 140. The bonded metals bridge the gap 520 to form a unified electrode of the first portion 114 and the second portion.

FIG. 5B depicts a process similar to FIG. 5A, where the void 500 is a high-aspect ratio feature in the first electrode 110. The void 500 here also forms a gap 520 between a first portion 113 of the first electrode 110, the first portion 113 having a first edge 115 of the metal edge 510, and a second portion 114 of the first electrode 110, the second portion 114 with a second edge 116 of the metal edge 510 proximate the first edge 115. The relativistic charge 112 causes the metal-metal bond 530 (as shown in FIG. 5D) to form between metal from the first edge 115 and metal 540 from the electrolyte 140 and between metal from the second edge 116 and metal 540 from the electrolyte 140. The bonded metals bridge the gap 520, with methods at the closing gap bonding, to form a unified electrode of the first portion 113 and the second portion 114, and metals bonded within and across the gap.

In FIG. 5C, a rough surface 111 of the first electrode 110 may be filled with metal bonded from the electrolyte. The relativistic charge 112 causes the metal-metal bond 530 to form between metal from the surface 111 and metal 540 from the electrolyte 140. A chemical potential exists between the electrolyte and the surface of the workpiece. In this context, a transverse current without applying a first current could drive some deposition, although the combination of a first current with the transverse current is more effective at depositing more metal than is lost to dissolution or corrosion.

The electrostatic environment of the voids described above can be understood with reference to FIG. 6A, illustrating a conventional electrodeposition process applied to the structure of FIG. 5A in contrast to FIG. 6B, illustrating a process as described herein applied to the structure of FIG. 5A. Referring first to FIG. 6A, absent a second current 150, as in a conventional electrodeposition, void 500 within the first electrode 110 would have like charges and experience repulsion 600. This interaction results in contact and stored stress resistance, which make strong bonding energetically unfavorable, such that metal from the electrolyte would not readily find its way into the void 500 (FIG. 6A). While metal deposition may occur still inside the void 500, it would be slow compared to growth atop the surfaces 118, 119 closest the source of a countercharge 120.

In contrast, now referring to FIG. 6A, using a method according to the present disclosure, a second current 150 flowing from a first portion 113 to a second portion 114, across the first electrode 110 induces a planar electric field in the void 500. The induced potential can be targeted across the area being treated or bonded; the potential need not be induced across the entire workpiece. This electric field of the second current 150 transverses the first current. Depositing metal species are redirected by the second current 150 and fill the junction 500 instead of immediately depositing on the surfaces 118, 119 of the first electrode 110 nearest to the source of a countercharge 120.

Figure 6C:
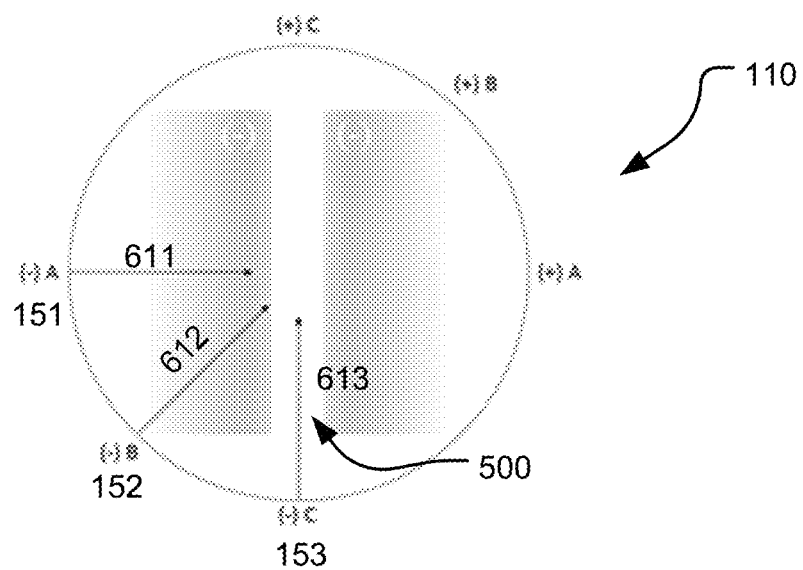

FIG. 6C illustrates possible angles 151, 152, 153 which the second current 150 could be applied relative to the void 500. Arrows 611, 612, 613 indicate directions of induced growth. Angle 151 and arrow 611 would only modulate the electrodeposition current and do not display the disclosed effects related to treatment with a transverse current. Angle 152 and arrow 612 would promote some additional growth within the gap compared to a conventional electrodeposition, but not as much as angle 153 and arrow 613, which squarely targets growth within void 500. In practice, applying and propagating a second current is complex. The results depend on more than just the angle, but also on frequency, power, and other characteristics of the second current.

B. Electrolyte

The methods and devices described herein use an electrolyte. Generally, the electrolyte comprises a metal, which is a source for new material deposited and bonded at the first electrode. In particular, the electrolyte may comprise a metal and one or more species selected from the group consisting of water, ammonium salts, metal chlorides, metal sulfates, ionic liquids, ionogels, and any combination thereof. When the electrolyte comprises an ammonium salt, the ammonium salt may be a tertiary ammonium salt, a quaternary ammonium salt, or combinations thereof.

1. Solvent

Generally, the electrolyte comprises one or more solvents. The solvent may comprise water, an organic solvent, or ionic liquids. In particular, non-aqueous solutions may include deep eutectic solvents, ionic liquids, room temperature ionic liquids (RTIL), ionogels, and other organic solvents, which support ionic conductivity and metal dissolution.

When present, the organic solvent may be a polar protic solvent, a polar aprotic solvent, a non-polar solvent, or combinations thereof. Suitable examples of polar protic solvents include, but are not limited to alcohols such as methanol, ethanol, isopropanol, n-propanol, isobutanol, n-butanol, s-butanol, t-butanol, and the like; diols such as propylene glycol; organic acids such as formic acid, acetic acid, and so forth; amines such as trimethylamine, or triethylamine, and the like; amides such as formamide, acetamide, and so forth; and combinations of the above.

Non-limiting examples of suitable polar aprotic solvents include acetonitrile, dichloromethane (DCM), diethoxymethane, N,N-dimethylacetamide (DMAC), N,N-dimethylformamide (DMF), dimethyl sulfoxide (DMSO), N,N-dimethylpropionamide, 1,3-dimethyl-3,4,5,6-tetrahydro-2(1H)-pyrimidinone (DMPU), 1,3-dimethyl-2-imidazolidinone (DMI), 1,2-dimethoxyethane (DME), dimethoxymethane, bis(2-methoxyethyl)ether, 1,4-dioxane, N-methyl-2-pyrrolidinone (NMP), ethyl formate, formamide, hexamethylphosphoramide, N-methylacetamide, N-methylformamide, methylene chloride, nitrobenzene, nitromethane, propionitrile, sulfolane, tetramethylurea, tetrahydrofuran (THF), 2-methyltetrahydrofuran, trichloromethane, and combinations thereof.

Suitable examples of non-polar solvents include, but are not limited to, alkane and substituted alkane solvents (including cycloalkanes), aromatic hydrocarbons, esters, ethers, combinations thereof, and the like. Specific non-polar solvents that may be employed include, for example, benzene, butyl acetate, t-butyl methylether, chlorobenzene, chloroform, chloromethane, cyclohexane, dichloromethane, dichloroethane, diethyl ether, ethyl acetate, diethylene glycol, fluorobenzene, heptane, hexane, isopropyl acetate, methyltetrahydrofuran, pentyl acetate, n-propyl acetate, tetrahydrofuran, toluene, and combinations thereof.

A electrolyte comprising organic solutions frequently exhibit greater viscosity, which can cause slower molecular diffusion but benefits from increased particle suspension capacity. Electrolyte having organic solvent may also display much larger electrochemical windows (2 V to 6 V), compared to water (about 1.23 V). Organic solvents may also have greater operating temperature ranges above the 100° C. limit for aqueous systems. Generally, organic solutions do not codeposit with the metal during deposition. Organic solvents also allow deposition of more reactive metals, including pure Fe and Al. For at least these reasons, some electrolytes may comprise an organic solvent.

In other embodiments, the electrolyte may comprise an ionic liquid, such as a room-temperature ionic liquid (RTIL), which are relatively non-volatile, highly tunable molten salts whose melting points are below ambient temperature. RTILs are solvents with low viscosities (10-100 cP), low melting points, a range of densities, and relatively small molar volumes. Generally, RTILs consist of a cation and an anion.

The cation in the RTIL may include, but is not limited to, imidazolium, phosphonium, ammonium, and pyridinium. In particular embodiments, the RTIL comprises an imidazolium cation; that is, the RTIL is an imidazolium-based ionic liquid. Each cation may be substituted with one or more R groups, such as an imidazolium having the formula [Rmim] or [R$_2$mim], wherein "mim" references the imidazolium. The R group may comprise one or more n-alkyl, branched alkyl, alkenyl, such as vinyl or allyl, alkynyl, fluoroalkyl, benzyl, styryl, hydroxyl, ether, amine, nitrile, silyl, siloxy, oligo(ethylene glycol), isothiocyanates, and sulfonic acids. In particular, the R group may be an alkyl selected from methyl or ethyl.

The RTIL may be functionalized with one, two, three, or more oligo(alkylene glycol) substituents, such as an oligo (ethylene glycol). Alternatively, the oligo(alkylene glycol) may be a methylene glycol or a propylene glycol. A vicinal diol substituent on the RTILs may provide greater aqueous solubility and possible water miscibility. Polymerizable RTILs may be provided choosing one or more R groups on the cation from a styrene, vinyl, allyl, or other polymerizable group.

Examples of suitable cations in the RTIL include, but are not limited to, 1-ethyl-3-methyl imidazolium ([EMIM]), 1-hexyl-3-methyl imidazolium ([HMIM]), 1-vinyl-3-ethyl-imidazolium ([VEIM]), 1-allyl-3-methyl-imidazolium ([AMIM]), 1-hexyl-3-butyl-imidazolium ([HBIM]), 1-vinyl-3-methylimidazolium ([VMIM]), 1-hydroxyundecanyl-3-methylimidazolium ([(C$_{11}$OH)MIM]), tetrabutylphosphonium ([P4444]), 1-(2,3-dihydroxypropyl)-alkyl imidazolium ([(dhp)MIM]), and combinations thereof. For example, the cation may be 1-ethyl-3-methyl imidazolium ([EMIM]). The cation may be 1-hexyl-3-methyl imidazolium ([HMIM]). The cation may be 1-vinyl-3-ethyl-imidazolium ([VEIM]). The cation may be 1-allyl-3-methyl-imidazolium ([AMIM]). The cation may be 1-hexyl-3-butyl-imidazolium ([HBIM]), 1-vinyl-3-methylimidazolium ([VMIM]). The cation may be 1-hydroxyundecanyl-3-methylimidazolium ([(C$_{11}$OH)MIM]). The cation may be tetrabutylphosphonium ([P4444]). The cation may also be 1-(2,3-dihydroxypropyl)-alkyl imidazolium ([(dhp)MIM]).

Suitable anions (X) in the RTIL include, but are not limited to, chloride (Cl), bromide (Br), iodide (I), triflate (OTf), dicyanamide (DCA), tricyanomethanide (TCM), tetrafluoroborate (BF$_4$), hexafluorophosphate (PF$_6$), taurinate (Tau), and bis(trifluoromethane)sulfonimide (TSFI). For example, the anion may be triflate (OTf). The anion may be dicyanamide (DCA). The anion may be tricyanomethanide (TCM). The anion may be tetrafluoroborate (BF4). The anion may be hexafluorophosphate (PF6). The anion may be taurinate (Tau). The anion may be bis(trifluoromethane) sulfonimide (TFSI).

Any combination of cations and anions described may form a suitable RTIL. Examples of suitable RTILs include, but are not limited to, 1-ethyl-3-methyl imidazolium bis (trifluoromethane)sulfonamide ([EMIM][TFSI]), 1-hexyl-3-methyl imidazolium bis(trifluoromethane)sulfonamide ([HMIM][TFSI]), 1-vinyl-3-ethyl-imidazolium bis(trifluoromethane)sulfonamide ([VEIM][TFSI]), 1-allyl-3-methyl-imidazolium bis(trifluoromethane)sulfonamide ([AMIM][TFSI]), 1-hexyl-3-butyl-imidazolium bis(trifluoromethane) sulfonamide ([HBIM][TFSI]), 1-vinyl-3-methylimidazolium bis(trifluoromethane)sulfonamide ([VMIM][TFSI]), 1-hydroxyundecanyl-3-methylimidazolium bis(trifluoromethane)sulfonamide ([(C$_{11}$OH)MIM] [TFSI]), 1-ethyl-3-methylimidazolium tricyanomethanide ([EMIM][TCM]), tetrabutylphosphonium taurinate, ([P4444][Tau]), 1-ethyl-3-methylimidazolium dicyanamide ([EMIM][DCA]), 1-(2,3-dihydroxypropyl)-alkyl imidazolium dicyanamide ([(dhp)MIM][DCA]), 1-(2,3-dihydroxypropyl)-3-alkyl imidazolium tetrafluoroborate ([(dhp)MIM] [BF4]), 1-(2,3-dihydroxypropyl)-3-alkyl imidazolium bis (trifluoromethane)sulfonimide ([(dhp)MIM][TFSI]), 1-(2,3-dihydroxypropyl)-3-alkyl imidazolium hexafluorophosphate ([(dhp)MIM][PF6]), or combinations thereof. In particular, the room-temperature ionic liquid may be 1-ethyl-3-methylimidazolium chloride (EMIC). Exemplary RTILs are further illustrated below at Table 1.

TABLE 1

Exemplary RTILs.

| Abbreviation | Chemical Name | Structure |
|---|---|---|
| EMIC, [EMIM][Cl] | 1-ethyl-3-methylimidazolium chloride | 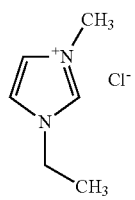 |

TABLE 1-continued

Exemplary RTILs.

| Abbreviation | Chemical Name | Structure |
|---|---|---|
| [EMIM][TSFI] | 1-ethyl-3-methylimidazolium bis(trifluoromethane)sulfonimide | 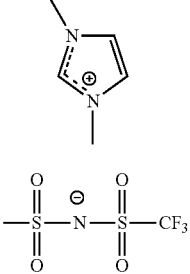 |
| [VEIM][TSFI] | 1-vinyl-3-ethyl-imidazolium bis(trifluoromethane)sulfonimide | 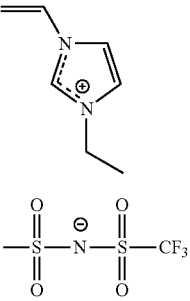 |
| [HMIM][TSFI] | 1-hexyl-3-methyl-imidazolium bis(trifluoromethane)sulfonimide | 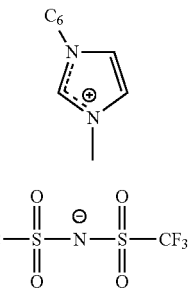 |
| [AMIM][TSFI] | 1-allyl-3-methyl-imidazolium bis(trifluoromethane)sulfonimide | 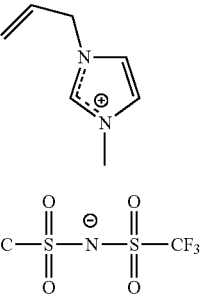 |
| [HBIM][TSFI] | 1-hexyl-3-butyl-imidazolium bis(trifluoromethane)sulfonimide | 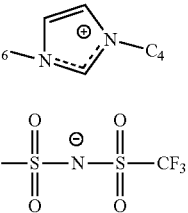 |

TABLE 1-continued

Exemplary RTILs.

| Abbreviation | Chemical Name | Structure |
|---|---|---|
| [VMIM][TSFI] | 1-vinyl-3-methylimidazolium bis(trifluoromethane)sulfonimide | 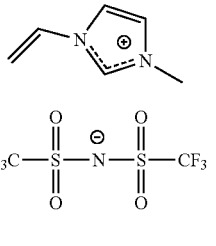 |
| [(C₁₁OH)MIM][TSFI] | 1-hydroxyundecanyl-3-methylimidazolilum bis(trifluoromethane)sulfonimide | 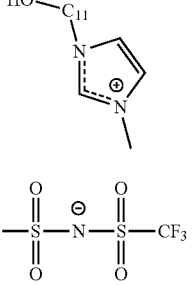 |
| [EMIM][TCM] | 1-ethyl-3-methylimidazolium tricyanomethanide | 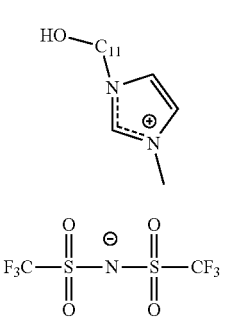 |
| [P4444][Tau] | tetrabutylphosphonium taurinate | 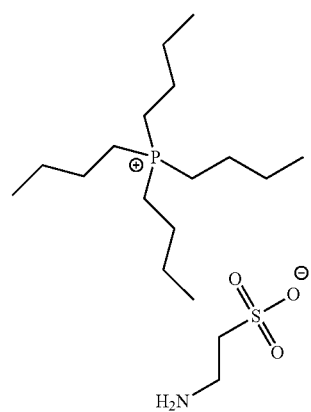 [SMILES: CCCC[P+](CCCC)(CCCC)CCCC ; NCCS(=O)(=O)[O-]] |
| [EMIM][DCA] | 1-ethyl-3-methylimidazolium dicyanamide | 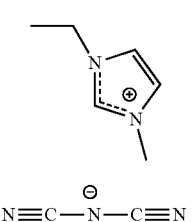 |

TABLE 1-continued

Exemplary RTILs.

| Abbreviation | Chemical Name | Structure |
| --- | --- | --- |
| [DMIM][Tf2N] or [DEIM][Tf2N] | 1-(2,3-dihydroxypropyl)-3-methylimidazolium bis(trifluoromethanesulfonimide) or 1-(2,3-dihydroxypropyl)-3-ethylimidazolium bis(trifluoromethanesulfonimide) | 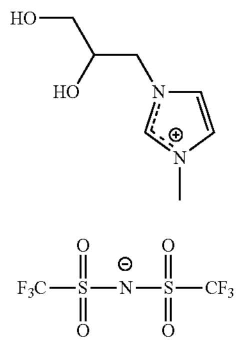 |
| [DMIM][BF4] or [DEIM][BF4] | 1-(2,3-dihydroxypropyl)-3-methylimidazolium tetrafluoroborate or 1-(2,3-dihydroxypropyl)-3-ethylimidazolium tetrafluoroborate | 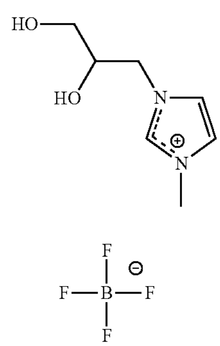 |
| [DMIM][DCA] or [DEIM][DCA] | 1-(2,3-dihydroxypropyl)-3-methylimidazolium dicyanamide or 1-(2,3-dihydroxypropyl)-3-ethylimidazolium dicyanamide | 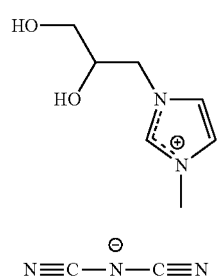 |
| [DMIM][PF6] or [DEIM][PF6] | 1-(2,3-dihydroxypropyl)-3-methylimidazolium hexafluorophosphate or 1-(2,3-dihydroxypropyl)-3-ethylimidazolium hexafluorophosphate | 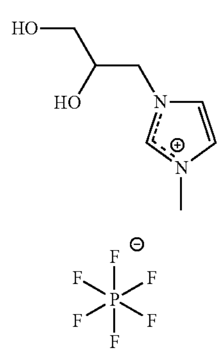 |

In other embodiments, the electrolyte may comprise an ionic liquid or composition disclosed in co-pending U.S. application Ser. No. 15/293,096, filed Oct. 13, 2016, and entitled "Metal Deposits, Compositions, Methods for Making the Same," the entire disclosure of which is incorporated herein by reference in its entirety for all purposes.

The electrolyte may comprise a mixture of water and an RTIL. For such mixtures, the volume ratio may be between about 99:1 and about 1:99 water/RTIL, such as between about 99:1 and about 95:5 water/RTIL, between about 95:5 and about 90:10 water/RTIL, between about 90:10 and about 85:15 water/RTIL, between about 85:15 and about 80:20 water/RTIL, between about 80:20 and about 75:25 water/RTIL, between about 75:25 and about 70:30 water/RTIL, between about 70:30 and about 65:35 water/RTIL, between about 65:35 and about 60:40 water/RTIL, between about 60:40 and about 55:45 water/RTIL, between about 55:45 and about 50:50 water/RTIL, between about 50:50 and about 55:45 water/RTIL, between about 55:45 and about 45:65 water/RTIL, between about 45:65 and about 40:60 water/RTIL, between about 40:60 and about 35:65 water/RTIL, between about 35:65 and about 30:70 water/RTIL, between about 30:70 and about 25:75 water/RTIL, between about 25:75 and about 20:80 water/RTIL, between about 20:80 and about 15:85 water/RTIL, between about 15:85 and about 10:90 water/RTIL, between about 10:90 and about 5:95 water/RTIL, or between about 5:95 and about 1:99 water/RTIL. In particular, the molar ratio may between about 70:30 and about 20:80 water/RTIL, between about 60:40 and about 30:70 water/RTIL, or at about 40:60 water/RTIL. In another example, the electrolyte may only contain a trace amount of water, such as that absorbed from the atmosphere. That is, the electrolyte may be substantially non-aqueous.

The electrolyte may have at a temperature above 0° C. and below about 250° C., such between about +0° C. and about 10° C., between about 10° C. and about 20° C., between about 20° C. and about 30° C., between about 30° C. and about 40° C., between about 40° C. and about 50° C., between about 50° C. and about 60° C., between about 60° C. and about 70° C., between about 70° C. and about 80° C., between about 80° C. and about 90° C., between about 90° C. and about 100° C., between about 100° C. and about 110° C., between about 110° C. and about 120° C., between about 120° C. and about 130° C., between about 130° C. and about 140° C., between about 140° C. and about 150° C., between about 150° C. and about 160° C., between about 160° C. and about 170° C., between about 170° C. and about 180° C., between about 180° C. and about 190° C., between about 190° C. and about 200° C., between about 200° C. and about 210° C., between about 210° C. and about 220° C., between about 220° C. and about 230° C., between about 230° C. and about 240° C., between about 240° C. and about 250° C., between about 250° C. and about 260° C., between about 260° C. and about 270° C., between about 270° C. and about 280° C., between about 280° C. and about 290° C., or between about 290° C. and about 300° C.

The pH of the electrolyte may vary depending upon the embodiment. Different metals and composites typically have pH requirements to maintain a stable mixture in solution. The wetting characteristics of surfactant maintain its presence at the first electrode/electrolyte interface. Therefore, the surfactant may also buffer against the dramatic pH gradients that occur between the interface and the electrolyte bulk due to proton consumption and metal hydroxide precipitation on the substrate.

The dielectric constant of the electrolyte is responsible for how a wave propagates through the medium. The higher the constant, the more compressed the wave and the slower its travel time. Low dielectric constants allow fast travel near the speed of light. Electrolytes are conductive, taking and dissipating energy from the wave as it propagates. As such the parameters of the current are adjusted to account for the dielectric constant. In water, about 11% speed of light with dielectric of about 80. RTILs have a dielectric constant of about 40, and air a constant of about 1.

2. Metal

Generally, the electrolyte comprises metal. The metal may be metal particles, such as dissolved or suspended metallic micro- or nanoparticles, or molecular metal ions, such as dissolved metal salts. Examples of suitable metals include, but are not limited to, zinc, cadmium, copper, nickel, chromium, tin, gold, silver, platinum, lead, ruthenium, rhodium, palladium, osmium, iridium, iron, cobalt, indium, arsenic, antimony, bismuth, manganese, rhenium, aluminum, zirconium, titanium, hafnium, vanadium, niobium, tantalum, tungsten, and molybdenum. Examples of suitable alloys having two metals include, but are not limited to gold-copper-cadmium, zinc-cobalt, zinc-iron, zinc-nickel, brass (an alloy of copper and zinc), bronze (copper-tin), tin-zinc, tin-nickel, and tin-cobalt.

In some embodiments, the electrolyte comprises metal particles. Deposition of metal particles of a desired composition, crystallinity and crystal structure may provide same or substantially similar properties to the deposited material on the first electrode with less dependence upon specific deposition parameters. Each metal particle brings millions of preformed metal bonds, resulting in proportionality less energy needed from the first current to complete the bonding deposit compared to conventional electrodeposition. The particle volume also dramatically accelerates the bonding deposition rate. At least for these reasons, particle codeposition improves the time and energy efficiency of the methods disclosed herein.

In contrast, conventional electrodeposition is very slow because individual metal atoms must migrate through liquid to the metal surface to deposit, one by one. Without wishing to be bound by theory, when metal particles electrically contact the first electrode, dissolved metal species also deposit on and around the metal particle in brick-and-mortar fashion until the metal particle is completely occluded. Before occlusion, however, the metal particle itself does not chemically bond to the first electrode unless its surface atoms are in a reducible state. As such, depositing molecular species push away the metal particles from the surface instead of becoming occluded. Metal particles that occlude may have trapped electrolyte between them and the surface. This porosity is detrimental to the mechanical integrity of the deposit. Conventional electrodeposition rarely occludes over 10 vol % metal particles.

The composition of the metal particles may match that of the first electrode. Metal particles of two or more elements, such as Al and Fe, may be mixed in a desired stoichiometry to yield an alloy. Mixed metal particles may codeposit an element poorly soluble in the electrolyte or for which reduction to a metallic state is outside the electrochemical potential window of the electrolyte. For example, aluminum is molecularly reducible in EMIC, while iron is not. Ceramic or polymer particles may be codeposited with metal particles to obtain deposit properties outside the range or alterability of a base metal alone.

Particles of dielectric polymers may be codeposited to modify the dielectric properties of the deposit, or to increase deposition rate without increasing the potential for surface roughness (molecular species deposit around dielectric particles, and atop conductive particles leading to roughness with the latter).

The electrolyte may comprise a metal salt. Any metal salt known within the electrochemical arts is suitable for this method.

3. Additives

The electrolyte may further comprises one or more additives, including but not limited to, acids, bases, salts, surfactants, thickeners, buffers, ionizable organic compounds, and fibers. In particular, the electrolyte may comprise thickener to modulate the viscosity and increase the mass of particulates stably suspended in the liquid electrolyte.

In some embodiments, the electrolyte may comprise fibers. Fibers may increase the mass electrodeposited on the first electrode per time per charge applied between the first electrode and source of a countercharge. Fibers suspended within the electrolyte may be codeposited with metals at the first electrode to modulate the mechanical properties of the deposited material. Fibers based upon carbon, silicon or other materials may modify the tensile strength, ductility, or other properties.

In other embodiments, the electrolyte may comprise a surfactant. The surfactant, when present, may be sodium dodecyl sulfate (SDS), ammonium lauryl sulfate, or a block copolymer, such as polyethylene glycol. In particular sodium dodecyl sulfate may be mixed with alkali to reduce the adsorption strength between the surfactant and the surface. Alternatively, the ionic sulfate headgroup of SDS may be replaced with sulfamate to achieve this effect without increasing alkali content.

In a polar solutions, concentrations of surfactant above the critical micelle concentration (CMC) result in micelles, which may encapsulate particulates to increase their effective solubility and mass loading, and to insulate suspended particles from the oxidizing effects of water-induced passivation and corrosion. Surfactants may also mitigate dendritic nucleation and growth, resulting in a more even deposition across the first electrode. Surfactants may decrease the first electrode's surface energy and facilitate removal of hydrogen bubbles to avoid pits and pores than can otherwise form in the deposited material. Surfactants may also brighten by inhibiting the buildup of more oxidized species such as Fe', removing the need for post-treatments normally required to provide a polished surface.

While protecting suspended or dissolved particles against oxidation, a surfactant shell can itself be an energy barrier to electrodeposition. Additional overpotential may be needed to decompose the surfactant so that charge transfer may reach the particle surface. Long and short chain surfactants with electrically conductive backbones may lower overpotentials associated with surfactant.

The range of concentration of additives in the electrolyte can and will vary. Generally the concentration of additives in the electrolyte may rage between about 10' mol/L and about $10^{-5}$ mol/L, such as between about 10' mol/L and about $10^{-3}$ mol/L, between about $10^{-3}$ mol/L and about 10' mol/L, or between about 10' mol/L and about $10^{-5}$ mol/L.

When present, the concentration of surfactant within the electrolyte may be much greater than that of other additives. If the additive is a surfactant that can be incorporated into the deposit on the first electrode, the surfactant concentration should be minimized in the electrolyte by balancing the smallest concentration of surfactant with the average chain length of surfactant. Long-chain neutral surfactants are typically more effective at increasing the viscosity of a solution, but may decrease the diffuse mobility of encapsulated particles. Short-chain ionic surfactants may increase the diffuse mobility of encapsulated particles, while enhancing the ionic conductivity of the supporting solution.

C. Source of a Countercharge

The methods and devices of the present disclosure may also comprise a source of a countercharge. When present, referring to FIG. 1A, the source of a countercharge 120 may be an electrode counter to the first electrode 110, where the first current 130 is induced between the first electrode 110 and the source of a countercharge 120. The source of a countercharge generally provides an anode for an electrochemical process described herein.

In some embodiments, the source of a countercharge may be a non-corroding electrode, which is generally stable during induction of a first current. That is, the non-corroding electrode does not dissolve or release metal into the electrolyte because of a chemical potential between it and the electrolyte, or because of an electric potential between the source for a countercharge and the first electrode.

Suitable examples of non-corroding electrodes include, but are not limited to, Pt, Au, boron-doped diamond, or platinized or gold-coated conductive substrate. Suitable soluble electrodes include, but are not limited to, Fe, Al, Cu, or any other electrically conductive metal, including alloys and composites. Electrodes may be interchangeable to facilitate routine replacement and maintenance and reconfiguration. Although presented here in the source of a countercharge, non-corroding electrodes may also be electrodes in other capacities, including cathodes and reference electrodes.

In other embodiments, the source of a countercharge may be a corroding electrode, which dissolves when a first current is applied between the corroding electrode and a first electrode through an electrolyte, suspending the one or more metal species into the electrolyte. Referring to FIG. 1B, a corroding electrode is depicted as a possible source of a countercharge. When the first current 130 is induced between the corroding electrode 120 and the first electrode 110 through the electrolyte 140, metal 122 from the corroding electrode 120 is released as metal species ($M^+$) 124 into the electrolyte 140. Additional metal can be in the electrolyte when the electrode is corroding, for example from metal salts dissolved in the electrolyte. In other instances, the only metal source is from metal species released from the corroding electrode.

In various embodiments, a corroding electrode may comprise one or more metal species selected from the group consisting of metal particles, metal ions, and combinations thereof. Dissolving the corroding electrode releases new metal into the electrolyte, maintaining its concentration through the duration of the method. The metal-carrying capacity of the electrolyte becomes less important because fresh metal can be supplied from dissolution of the corroding electrode. Metal precursors are supplied from the controlled corrosion of a formulated source of a countercharge into the electrolyte near the first electrode.

The corroding electrode may further comprise one or more ceramic particles or dielectric polymers. The corroding electrode may be formed by pressing together metal particles into a solid body, with or without binding agents. The corroding electrode may be made by any number of thermal, pressure, or chemical synthesis methods. In one instance, the corroding electrode may be made by pressing metal powders into an electrode geometry, such as a rod for gun-feed style applicators, or as a disk-pellet for patch style applicators. In some instances metal and/or composite powder may be mixed in a vial, added to the inside a die in a hydraulic press, pressed together, and removed as a metal pellet for use an as a corroding anode.

The corroding electrode may comprise one or more sizes and geometries of particles. During deposition, corrosion of the source of a countercharge may occur primarily along the grain boundaries of the pressed particles when higher current densities are used, causing their release into solution with their approximately original dimensions. Particles dissolved in this way are surface activated and exhibit a higher solubility in the electrolyte than particles simply mixed into solution. Particles with a surrounding layer of metal-species which is electroactive for deposition, such as $Al_4Cl_7$ in 1-ethyl-3-methylimidazolium chloride (EMIC), are more readily codeposited.

The metal particles may have grain sizes selected to grain sizes of the first electrode. Metal particle size may be small enough to remain suspended in the electrolyte and avoid the effects of gravity or control the impact of grain size on the properties of the deposit. Larger grains result in a harder metal from a slower process. Smaller grains yield softer metal with more ductility from a faster deposition. The larger the discrepancy at the grain boundary defines points of failure.

Grain sizes may be selected to match those of the substrate, helping increase continuous uniformity between the substrates. New metal strongly fills gaps in the workpiece along the metal line. Pores are closed in the deposition. The former gap is superimposed with new material defined by an elongated grain structure and high aspect ratios. This morphology is structured by the waveform of the transverse current.

In some embodiments, the metal particles may have rough or non-symmetric dimensions. In other embodiments, the metal particles may have spherical dimensions and a uniform surface energy. In still other embodiments, the metal particles may have an elongated dimension, which aligns with a second current induced across the first electrode, the second current being transverse to the first current, and the second current inducing a relativistic charge across the first electrode.

Without wishing to be bound by theory, rough or non-symmetric particles may be more easily suspended in solution and can be codeposited in yield higher than symmetric particles. Spherical particles with uniform surface energy may codeposit such that the overall finish of the deposit is more predictable and easy to control. Elongated particles may align themselves with the electric or magnetic fields of second current and encourage directional growth, bridging a gap between two first electrodes more rapidly.

D. First Current (Electric Field)

Using the methods described herein, referring to FIG. 1A, the first current 130 is an induced current between the source of the countercharge 120 and the first electrode 110 through the electrolyte 140. The first current 130 may the result of an electric field between the source of the countercharge 120 and the first electrode 110 through the electrolyte 140. The first current polarizes the workpiece so that it possesses a net negative charge. This negative charge effects a charge transfer reaction with dissolved and suspended metal ions and particles from the electrolyte to effect new metal-metal bonds with metals on the surface of the workpiece.

The first current may be modulated in its power, voltage, amperage, frequency, duration, and other parameters. The first current may be induced using a pulse plating or a reverse-pulse plating scheme, where a pulsed power is applied to sequences of galvanostatic, galvanodynamic, potentiostatic, and potentiodynamic power to the first electrode through the first current. Such pulses may be applied in a repeating sequence.

Shorter pulses of polarization of the workpiece may maintain a relatively stable concentration balance of the metal species at the workpiece/electrolyte interface. Dissolved metal salts and suspended metal particles in an electrolyte have different diffusion rates and require different energies to electrophoresis. As the metal species approach the surface of the workpiece, concentration of metal salts and metal particulate become imbalanced compared to the bulk electrolyte. Because the metal salts diffuse more quickly than metal particles, they reach the surface at a faster rate and are more likely to be deposited. Shorter pulses of polarization allows these metal species to equilibrate during the electrochemical process.

Pulse plating or reverse-pulse plating schemes through the first circuit smoothen the surface and retard deposition. Pulse plating typically uses an on-off pulse rather than a sine wave. The off cycle allows fresh electrolyte to diffuse into features on the workpiece. The on cycle drives deposition onto the workpiece. The primary benefit of pulse plating is that the off-cycles of the pulse allow more time for convection of the electrolyte near the surface. This can restore a more uniform concentration of fresh reactants across the surface despite faster depletion at rough areas during the on cycle. During the ON period, rough areas still experience higher charge density than smooth areas and so the benefit of pulse plating has limitations. Sequences of pulses of opposite polarity may increase the adhesion and mechanical strength of deposited metal, by promoting a greater number of metal-metal bonds.

Pulses may include dynamic current or potential ramp rates, for example a pulse applied at about 5 mA/$\mu$s from between about 0 mA and about 2 mA, followed by −0.2 mA/$\mu$s from between about 2 mA and about 0 mA. Pulses may involve uniform or disproportional changes in polarity, for example a pulse with lower and upper bounds of between about −1.5 V and about 1.5 V, or between about −1.5 V and about 0.7 V. These pulses may be generated from an electroplating power supply, which may be power supply 160, or a reverse pulse rectifier used to generate a DC current for electrochemical processes.

When used, pulse plating occurs over a defined period, such as 1 to 1000 microseconds for aqueous electrolytes. The period may be static, where the same time interval spaces each pulse, or it may be dynamic, where the periods change between each pulse. The length of the period may be longer for electrolytes that are more viscous.

For example, referring to FIG. 3, preprocessing the first electrode may involve positively polarizing the first electrode to corrode the surface of the first electrode into the electrolyte (310). Preprocessing may then be followed by a negative polarization, which electrodeposits more material onto the first electrode than was corroded off in the previous step (320). The negative polarization may then be followed by induction of a second current transverse to the first current of the negative polarization (330). The completeness of the electrochemical process may be assessed (340). If the electrochemical process is not complete, the first current and/or the second current are modulated the desired material was deposited while assuring superior surface penetration (350). If the electrochemical process is complete, the process is terminated (360).

A similar sequence might also continuously corrode and redeposit material from the surface of particles already deposited onto the first electrode. This approach could homogenize the surface and increase bonding across the entire surface boundary of deposited particles. In this way, an initial sequence of pulses may clean the surface of the first electrode.

A final sequence of pulses may be affected to passivate (or pickle) the surface of the first electrode. Electropolishing, when used, may leave the deposited material with the corrosion resistance finish. Pulsed power may decrease the lattice strain and surface roughness of deposited metal. For deposits with thickness around 1 millimeter or more, mitigation of lattice strain is less important because fractures after several micrometers of deposit are eventually filled-in with more material.

E. Second (Transverse)Current (Induced Potential)

Following the methods described herein, referring to FIGS. 1A, 2, and 6B, a second current 150 (which current may be from an induced potential 250) can be applied through and/or across the surface 111 of the first electrode 110 to affect surface electrons 420 and induce favorable properties in the deposit without altering the parameters of the first current 130, the electrolyte 140 or the source of a countercharge 120. The electrons 450 at the surface 111 experience a forward compression and rearward expansion of their electric field. This compression and expansion generates a relativistic charge 112 propagating outward from the electron's center at the speed of light. The relativistic charge then bends the field lines of the first current 130, directing metal from the electrolyte to form new metal-metal bonds on the first electrode.

Viewed in another way, the induced potential bends the field lines proximate the surface so metal from the electrolyte follows a path of the bent field lines to deposit the metal onto the surface. The bent field lines ultimately intersect the surface, including irregularities in the surface, at 90 degrees within close proximity to the portion of the surface being intersected. The difference between a point of deposition under the induced potential and a point of deposition without the induced potential is a shift of the field lines toward crevices and rough areas of the surface not normally filled.

The second current can augment many aspects of electroplating and electrodeposition processes, including, but not limited to, two-dimensional growth (smoothness and uniformity); grain properties, such as crystallinity and morphology; induced nucleation on energetically difficult surfaces; reduced porosity in the metal; adhesion onto the substrate; and controlled linear crystalline growth. Therefore, the properties of the deposited metal can be changed without heat, pressure, or modifying the system's components or normal deposition parameters.

The second current, or transverse current, however, is more than a mere improvement on electroplating or electrodeposition. This is an entirely different current than the first current used to drive metal species to the surface of the workpiece. The results achieved using the present electrochemical methods are impossible with conventional electroplating or electrodeposition techniques.

Figure 7:
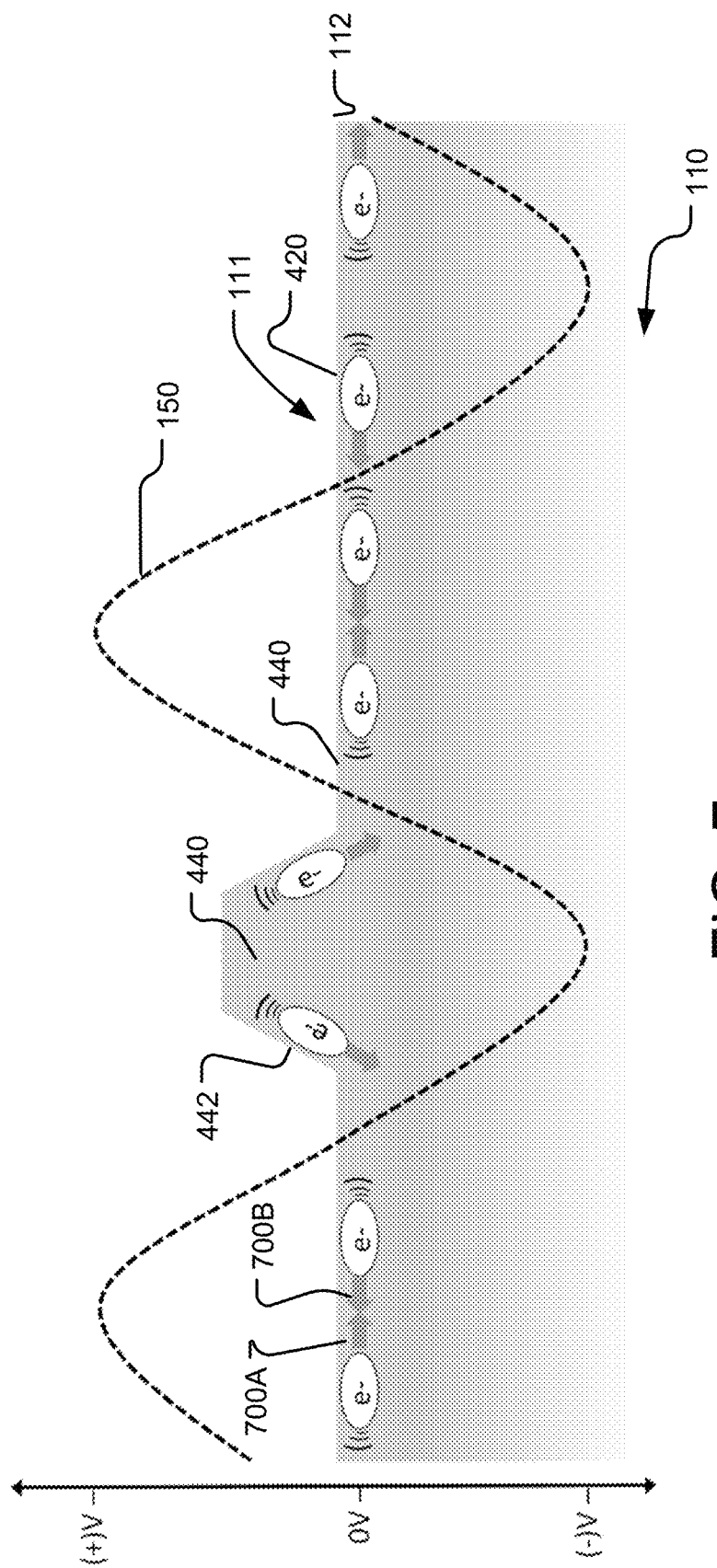
FIG. 7 depicts an electron distribution due to sinusoidal second current 150.

Some benefits of the transverse current are illustrated at FIG. 7. In this example, the second current 150 is in the form of a bipolar, sinusoidal waveform across a surface 111 of the first electrode 110. Without a transverse current, the electrons 420 are considered stationary for purposes of this discussion because, while the electrons are in fact moving, their net movement is relatively slow as per Equation 2, as well as non-uniform as a result of electrode resistivity and electrolyte convective field effects. Thus, no relativistic effect is present. The second current 150 effects a relativistic change 112, causing electrons 420 to move across the surface 111 in the directions 700A, 700B of the imposed electric field. When the second current ($V_{TC}$) is positive, electrons 420 accelerate toward the right (700A), and when $V_{TC}$ is negative, electrons accelerate toward the left (700B). This shuffling of the positions of electrons 420 at the surface 111 changes the electron distribution, and therefore, the localized charge density. When the waveform of $V_{TC}$ approaches 0, electrons may be bunched together or pushed apart farther than normal. In the former, a smooth point 430 on the surface 111 may experience the charge density normally seen at points with greater curvature 440. Similarly, the charge density at curved points 440 may be reduced from their normal values.

This change in the electron distribution then alters the behavior of metal atoms approaching the surface. Conventionally, the charge density is greater around irregularities of the workpiece, which then promote layers of metal to build up the irregularities even more. Instead, in the disclosed method, atoms are encouraged to follow a path to generate a smooth surface, because areas that would have a large charge density absent the transverse current have a lower than typical charge density, and areas with a small charge density absent the transverse current have a greater than typical charge density. The frequency of the transverse current's waveform can be swept through several values so irregularities of many sizes may be modulated.

The second current may be chosen from an alternating current (AC), or a combination of an AC current and a direct current (DC) offset upon which the AC current is imposed. When the second current combines the AC second current and the DC second current, the DC second current may offset the AC second current by an amount less than an electrochemical breakdown of the electrolyte.

Figure 8:
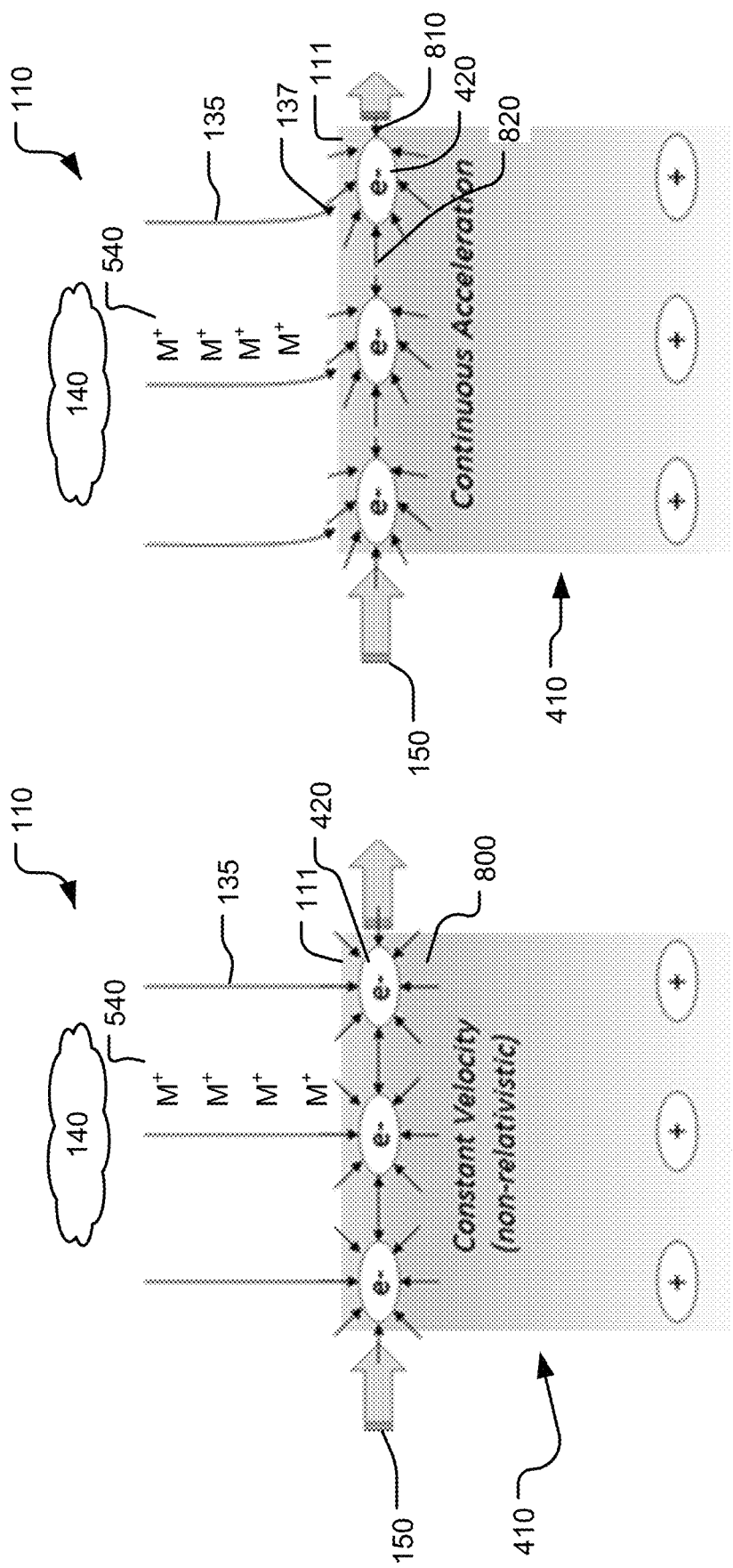
FIGS. 8A-8B depict the effect of a second current 150 on the electric field 135 of a first electrode 110 when surface electrons 420 are moving at constant, non-relativistic velocity (FIG. 8A) and at continuous acceleration (FIG. 8B), imparting a relativistic charge 112.

When DC is used alone, it moves electrons on the surface of the first electrode at a constant velocity, but it does not accelerate them to generate a relativistic charge at the surface. As shown in FIG. 8A, electrons 420 moving at constant velocity maintain uniform spacing and constant electric field vectors. A DC offset second current 150 applied to the first electrode 110 causes a net flow of electrons at a constant velocity in the bulk and surface of the first electrode 110 inducing a magnetic field at all depths. The bulk fields cancel, while surface fields propagate outside the conductor. Consequently, a DC offset second current only weakly impacts the electric field lines 150 from cathodic polarization of the first electrode 110 under the first circuit 130.

A DC offset (e.g. 0.5 V) keeps the transverse current from being centered at zero, so that on the backside of the workpiece, one side of the gap would have more deposition and the other side of the gap more corrosion. Effectively, the DC offset makes one side of the gap act like the anode more often and the other side of the gap to act like the cathode. The gap will be filled.

With constant velocity electrons, their electric fields are contracted tangential to the surface, and a field intensity increase in the perpendicular directions, following the Liénard generalization:

$$\gamma \equiv \frac{1}{\sqrt{1 - \frac{v^2}{c^2}}} \qquad \text{(Equation 1)}$$

where $\gamma$ is the contraction constant, v is the velocity of the electron, and c is the speed of light ($3 \times 10^8$ m/s). Here, the electron velocity is non-relativistic, so the degree of this effect is small.

When the AC second current is used, however, regular or constant charge acceleration is induced (FIG. 8B). Under acceleration, electrons experience a forward compression 810 and rearward expansion 820 of their electric field, which propagates outward from the electron's center at the speed of light. The term "relativistic charge" refers to this constant acceleration at or near the speed of light at the surface of the first electrode. Before now, electron acceleration and its effects had not been explored in electrochemical processes. The vector of acceleration changes with the waveform. That will help further qualify the last sentence of this paragraph, because electron acceleration Referring again to FIG. 8A, electric field lines 135 due to cathodic polarization of the first electrode 110 are normal to the tangential point of the surface 111 due to the symmetry of the electron's electromagnetic field. When the electron's electromagnetic field is no longer symmetric due to movement of the charge, the polarization field lines are proportionately shifted (137, FIG. 8B). Metals in the electrolyte (M⁺) flowing to or from the first electrode 110 follow the paths 135 of these polarization field lines. The field-shifting effect using the second current 150 may be maintained for periods similar to the diffusion rates of ionic reactants and the reaction kinetics.

When the workpiece has a void, the second current may have a DC offset to introduce a potential drop within the void. When two workpieces are not in electrical contact, the DC offset is applied with consideration to the electrolyte stability. Most electrolytes have a window of stability around +/−6 V. If the workpieces are in electrical contact, the DC offset can be much greater without damaging the electrolyte, because the current can complete a circuit without depending entirely upon charge pass through the electrolyte. The electrical contact need not be within the area targeted for deposition, and the DC offsets can be much more than +/−6 V, including up to +/−200 V. Gap geometry may also affect the limits of the DC offset.

The strength of this electric field, V/m, may be stronger than the electric field of the first current to reroute metal ions from the first current into the void. The DC offset may correlate to the voltage at root-mean-square ($V_{RMS}$) or the voltage at root-mean-square ($I_{RMS}$), while the voltage peak-to-peak (Vpp) or the current peak-to-peak (Ipp) may be bipolar. This DC offset leads to transverse growth inside the void, and also to the formation of metal-metal bonds within the gap. When the overpotential of deposition is greater, adhesion is often improved. In general, $E_{TC}$ can be much greater than $E_{ED}$, if the workpieces being joined already have some point of electrical contact. $E_{TC}$ is the electric field of transverse current from the transverse current signal source. $E_{ED}$ is the electric field of the electrodeposition signal source. Greater overpotential can also increase grain size of the deposition metal, which can harm adhesion, depending on the system.

The first and second currents may be modulated together so that the positively biased first electrode continues to experience a positive current efficiency and positive net mass gain (i.e., so the direction of the first current does not invert, and the first electrode does not become the source of a countercharge). Also, the second current can be separately modulated so a bottom-up growth occurs inside the void, a phenomenon unknown in conventional electrodeposition without organic additives (e.g., levelers). See Example 8 for more discussion.

The conductive and dielectric behavior of metal particles in the electrolyte may affect whether the second current affects electrophoretic ($F_{EP}$) or dielectrophoretic ($F_{DP}$) forces. For example, for a 10-μm dielectric particle the electrokinetic field force imparted can be up to 5 orders of magnitude stronger than that that felt by a conductive particle of the same size. For 10-nm particles, the situation is reversed. Both are frequency-dependent and particle velocity may be based on how much energy can be stored in an ionic cloud surrounding the particle (that is, the "permittivity"). As frequency increases into the kHz range, that energy usually decreases substantially.

By reducing the stored energy between the metal particle and the first electrode, particle riding and occluded porosity are reduced. Without wishing to be bound by theory, as the metal particle approaches the surface of the first electrode, the energy stored in the electrochemical double layer tangentially distributes. $E_{TC}$ competes with $E_{ED}$. The double layer barrier between the metal particle and the surface of the first electrode is reduced. The electric field also imparts an electrokinetic velocity tangential to the surface, which causes parallel wobbling as the particle approaches the surface perpendicularly. Both mechanisms reduce the porosity of deposits created with particle occlusion following the methods described herein.

F. Waveform

The second current (or induced potential) is a periodic or non-periodic waveform, such as a sine wave, a triangle wave, a saw tooth, as well as any number of other possible waveform, and combinations thereof. Each type of waveform imparts a perturbation to surface charges. Several waveforms may also be combined to define the second current. Different waveforms have different effects on the surface, even when superimposed as a multi-waveform.

Figure 9:
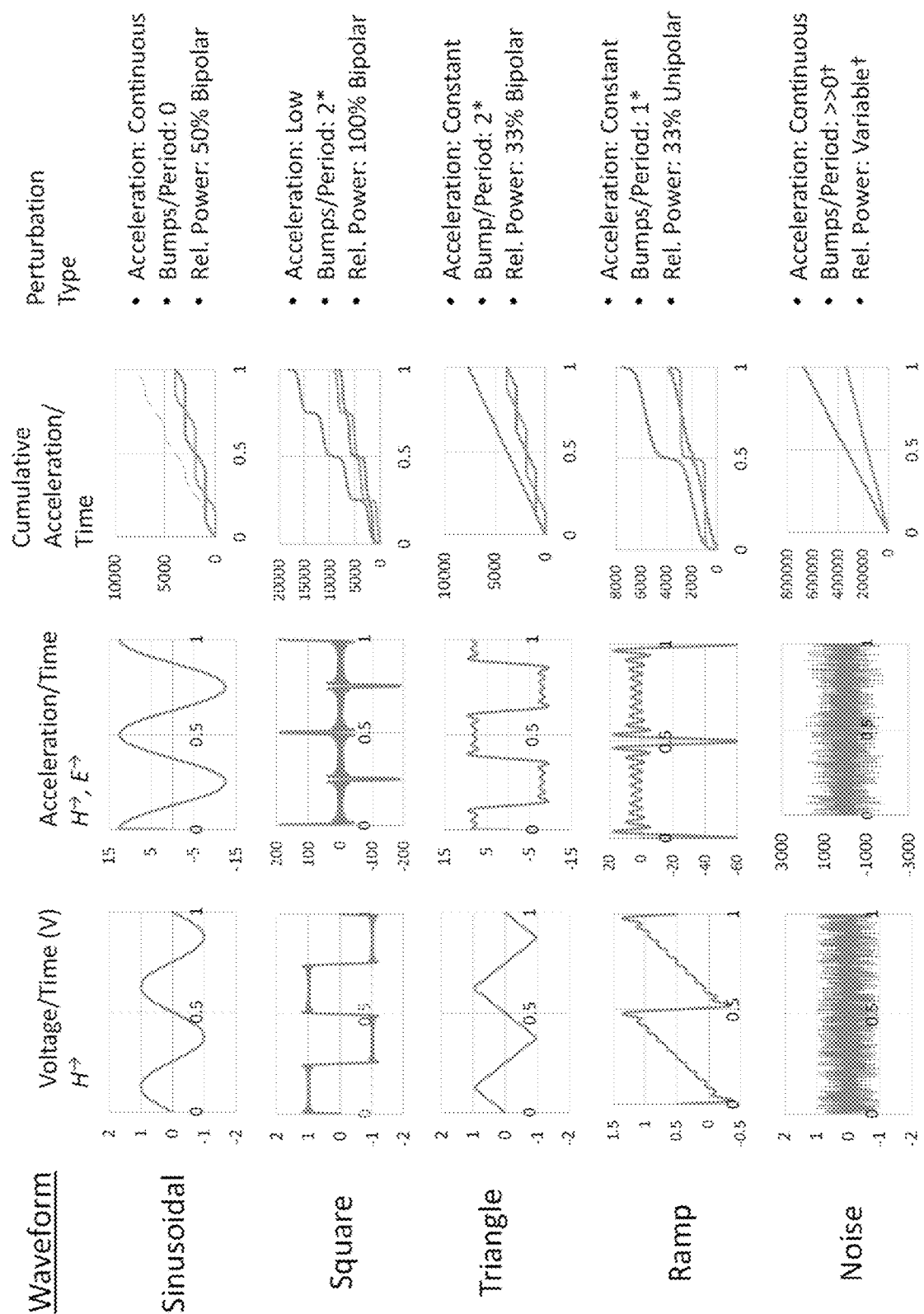
FIG. 9 depicts the properties of idealized waveform variations at 2 Volts peak-to-peak (Vpp) and 2 Hz over two periods. These variations do not account for impedance. (*) The minor bumps depends upon the harmonics and waveform integrity produced by the signal generating equipment. (†) Noise has no true period/frequency, and the actual properties depend heavily upon the signal generating equipment and type of noise.

FIG. 9 illustrates examples of the most common fundamental waveforms and their properties used in the present method. The waveform and its variable parameters (current, voltage, frequency, and duration) may be controlled to affect the second current. Waveforms induce a potential across the surface of the first electrode to move charges across the first electrode. Without wishing to be bound by theory, constant voltage over time causes charge to move in a set vector. Charge movement then induces an electric field between gaps or rough features on a first electrode, and induces a magnetic field, $\vec{H}$, at the surface of the first electrode. Changing voltage over time causes a proportionately continuous acceleration of charges, which induce both magnetic and electric fields ($\vec{H}, \vec{E}$) at the surface. A "bump" is an abrupt change in the vector of a charge, such as the apex of a triangle wave (directional bump) or a polarity change (polarity bump). Both appear in FIG. 9 as slews or asymptotic points. "Relative power" describes how different waveforms of identical peak voltage deliver power across the electrode surface. In electrochemical processes, voltage may be treated as a constraint instead of a power, because potential is thermodynamically significant to the reaction, while power relates to time and surface area.

The applied waveform may be formed from a combination of numerous waveforms based on harmonics of one or more frequencies at which the electrolyte or the first electrode exhibits absorption of the one or more frequencies. The waveform may include phase offset introduced from differences in potentials between points of contact on the workpiece. If two different sources of electrical contact are used for two separate transverse current channels, the signals of those channels can be phase-offset, as shown in the 2D simulations. (See Example 8).

Waves go all directions, reflecting and causing peaks in the signal. Non-symmetric reflections result in signal differences, allowing one to use roughness like a fingerprint to uniquely identify a sample. The waveform flows through the gap, as an electric field or as a magnetic field. The pattern can become complex. Because of the offset, the compound difference between the waveforms of the points of contact can amplify the current experienced in the gap beyond the energy. As the roughness changes, the distribution of energy also changes. If the roughness becomes smooth, the distribution of energy across the surface becomes more uniform. This change is topography can be measured with a reflection or transmission-type impedance.

The phase offset may be between 0° and 180°. With a 0° offset, the current resembles pulse plating. See Example 8 and FIG. 21. At a 45° offset, current density is effected in the gap. The magnitude of the electric current fluctuates logarithmically. See FIGS. 7 and 8. The dissolved metal atoms follow the electric field. The magnitude and polarity result from the differences in the offset. The current density (V/m) increases as the gap closes.

The second current (or induced potential) may also have a phase offset between 0° and 180°, for example a phase offset of about 90° between two electrical contacts on the surface. Here, strong vectors are felt at the surface. Some first current vectors move parallel to the surface, allowing corrosion during deposition. Microscopic analysis of deposited material showed globular pockets of amorphous rather than crystalline deposition.

At a 135° offset, first current vectors point away from the workpiece, diminishing material deposited and producing a shiny finish. A 180° offset is the largest potential difference possible. The gaps in the workpiece showed large changes with the field focused on gap filling. See Example 8 and FIG. 22. When the deposited material was rough, the energy was not presented to the surface in a way that would promote smooth deposition. Thus, the waveform of the second current was too simple, and needed to be modulated so that the deposited material is smooth instead of rough. In various embodiments, the second current (or induced potential) may have a period similar to a diffusion rate of a component in the electrolyte.

A power source may apply a waveform as a time-dependent voltage built from the superposition of multiple sinusoidal signals (analogue harmonics). Some waveform generators may increase the number of harmonics to reduce the magnitude of perturbations in the waveform. Even when $V_{peak}$ is tens of volts, a superimposed perturbation of a microvolt can affect the second current. A noise signal is composed primarily of bumps and no repeating periods of constant charge velocity or acceleration. Noise with the same $V_{peak}$ as a sinusoidal waveform will deliver more electromagnetic radiation (EMR) than the sinusoidal waveform at 2 Hz. Sinusoidal frequency of a sinusoidal signal, in one example, may be 20 Hz at 2 Vpp, or 10 V at 2 Hz, to provide roughly the same EMR as the 20 Hz signal, without accounting for effects from the radiating body, such as gain and resistance.

When a second current is applied across the first electrode, electrons move across the surface of the first electrode with a net velocity toward the electric field. This material-dependent speed, called "drift velocity," $v_D$, is between about mm/s and about μm/s:

$$v_D = \frac{I}{n * A * Q} \quad \text{(Equation 2)}$$

where I is current (amperes), n is the volumetric charge carrier density in the medium (e$^-$/m$^3$), A is the area of flux (m$^2$), and Q is the charge of the carrier (1.6×10$^{-19}$ C/e$^-$). An electron at a constant velocity has its electric field contracted tangential to the surface of the first electrode, and has its field expanded perpendicular to the surface, per the Liénard generalization. The distortion is negligible if v<<c, as for $v_D$.

Therefore, constant electron velocity from second current is limited on the surface of the first electrode compared to the effects of acceleration. At frequencies below kHz, impedance can be simplified. Ohm's law determines current flow based upon the voltage/time curves of a waveform. For a real-world first electrode, $v_D$ through the first electrode depends heavily upon geometry and, therefore, will be non-uniform across the surface.

Charge produced by electron acceleration propagates across the first electrode relativistically, at close to the speed of light, much faster than VD. Under the AC second current, the average $v_D$ is 0, while the velocity of propagation is approximately:

$$v_P = \frac{c}{\sqrt{k}} \quad \text{(Equation 3)}$$

where k is the dielectric constant of the material in the electrolyte. Since charges move on the surface of the first electrode and not within its bulk, the signal propagation produced by second current moves along the first electrode-electrolyte interface. The dielectric constant of the electrolyte also affects the velocity of propagation. For example, water has a dielectric constant of 80.4; $V_P$ is still 3.35×10$^7$ m/s, dramatically faster than mass transport through the electrolyte.

The power of the EMR of a moving particle can be approximated using Larmor's equation:

$$P_{e-} = \frac{\mu_o * Q^2 * a^2}{6 * \pi * c} \quad \text{(Equation 4)}$$

where $\mu_o$ is the permeability of free space (4π×10$^{-7}$ N/A$^2$) and a is the charge acceleration, a reasonable approximation when drift speed is much slower than the speed of light.

Absent the second current, a charged particle radiates an electromagnetic field, which dissipates with distance, r, from its center as ≥1/r$^2$. In contrast, the electromagnetic field of the same particle in motion dissipates as about 1/r. Thus, the electromagnetic field of electrons under second current is much stronger, per Coulomb's Law:

$$E_r = \frac{q}{4 * \pi * \varepsilon_o * r^2} \text{ and} \quad \text{(Equation 5A)}$$

$$E_\theta = q * \alpha * \frac{\sin(\theta)}{4 * \pi * \varepsilon_o * r * c^2} \quad \text{(Equation 5B)}$$

where $E_r$ is the electric field radial in all directions to the point charge, $E_\theta$ is the electric field which is perpendicular to $E_r$, and $\varepsilon_o$ is the permittivity of free space (8.85×10$^{-12}$ C$^2$/Nm$^2$). $E_\theta$ is unique to charges under acceleration and is responsible for the effects of second current on the electrodeposition. $E_\theta$ is negligible for charged particles at non-relativistic velocity and no acceleration.

EMR depends on the acceleration and not the velocity of the electron, and acceleration depends on frequency of the applied waveform. Equally dependent is the power available at the first electrode/electrolyte interface. The power supplied for sinusoidal second current can be described by:

$$P_{TC} = \frac{1}{2} * R_{peak} * |I_{peak}|^2 = P_{rad} + P_{ohm} \quad \text{(Equation 6)}$$

where $R_{peak}$ and $I_{peak}$ are the peak resistance and current of the waveform, respectively. $P_{TC}$ can be divided into radiated power ($P_{rad}$) and power dissipated due to ohmic losses ($P_{ohm}$).

AC second current increases bulk resistance and channels more power to the surface of the first electrode where the resistance is less. This phenomenon is called the "skin effect":

$$S_D = \sqrt{\frac{1}{\pi * f * \mu * \sigma}} \quad \text{(Equation 7)}$$

where f is the frequency, $\mu$ is the permeability of the electrode, and $\sigma$ is its conductivity. $S_D$ describes the approximate depth from the surface of the first electrode, at which $P_D = P_{TC}/e$. The AC second current, especially at higher frequencies above 1 GHz, more efficiently uses the second current power.

The roughness may exceed the calculated skin depth at ≥1 MHz frequencies. The result of such roughness is a change in the vector of $v_D$ on the first electrode and an attenuation of the EMR traveling according to $v_P$:

$$Y_{RMS} = Y * \left(1 + \left(\frac{2}{\pi}\right) * \tan^{-1}\left(1.4 * \left(\frac{R_{RMS}}{S_D}\right)^2\right)\right) \quad \text{(Equation 8)}$$

where $Y_{RMS}$ is the modified attenuation constant of the electrode due to roughness, Y is the original attenuation constant of the material, and $R_{RMS}$ is the RMS roughness. This relationship under Hammerstad model demonstrates increased attenuation from roughness by unity for the smoothest surfaces and by double for the roughest surfaces. Power dissipation results from micro-field formation between roughness features, and can be absorbed by interfacial electrochemical processes. See also Example 9. With the appropriate waveform, fields from the second current affect the first, secondary, and tertiary electric fields at curvature. The secondary and tertiary electric field cause convective charge transfers. The frequency of the second current may be determined based upon the skin depth of the applied power. Generally, the transverse current causes a more uniform micro-current and macro-current distribution.

EMR occurs at the first electrode/electrolyte interface per $P_{e-}$ and radiates away from the surface per $v_P$. The energy from 0 to some distance, $R_{NF}$, from the interface is both radiative and reactive:

$$R_{NF} \leq 0.62 * \sqrt{\frac{D^3}{\lambda_{TC}}} \quad \text{(Equation 9)}$$

where D is the maximum dimension of the electrochemically active first electrode or the distance between the electrodes applying second current, and $\lambda_{TC}$ is the wavelength of the second current. This region is the reactive near field and within it, $E_\theta$ and $E_r$ are in-phase with the magnetic field of the EMR. As energy interchanges between $\vec{E}$ and $\vec{H}$ every quarter period, the electric fields exhibit capacitive behavior, while the magnetic field exhibits inductive behavior. Within the near field region, electrochemical polarization field lines and any ionic species in the electrolyte reacting with them are subject to these frequency-dependent capacitive and inductive fields.

Another consideration is that the waveform period determines the slew rate and, therefore, the potency of 10 μVpp compared to 10 Vpp (FIG. 9). Without wishing to be bound by theory, the effect of the electric field induced by second current over an area may depend upon the gradient of the field over the area, or the "slew rate," $\Delta V/\Delta x$. (x may be the space or time domain.) Although their peak magnitudes perpendicular to the surface are never the same, a high potential, low frequency waveform may have the same slew rate as a low potential, high frequency waveform at certain points or times, particularly at a bipolar bump. At high frequencies even sinusoidal features may appear asymptotic.

Phase-offset is another controlled variable, which could tune the effect of the second current across the first electrode. For example, two equal, sinusoidal waves phase-offset by 170°-180° mostly cancel each other throughout the signal-generating circuit. The second current power is stronger at rough and/or asymmetrical areas due to less cancellation, having a localized effect on simultaneously occurring electrodeposition. Once deposited material has filled in the abrasion and restored symmetry to the first electrode, the second current power self-cancels. If cancellation increases substantially before surface imperfections have been removed, a larger phase offset may be applied. A benefit of using superimposed signal cancellation reduces the far-field radiating power from the first electrode, compared to a single second current with large power and a complex waveform.

Each component of the devices described herein facilitates charge transfer at different rates. If the AC frequency is too fast, slower processes may be unaffected. Likewise, slower AC frequency does not affect processes which occur over drastically faster periods. Second current frequencies of about Hz and about kHz can affect ionic displacement reactions, such as ionic reactants in the electrolyte. Faster frequencies may alter the cathodic polarization field lines at about the $v_P$, but the reactants move too slowly to respond to those changes simultaneously and will instead respond with some probability, similar to aliasing within telecommunications and computing. Frequencies between about kHz and about MHz are timed to the rotational moment of polar molecules. Above about 100 MHz, many aqueous electrolytes cease to conduct and instead behave capacitively. Arbitrary waveforms, such as superimposing a high frequency waveform over a lower one, balance these effects. Such waveforms can be defined by variables modified during an electrochemical process in response to changes in the system (feedback loop). For example, an adequately enabled oscilloscope may monitor the second current to observe phenomena or gradual changes during an electrochemical process to troubleshoot, refine signals, or give sensory feedback (phase shift, attenuation, etc.).

G. Applications of the Method

The methods described herein may be applied to many electrochemical, metal deposition, and metal bonding applications, including corrosion, electropolishing, and the electrochemical processes within batteries.

1. Corrosion Processes

Most corrosion processes are an unintentional consequence of a material's reactivity with its immediate environment. Boats, oil rigs, and other vessels regularly exposed to saltwater constantly corrode due to localized potential differences. Metals contacting other electrolytes, such as metal tanks storing strong acids, or metal pipes containing mineral-rich water. The metal slowly corrodes into the electrolyte, leading to electrolyte contamination, and structural deterioration of the metal component. Steel frame buildings, ships, oil rigs, tanks, pipes, and other structures with large dimensional aspect ratios can experience an induced potential drop across the surface from electrolyte flow. Potential differences between the metal and electrolyte and potential differences between adjacent metals (Cu, Zn, and Fe) are present regardless of electrolyte movement.

To avoid unwanted corrosion, a negative potential is sometimes applied to the entire structure to maintain the structure at a DC electrical potential below the corrosion potential. This method is referred to as "impressed current cathodic protection", or "ICCP." While ICCP reduces corrosion, its effectiveness is limited by the placement of nearby anodes. The overall effectiveness of ICCP could be enhanced by a method that better distributed charge across a vulnerable surface. Alternatively, in situations when anodes cannot be placed appropriately, a transverse current can be more effective.

By using a method described herein, a second current may reduce corrosion at a junction between two or more galvanically reactive metals (such as Cu wire on Zn-coated Fe in saltwater). No first (deposition) current is used in this example. Under these conditions, the second current can distribute the charge away from grain boundaries on the surface of the first electrode, avoiding corrosive pitting at that surface. See also Example 7.

With few exceptions, linear corrosion, the predictably slow and relatively even loss of material across a surface, is much less about than the accelerated corrosion that occurs in isolated areas due to pitting. The protective properties of any coating are circumvented by a single chink in the armor: Pitting begins at a compromised point in the coating and metal corrodes out from underneath the surrounding intact coating through this single access. As the surface area of the pit grows, the corrosion rate increases and, instead of a slow and even loss, a structurally compromised area is rapidly created. Electrochemical countermeasures do not avoid this process and instead suppress linear corrosion by decreasing the surface voltage at a protected area below the voltage of corrosion. However, the power requirements and effectiveness can vary significantly with fluctuations in the surrounding environment.

Due to these limitations, self-healing coatings that prevent even single chinks are a critical area of development regardless of a coating's other properties. Yet in their chemical formulation the two cannot be separated and effective solutions are inherently case by case and slow to develop. The disclosed process can be deployed with or without surface coatings or conventional electrochemical anti-corrosion systems as necessary to dramatically suppress pitting and suppress the most costly forms of corrosion.

2. Electropolishing

Conventional electropolishing is a type of corrosion process in which a positive potential is applied to a surface to corrode away rough features and render a smoother surface. Advantageously, rough areas corrode faster than smooth. Because conventional electroplating produces unwanted roughness, electropolishing is often used after conventional electroplating to remove accumulated roughness and provide a smooth finish. Electropolishing current densities are usually low and/or pulsed. This maintains a smooth finish at the expense of overall process time. When higher current density is applied, corrosion occurs more rapidly along grain boundaries of the metal, causing chunks of metal to detach from the bulk of the surface and increasing surface roughness.

Instead of allowing unwanted roughness to accumulate in a conventional electroplating process, roughness can be addressed directly with a well-calculated waveform produced for evenness in the z-direction while oscillating the y-direction, or with an AC component using the methods disclosed herein. The goal is to maintain oscillation in the y-direction while controlling or minimizing fluctuations in the z-direction by swinging and changing the magnitude of the vectors. In this way, a flattening of surface features is promoted without vertically building features, as seen in conventional processes. The deposition current is modulated relative to the transverse current to ensure the overall electric field strength relative to the workpiece surface is constant, while the parallel field strength may wander. The first and second currents may be coordinated together so weak and strong field complement. The deposition and transverse currents may pass through the same electrical junction. The total electrode signal may look like pulse plating, but that does not account for the different signals put into the workpiece to generate the disclosed effect. See Example 9.

By using a method described herein, the second current better distributes current. Higher current densities may be run while avoiding the surface corrosion in chunks and along grain boundaries. Electropolishing yields a nearly smooth surface by corroding away the edges and rough features without the spalling seen in prior art methods. A DC field may be applied in the opposite direction of the electric field needed to promote electrodeposition In other words, if the DC field that promotes deposition is negatively polarized relative to the workpiece, then reversing the polarity of that DC field promotes corrosion, thus electropolishing the workpiece. With the methods disclosed herein, electropolishing may be accelerated.

The backside of the workpiece may also be electropolished without a DC offset. A set of deposition electrodes may be arranged on the backside of the workpiece. In a conventional electrodeposition, most of the metal is laid down on the edges facing the void space of the gap. The thinnest amount of material is deposited in the center of the gap, resulting is a poor junction Using the disclosed process, the opposite effect prevails, where corrosion is preferred at the edges but deposition is preferred in the gap. Metal fills in the entire void space.

3. Batteries

Also provided herein are methods for charging an electrochemical cell, such as a battery. These methods suppress and reverse dendritic growth, a common source of failure for most batteries.

Batteries generally comprise repeating units of sources of a counterCharge and first electrode layers separated by an ionically conductive barrier, often a liquid or polymer membrane saturated with an electrolyte. These layers are made to be thin so multiple units can occupy the volume of a battery, increasing the available power of the battery with each stacked unit. As these components become thinner, they also become more fragile. Further, as the electrodes become thinner, a larger ohmic drop occurs across the surface leading to less uniform charge density during charge/discharge cycles.

For example, lithium batteries typically have a metal oxide electrode (M is typically iron, cobalt, manganese), and a carbon electrode coated on metal current collectors. The metal oxide is added to stabilize the lithium metal. The metal oxide electrode starts as $M_xO_y$, and the carbon starts as atomic Li-infused graphite. During discharging (that is, normal use of the battery to provide power to a device), the $Li^+$ ions travel from the carbon through the membrane and intercalate into the $M_xO_y$ to become $LiM_xO_y$. During charging, the $Li^+$ ions follow the opposite path and instead intercalate into the carbon. Under ideal conditions, every $Li^+$ ion finds a vacant $Fe_xO_y$ site or carbon site, and not sites where another $Li^+$ ion has already been absorbed. Problems arise if the $Li^+$ ions try to deposit atop more $Li^+$ and 3D deposits of $Li^0$ form. $Li^0$ aggregation creates an explosion hazard and causes roughness. Specifically, if the $Li^0$ reaches the opposite electrode, the battery may short and the dendrites formed during the Li⁰ deposition may damage the membrane dividing the two half-cells of the battery.

With subsequent charge/discharge cycles the lithium deposits with increased roughness. Lithium-metal batteries (Li-foil anode) and lithium-ion batteries (Li-ions intercalated into a graphite/foil anode, where the foil is frequently copper) both suffer from the growth of lithium dendrites during the battery's charging cycles. While Li-ion anodes can be stable for hundreds of cycles, dendrites develop immediately in Li-metal. Once formed, the dendrites lower the columbic efficiency of the battery, damage the ion membrane, and short the battery if the dendrites contact the anode. Commonly dendrites form which puncture or irreversibly damage the electrolyte membrane. If dendritic growth reaches the opposing electrode, then the battery is permanently shorted and cannot be recovered.

Both types of lithium ion battery form a solid electrolyte interphase at the interface of the anode and electrolyte as the lithium chemically reacts with the electrolyte. The interphase is a layer comprising the insoluble reaction products which collect at the interface. Li ions must pass through the interphase from the anode. Because the interphase generally has a higher impedance, non-uniformity of the solid electrolyte interphase across the anode can cause uneven current distribution across the anode. This unevenness encourages channels to form through the interphase where Li concentration is high. These channels lead the formation of dendrites. Transverse current can enforce a uniform current distribution across the entire surface, more evenly distribute Li concentrations throughout the solid electrolyte interphase, and maintain an anode/electrolyte interface with uniform electrical behavior.

Although this discussion exemplifies lithium-ion batteries (lithium-impregnated into graphite), the methods disclosed herein apply equally to other battery types, including lithium metal batteries and lead acid batteries. Pure lithium metal has a much higher (~5×) energy capacity, but there is no teaching in the art of how to control dendrite growth. These batteries typically last only ten charge-discharge cycles. Failure is instantaneous and more severe than the widely used lithium-ion batteries. The methods described herein control dendrite growth in lithium metal batteries, making these batteries practical and opening the market to batteries with an energy density superior to lithium ion batteries. The method would run every time charge cycle to stymie the formation of dendrites. The electrolytes are selected to allow even deposition of lithium metal during healing process on recharge.

Regarding lead-acid batteries, the methods described herein are modified to account for the configuration of the electrochemical cell and its electrochemistry. Unlike a lithium-based battery, both the anode and the cathode must be recharged. Existing cells have only two ports, so the transverse current must be sent in one port calculated to reflect off the far wall of the cell and back to the port of entry. The waveform of the transverse current would be swept through several frequencies to resonate with dendrites of different sizes on the anode and cathode of the lead acid battery.

As batteries become smaller with increased power capacity these issues have been amplified and pose significant design constraints. The lifetime and performance of batteries with lithium or any other chemistry can be greatly prolonged by increasing the smoothness and uniformity of metal charge carrier species during dissolution and deposition. And the rate of recharge could be increased without compromising the lifetime of the battery as with conventional batteries.

The methods as described herein provide a means of increasing charge homogeneity on electrodes with significant ohmic drop. This reduces thermal gradients and hot spots, which would otherwise cause exothermic battery failure. Further, this would reduce the performance deviations among individual batteries in a stack that occurs as batteries individually age and degrade at different rates. This configuration is different for every battery system type.

II. Device

The present disclosure also provides a device for performing the methods described herein. As shown in FIG. 1A and others, the device 100 comprises a source of a countercharge 120 and a first electrode (e.g., workpiece) 110—although the workpiece is a temporary part of the device. The source of countercharge 120 and the first electrode are 100 in electrical communication through an electrolyte 140. The device 1000 includes a current generation source, such as power supply 160, to induce a first current 130 between the source of a countercharge 120 and the first electrode 110 through the electrolyte 140. The current source includes a connection to the source of a countercharge 120 and the first electrode 110. The current source, or another source, also is connected to the electrode to induce a second current 150, sometimes referred to herein as a "transverse" current, across the first electrode. The second current 150 is transverse or otherwise across the first current 130 at the first electrode 110. The second current 150 is controlled to induce a relativistic charge across the first electrode.

Figure 10:
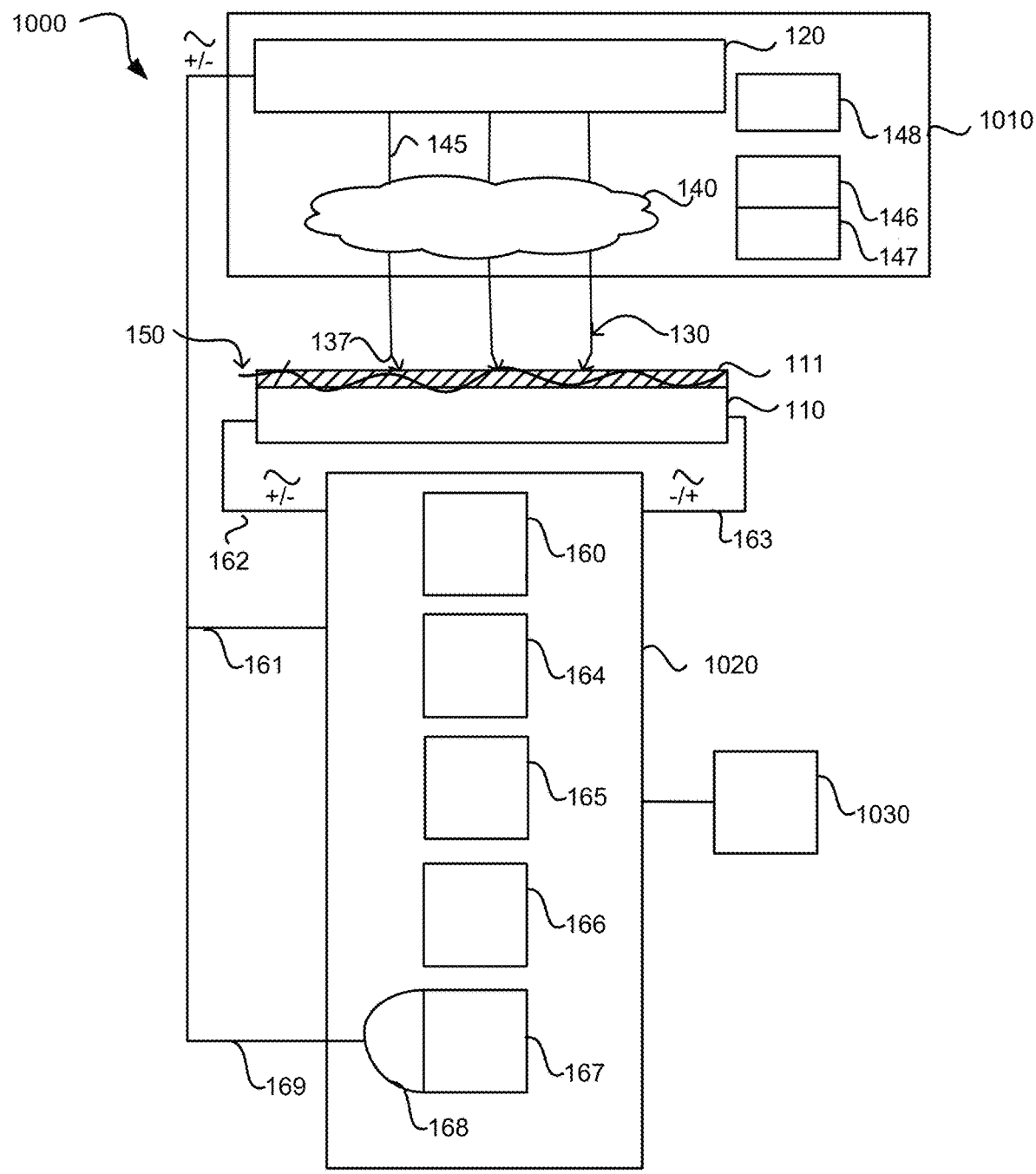
FIG. 10 depicts device 1000 having a main control unit (MCU) 1020 and an electrode applicator unit 1010.

Referring now to FIG. 10, the present disclosure further provides a device 1000 having a main control unit (MCU) 1020 and an electrode applicator unit 1010. The MCU 1020 contains a power supply 160 and a power modulator 165, which induce a first current 130 between the source of a countercharge 120 and the first electrode 110 through the electrolyte 140. The MCU 1020 also supplies power to induce a second current 150 through a surface 111 of the workpiece 110. The electrode applicator unit 1010 contains at least one source of a countercharge 120 and a plurality of channels 145 for flowing an electrolyte 140 through the electrode applicator unit 1010. The electrode applicator unit 1010 is connected to the main control unit 1020 through a current collector cable 161 connected to the main control unit 1020 and a power control unit 1030 connected to the main control unit 1020. The power control unit 1030 applies a first current 130 between a first electrode 110 and the at least one source of a countercharge 120 through the electrolyte 140. The power control unit 1030 may also induce a second current 150 across the first electrode 110. As described elsewhere herein, the second current 150 is transverse to the first current 130, and may be controlled to induce a relativistic charge across the first electrode 110.

The electrolyte 140 need not be contained within a bonding system 1000. The electrolyte 140 may act as a linear resistor. The father the source of countercharge 120 is held from the surface 111 of the workpiece 110, the more resistance passing charge through the electrolyte 140, and the less current density at the workpiece 110. In other instances, the process may be run through a controlled current mode at the power control unit 1030, in which the bonding system 1000 increases the voltage to maintain the selected current density at the surface 111 of the workpiece 100 when the applicator 1010 is moved.

Figure 12A:
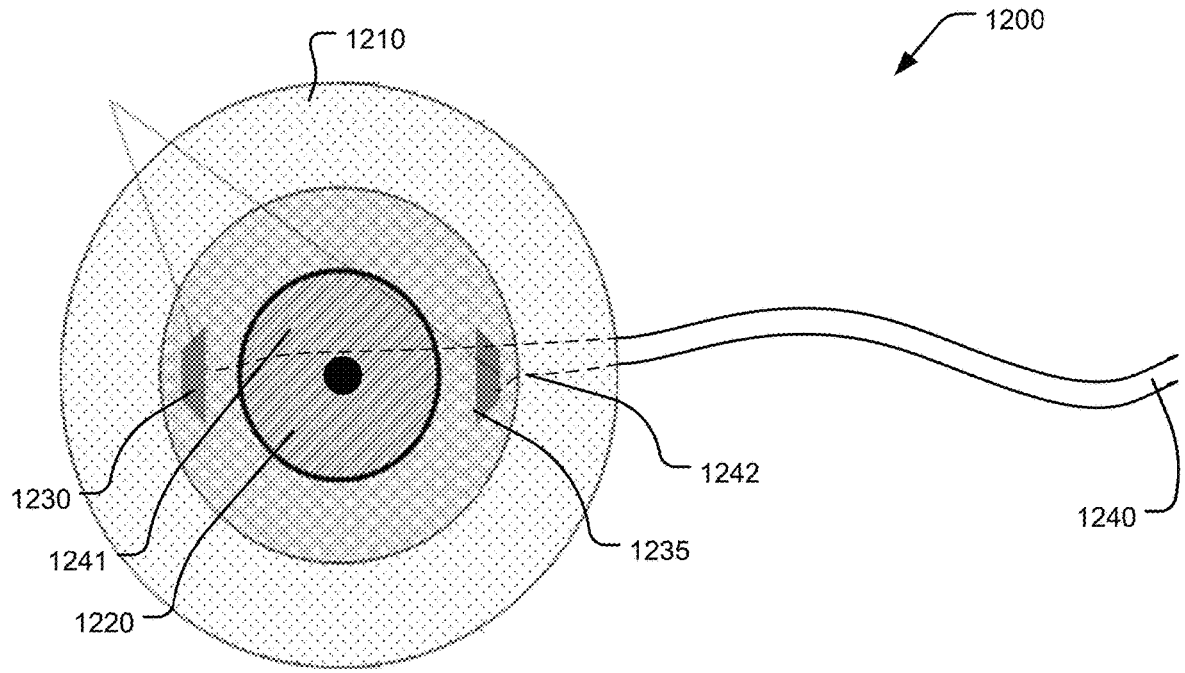
FIGS. 12A and 12B depict a patch-type applicator 1200 from a top view (FIG. 12A) and from a side view (FIG. 12B), as an embodiment of an electrode applicator unit 1010.
Figure 12B:
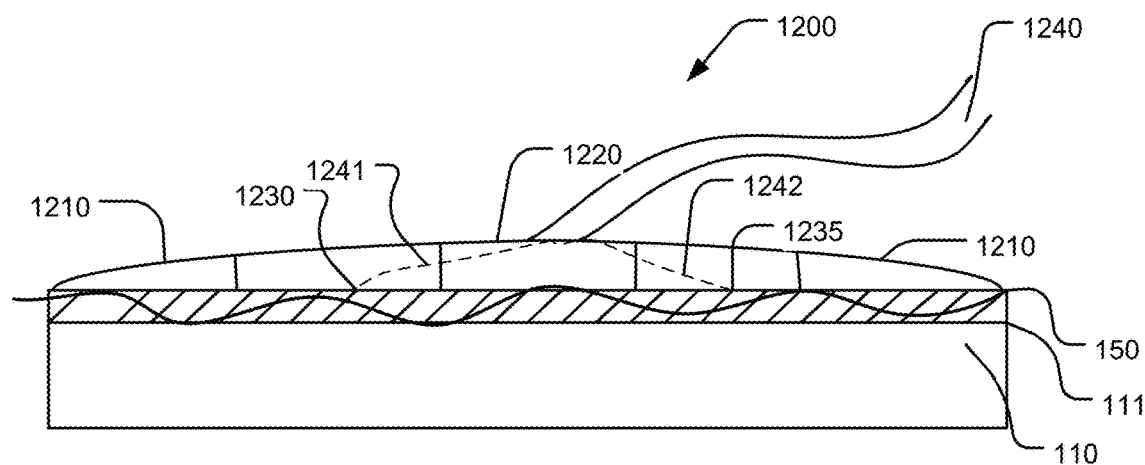
Figure 13:
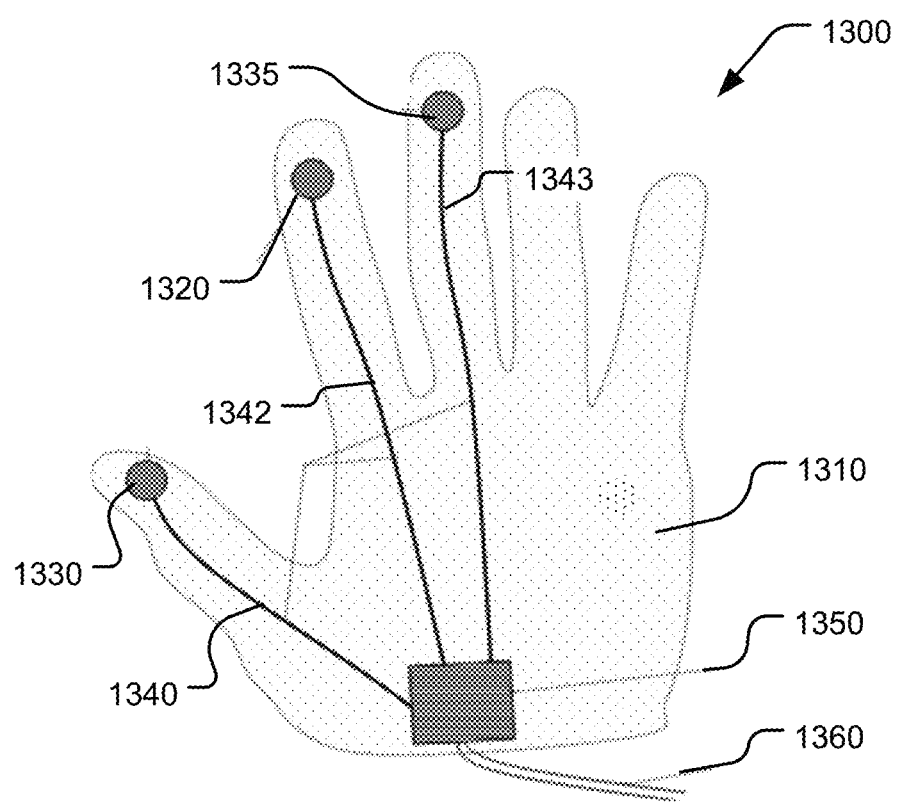
FIG. 13 depicts a glove-type applicator 1300, as an embodiment of an electrode applicator unit 1010.

For a bonding system, one or more applicators 1010 supply new material and supply current to the first electrode, as shown generally at FIG. 10, and in various alternative embodiments at FIGS. 11-13. The applicator 1010 may comprise several contacts for the first current 130 and the second current 150, channels 145 for fluid flow of the electrolyte 140 through the body of the applicator 1010, and auxiliary electrical components. The applicator 1010 may have an integrated heating 146 and/or cooling unit 147, or more generally a temperature control unit, which control the temperature of the electrolyte 140 within. The applicator 1010 and the MCU 1020 may be connected by wiring 161 for power and sensors, and tubing 169 that allows fluid to flow from one to the other.

The device 1000 may further comprise a current collector cable 161 connected to the MCU 1020 via wiring, with leads for attaching to the first electrode. Under operating conditions, the substrate 110 becomes the working electrode.

The device 1000 may further comprise a power control unit 1100, which supplies power for the first current 130 and the second current 150.

The devices may use any electrolyte described herein. The electrolyte 140 may be stored in a tank 167 or other form of container, which may be integrated or removable. When present, the tank 167 supplies the electrolyte 140 to the applicator 1010. A pump 168, depending on the configuration, may be positioned to drive or otherwise pump electrolyte 140 from the tank 167 through the tubing 169 to circulate electrolyte 140 for distribution on the workpiece where desired. In such a configuration, the electrolyte 140 may be dispensed through the applicator 1010.

A. Main Control Unit

Referring to FIG. 10, the main control unit (MCU) 1020 may house a power supply 160, a processor or other compute components in communication with a memory or other tangible storage medium including software 164 forming executable instructions or control sequences, a computer-controlled power modulator 165, and auxiliary electronics 166. In the main control unit 1020, the processor 164 is configured to execute the instructions stored on the computer readable medium. The power modulator 165 and the power supply 160 may be controlled by the processor 164.

The MCU 1020 may include one or more additional electrical components, such as a first control system, power generation subsystem for deposition/corrosion, power generation subsystem for the second current, and sensor-based feedback subsystems. When present, the first control system accepts user input for the chemistry and operating conditions and to control the subsystems to provide power for first and second currents. The first control system may be digital for complex systems, or analogue for simple systems with fewer chemistry requirements. Computer control may be used for the broadest range of materials, sensory feedback, data recording, and complex deposition conditions.

The deposition power subsystem must have stable mA and mV control with low internal reflection. The subsystem may provide DC and AC power between about 1 Hz and about 1 kHz. The subsystem may be programmable to apply voltages relative to sensor input from a sensor subsystem. The current may range between about 0 mA/cm$^2$ and about 200 mA/cm$^2$ per channel relative to the area of the first electrode for an application. The current may also range between about 0 mA/cm$^2$ and about 300 mA/cm$^2$ per channel relative to the area of the first electrode for an application. Multiple channels and/or fast switching may be used when needed, such as when joining two portions of a first electrode, or when the MCU 1020 controls bonding at multiple areas.

The deposition power subsystem may apply power with modulated first current. Current-controlled power may achieve a current density (A/cm$^2$), and so a desired mass flux from metal of the electrolyte onto the surface of the first electrode. Potential-controlled power may achieve a redox state of substrate atoms at the first electrode/electrolyte interface. For example, a slightly negative potential could be applied to the first electrode to ensure a metallic state of the surface atoms and to prepare the surface for adhesion. Potential control of positive polarity at the first electrode may corrode the surface of the first electrode. For example, the MCU 1020 could effect a potential equal to or greater than 0.8 V but below 1.6 V vs. a standard hydrogen electrode (SHE) to corrode a steel surface without corrosively pitting. This would be useful for increasing the penetration depth of deposited layers on the surface of the first electrode without causing significant roughening. Potential control may also control the stoichiometry of deposited alloys or composites via potentials of the first current of based on the metal from the electrolyte.

For example, in an ionic liquid electrolyte containing both Fe and Mn species, the MCU could effect a potential of −0.3 V vs. Fe/Fe$^+$ for 2 s followed by −0.9 V vs. Fe/Fe$^+$ for 2 s. The first potential surpasses the activation energy for Fe to deposit, but is insufficient to drive Mn deposition. The second potential exceeds the activation energy of Mn$^\circ$ formation and so both species electrodeposit simultaneously. The overpotential (that is, the potential applied in excess of the activation energy) impacts the relative deposition rate of each species. Other alloys may be used by changing the metal species and selecting the appropriate voltage, as taught herein. See the FeZn alloy at Example 13.

The MCU 1020 can apply DC or AC and obtain feedback measurements which allow the computer to modulate outputs. For example, the power control unit (PCU) 1030 might operate in a DC mode to measure the open circuit potential (OCP) between the first electrode 110 and source of a countercharge 120 so potentials may be applied relative to the OCP. The MCU 1020 can also use DC current to measure dynamic capacitance of the electrochemical double layer at the surface of the first electrode. Because the double layer capacitance may proportionately indicate changes in the surface area 111 of the first electrode 110 during operation, such a reading may allow the MCU 1020 to alter the second current 150 or to maintain the current density (A/cm$^2$) specified as new material is added to the first electrode 110. AC can be applied by the MCU 1020 to obtain resistance/impedance measurements. For example, the MCU 1020 can rapidly apply an AC of 1-100 mV and a frequency less than or about 100 kHz to measure the linear impedance response and obtain feedback about the bulk conductivity of the first circuit. If a reference electrode 148 is present in the applicator 1020, additional lower frequencies can monitor the first electrode/electrolyte interface.

The MCU 1020 may periodically interject these modifications into a deposition sequence to obtain feedback. The computer 164 may compare this feedback to models and user-specified operating parameters to modulate the applied power driving deposition and second current.

For example, after 1,000 corrosion/deposition pulse iterations (or every several seconds), the MCU 1020 may superimpose a 10-mV, 500-kHz sinusoidal AC wave onto the DC potential of the preceding pulse of the first current 130 to measure system impedance. The measurement time would depend on the frequency and the number of wave periods recorded and the processing time for the computer to analyze the recorded signal against the applied waveform (~10-50 μs total). If impedance has increased relative to the last data point collected, the computer 164 may determine whether this increase correlates with an expected gradual loss in ionic conductivity of the electrolyte with use and time. If so, the current/potential magnitude of later pulses may be increased to overcome the additional ionic resistance of the electrolyte 140. The entire sequence may be repeated using updated parameters. If not, then the MCU 1020 measures impedance/capacitance at one or two lower frequencies to probe the condition of the surface. And immediately after the user turns on the power, and again immediately after power is turned off, the MCU 1020 may measure the OCP of the system to estimate the redox state of the first electrode surface 111.

When present the second current power subsystem may have multiple channels with variable output impedance, wideband frequency range (0-GHz), DC offset capability, and waveform generation. Internal amplification and attenuation enables an MCU for larger work areas and may apply μV or smaller perturbations. Separate channels may modulate their output signal relative to one another.

Sensor power subsystems, when present, may allow for processing of feedback/feedforward from electrodes for parameters such as reference, pH, conductivity, signal impedance and attenuation, and whether or not an electrode is contacting the surface of the first electrode. They must also process feedback from temperature sensors and provide power for tip chamber heating when needed. These systems provide feedback to the first control system so it can modulate deposition and second current circuits.

The MCU 1020 may have an onboard interface, or connect to external computers for programming through separate software. Any device described herein may also further comprise a signal canceler to reduce a far-field radiation from the first electrode.

B. Applicator

Referring now to FIGS. 10-13, many designs can be used for the electrode applicator unit 1010 (FIG. 10), including a gun-type applicator (FIG. 11), a patch-type applicator 1200 (FIG. 12), or a glove-type applicator 1300 (FIG. 13). Generally, the applicator 1010 may comprise at least one ionic contact with the first electrode 110 via a complete circuit 130 between the source of a countercharge 120 and electrolyte 140. Many variations are envisioned within this general design, including, but not limited to, one or more points of electrical (non-ionic) contact, such as two or more points of contract, with the first electrode 110 in spatial proximity to the point of electrical contact, a reservoir 167 of enough volume to contain and dispense electrolyte, a corroding electrode, a source of a countercharge 120, a reference electrode (RE) 148, and a longitudinal receiving antenna that would allow for z-axis amplitude electromagnetic inputs and feedback modifications for the second current 150 applied for smoothing or resolution of other structural abnormalities resulting from the process. Other process may use one point of contact, especially a high frequencies.

Figures 11A, 11B:
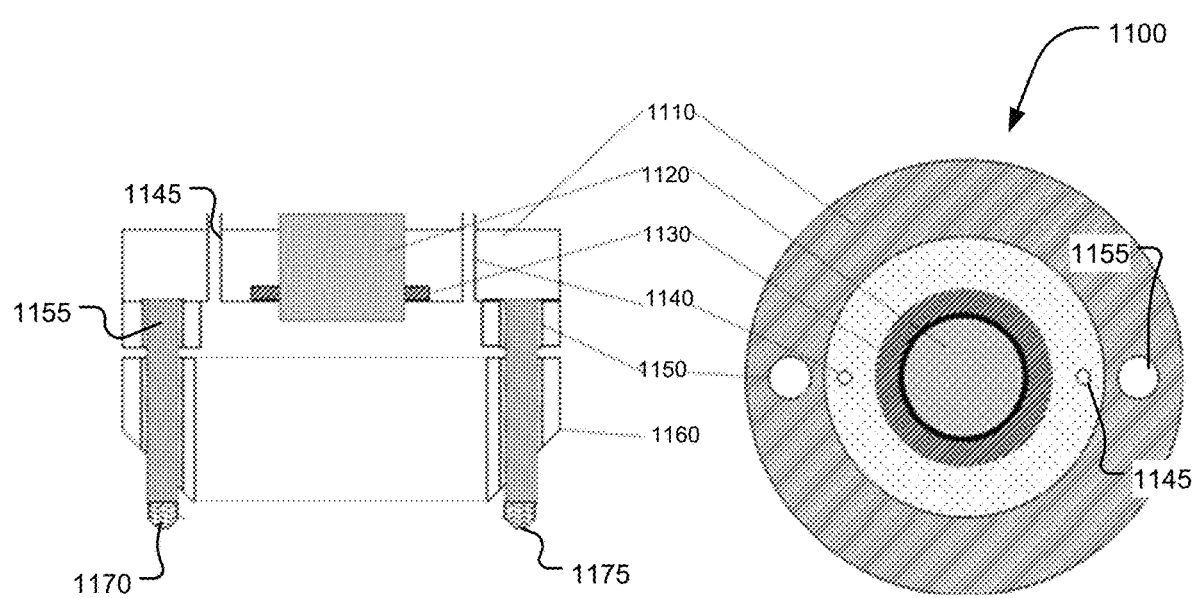
FIGS. 11A and 11B depict a gun or wand type applicator 1100 from a representative section view (FIG. 11A) and from a top view (FIG. 11B), as an embodiment of an electrode applicator unit 1010.

Gun or wand applicators may have an application system similar to that shown in a representative section view at FIG. 11A and a top view at FIG. 11B The base 1110 of the applicator 1100 may have a feedthrough for a corroding electrode, or a seat for an interchangeable non-corroding source of a countercharge 1120. Any corroding electrode described here may be used. The seal electrically polarizes the first electrode. The seal defined one point of contact so far as the circuit is concerned, even though the geometry of the contact encloses a large area. The base 1100 may also have an electrode 1130 separate from 1120. Electrode 1130 may be a parallel source of a countercharge to modify or stabilize the total first current without changing the potential through the source of a countercharge 1120. In this way co-deposition may be controlled independently of the overall deposition process.

If a reverse pulse deposition process or corrosion of the first electrode is chosen, then electrode 1130 may be a cathode so reduction on the source for a countercharge 1120 is not mandatory. Electrode 1130 may instead be a reference electrode (e.g. 148 in FIG. 10), or a separate reference electrode may be placed in a similar location on the applicator 1100. Electrode 1130 may be a single surface, or multiple surfaces with directional control. Electrolyte may be circulated through the system via one or multiple, opposing channels 1140, 1145. The applicator 1100 may contain one or more channels 1150, 1155 for fresh and depleted electrolyte.

The applicator 1100 may contain two sources of countercharge 1120, which contact the first electrode via the tip 1160, inducing a second current across the first electrode. The sources of countercharge 1120 electrically contact the first electrode through caps 1170, 1175. The caps 1170, 1175 may comprise carbon or soft metal pads, or harder metal pins when it is desirable to increase localized current density of the second current.

Flow and electrode geometry inside the applicator 1100 may be two-dimensionally symmetric. Alternatively, the flow pattern may include a electrolyte influx down the center of the applicator, to the tip 1160, followed by outflux along the outer perimeter of the applicator 1100.

The interchangeable tip 1160 provides space for the electrolyte. The tip 1160 may have a sealing material around its opening to isolate the electrolyte from the channels 1150, 1155 when in contact with a surface. The channels 1150, 1155 may be used with or without separate leads identically polarized and connected to the first electrode. The caps 1170, 1175 may isolate the electrolyte from oxygen and moisture.

The tip 1160 of a gun or wand applicator 1100 may be fixed or removable. Primarily, the area and geometry of the opening of the tip 1160 would determine the surface area of the first electrode contacted, and therefore the area onto which new material is electrodeposited. Secondarily, the area and geometry of the tip 1160 may exploit surface tension of the electrolyte to influence fluid from draining from the aperture when the tip volume is full. The tip 1660 or applicator 1100 body may contain an agitator for the electrolyte, including higher frequency ultrasonic transducers, low frequency vibrators, or any related mechanism. The tip may be designed for directional use. A scoop-like tip may use sheering force of the first electrode surface to push electrolyte back into the applicator as the tip is guided across the surface of the first electrode.

The base or tip may house a chemically resistant thermocouple or thermal resistor (thermistor) to monitor heat flux near the surface of the first electrode. The tip may be constructed of a semi-flexible material to facilitate consistent contact against non-planar surfaces and to provide a seal against excess electrolyte leaving the boundary of the tip opening. Fluid behavior at this junction may also be controlled by selecting the viscosity of the electrolyte and the diameter of the tip aperture to constrain the electrolyte.

The tip may contain a dielectric mesh, which contacts the surface of the first electrode to distribute the second current by minimizing energy absorption by the electrolyte at hot spots. The dielectric mesh may be a metal mesh, a metal mesh in a polymer, or a dielectric polymer mesh. When present, a metal inner later provides a conductive surface for capacitive coupling of the radio frequency originating from the workpiece. The metal inner layer is also an effective ground plane, while the polymer outer layer protects the metal inner layer from depositing or corroding.

When present, the mesh may be have a porosity between about 1 mm and about 1 µm, to avoid any slowing of mass transport between the electrolyte and the surface of the first electrode. The mesh may also have openings, such as a slits can be oriented over a junction or gap in the first electrodes. The material of the source for a countercharge may closely match the material composition of the first electrode.

Referring to FIGS. 10 and 11, the tip 1160 may contain a reference electrode (RE) 148 of the $1^{st}$ or $2^{nd}$ kind. Short, single data point feedback measurements using the RE may use an RE of the $1^{st}$ kind (RE1) may comprise noble metals, Pt, Pd, Au, Ag, or others. With these reference electrodes, fast potential measurements may be recorded while the surface state of the RE is relatively stable. Polarization of the RE over longer time domains would allow the measured feedback potential to drift as the RE1 surface conditions become more transient. To obtain feedback over longer periods, an RE2 should maintain a steady-state potential while continuously polarized in solution. An example RE2 would be Ag/AgCl.

With a patch-type applicator 1200, referring to FIGS. 10, 12A and 12B, new metal deposition can be achieved by adhering the patch 1200 over the area of the first electrode 110 to which new metal will be deposited. The patch may have an adhesive or magnetic area 1210 by which to attach to a first electrode 110. At the center of the patch may be an inset, electrochemically active area 1220, composed of a conductive back layer, such as a metal foil. In various embodiments, this back layer may be a corroding or non-corroding electrode, which provides a source of a countercharge 120. The remaining volume of the inset may be filled with electrolyte 140. The electrolyte 140 may be of high viscosity, such as a gel, or be of low viscosity within a sponge or porous membrane. Any electrolyte described herein may be used. The perimeter of active area 1220 may have a contiguous seal made of silicone, latex, or similar material. This seal, when present, may isolate the electrolyte 140 from auxiliary contact pads 1230, 1235, which provide electrical contact with the first electrode 110.

Two contacts pads 1230, 1235 are shown at FIGS. 12A and 12B, more may be used in any orientation around the active area 1220. The pads 1230, 1235 provide first current 130 to the electrochemically active area 1220 of the first electrode 110 and second current 150 across the area of treatment. The patch 1200 may be as long as desired or of any geometry so the electrochemical process can occur over a larger area at one time. Power may be provided to the patch through a cable 1240, which may lead to a power supply/control unit 1030, or the patch 1200 may be powered by an onboard battery and simple control circuit. Leads 1241, 1242 connect the cable 1240 to pads 1230, 1235. A single electrical contact point touching the surface may also be used.

Referring now to FIG. 13, the applicator 1300 may be integrated into a wearable glove 1310, permitting tactile sensory feedback with manual articulation. Corroding or non-corroding source of a countercharges may be seated into the first electrode holder 1320, or the entire tip of the digit may provide a source of a countercharge. Similar sources of countercharge 1330, 1335 may be on the tips of the nearest digits. The first circuit is completed between the first electrode holder 1320, the first electrode, and the sources of countercharge 1330, 1335, while the second circuit is completed through the sources of countercharge 1330, 1335 and the first electrode. Each circuit may be powered by wires 1340, 1342, 1343 leading to a junction or gap 1350, which is connected to a wire 1360 leading to a power supply/control unit, or an onboard battery/control system. The user can articulate the first electrode holder 1320 to control the area of deposition while changing the relative positions of the sources of countercharge 1330, 1335 to control the vector of second current. Other digits or multiple gloves may be used.

In the configurations, he applicator 1010 may further comprise a heating unit 146 or a cooling unit 147. Theses unites 146,147 modulate the temperatures of the electrolyte 130 within the channels 145 of the electrode applicator unit 1010.

III. Software

The present disclosure further encompasses software for operating devices described herein and for performing methods described herein.

For example, the MCU may be programmed to use common materials such as steel, Cu, Ni and Zn with the appropriate electrolyte for each material. The MCU may be modified with enhanced programming to modulate the efficient electrodeposition of more complex alloys and composites.

The MCU may have wired or wireless networking or computer-linking connectivity. These connections may load sensor data logs to a computer readable medium. The connections may facilitate computer control during operation of the method, live remote monitoring, and communication between multiple MCUs. The connections may receive software updates, including operating parameters and models for different substrate materials and electrolytes. For example, party A may create a electrolyte with special operating parameters and create a computer model that can be loaded onto the MCUs for other users.

The software may allow the MCU to control the deposition and second current functions during operation within minimal input from the user. Parameters may be initially entered into the MCU, or changing periodically to refine the process, so user feedback during operating is largely limited to starting and stopping the process.

IV. Metal Deposits

The present disclosure also provides amorphous metal deposits formed by electrodeposition. The metal deposits may also exhibit one crystal plane more often than other crystal planes An adlayer may be deposited onto the workpiece to promote adhesion for the metal deposit. "Adatoms" have not given up all the electrons for form a full bond. Rather, the atoms slide around until they hit new layers, promoting layer-by-layer growth. The methods described herein are not just top-down deposition of new material but promote self-leveling atoms.

Grain size may be modulated by selecting deposition speed. Generally, a slower deposition results in larger grain sizes and a faster deposition in smaller grain sizes. A gradient may also be imposed across the workpiece so that the deposition in one region is thicker and is at the other end of the gradient the deposition is thinner.

The present disclosure also provides methods for plating on the semi-conductive and non-conductive workpieces, such as carbon-fiber weave and Kevlar™ fabric. Carbon-fiber is minimally conductive, but can be directly metallized with the methods described herein. Other fabrics, such as Kevlar™, may be treated before metallization by impregnating with metal ions. Any woven material is suitable. For example, a cotton cloth may be impregnated with $NiCl_2$ overnight. Fabrics may be straight, stiff, and/or distribute stress forces. Generally, metallization replaces conventional epoxy treatment.

For example, a bike may use a carbon fiber frame metallized with aluminum. Flex may be defined in the frame. The shape of the carbon fiber enables a range shapes and weight load distributions.

In another example, body armor may be formed from one or more metalized layers of a paraphenylene terephthalamide (para-aramid) fiber, such as Dupont™ Kevlar®. Conventional body armor requires instead of the conventional 7 to 9 layers of Kevlar® to meet ballistics requirements. Even while accounting for the added weight of the metallization, the new body armor is thinner and lighter, allowing longer durations of comfortable wear. To armor vehicles, the Kevlar® may be shaped into panels and metalized to form the body of the vehicle. Again, like body armor, the vehicle paneling is thinner and lighter while providing equivalent protection from projectiles and other weapons.

EXAMPLES

The following symbols and abbreviations are used throughout the present disclosure:
∂ Average diffusion layer thickness of reactive species in electrolyte
A Area of flux ($m^2$)
AC Alternating current
c Speed of light ($3 \times 10^8$ m/s)
CA Corroding Source of a countercharge
D Longest EMR-active dimension of an electrode (m)
DC Direct current
$\vec{E}$ Electric field vector
$E_{ED}$ Electric field induced by an electrodeposition between a source of a countercharge and a first electrode (V/m)
EMIC 1-Ethyl-3-methylimidazolium chloride
EMR Electromagnetic radiation
$E_r$ Electric field radial to a point charge
$E_{TC}$ Electric field induced by second current (V/m)
$E_\theta$ Electric field perpendicular to $E_r$
$\varepsilon_o$ Permittivity of free space ($8.85 \times 10^{-12}$ $C^2/Nm^2$)
f Frequency
$F_{DP}$ Dielectrophoretic force
$F_{EP}$ Electrophoretic force
$\vec{H}$ Magnetic field vector
$H_{sine}$ Amplitude of a sinusoidal profile use to approximate surface roughness
I Current (amperes)
i(x) Current at point x on the electrode surface
$i_{ave}$ Average current density along a rough surface
$i_H$ Current density at the highest features of roughness
$i_L$ Current density at the lowest features of roughness
$I_{peak}$ Peak current
Ipp Peak to peak current of a waveform
$I_{RMS}$ RMS Current
k Dielectric constant of a material
k $2\pi/\lambda$
MCU Main Control Unit
n Volumetric charge carrier density (e–/$m^3$)
OCP Open circuit potential
PCU Power Control Unit
$P_D$ Power at a depth, D, from the electrode surface
Pe– Radiative power of a non-relativistic, accelerating electron
$P_{ohm}$ Power dissipated by ohmic losses
$P_{rad}$ Radiated power
$P_{TC}$ Applied power of second current
Q Charge of an electron (1.6 $10^{-19}$ C/e–)
$R_{CT}$ Charge transfer resistance of an electrochemical reaction
RE Reference Electrode
$R_{NF}$ Distance of the reactive near field from an electrode surface
$R_{peak}$ Peak resistance
$R_{RMS}$ RMS roughness of an electrode surface
$R_S$ Solution (electrolyte) resistance
RTIL Room Temperature ionic liquid
$S_D$ Skin depth
SHE Standard Hydrogen Electrode
TC Second current
v Velocity of charged particle
V Voltage
$v_D$ Drift velocity of a charged particle
$v_P$ Velocity of propagation
$V_{peak}$ Maximum voltage of a waveform
Vpp Peak to peak voltage of a waveform
$V_{RMS}$ RMS Voltage
$V_{TC}$ Voltage of second current
Y Material attenuation constant of second current
$Y_{RMS}$ Attenuation constant of second current due to surface roughness
α Charge acceleration
γ Liénard electric field contraction constant
λ Wavelength
$\lambda_{TC}$ Wavelength of second current
μ Permeability of electrode
$\mu_o$ Permeability of free space ($4\pi \times 10^{-7}$ $N/A^2$)

Example 1—Smoothness and Uniformity Through Controlled Charge Distribution

This example demonstrates how charge density increases at surface curvature or irregularity. To measure this effect, matching substrates were processed using conventional electrodeposition or under the disclosed method. The substrates were then compared to each other.

Figure 14A:
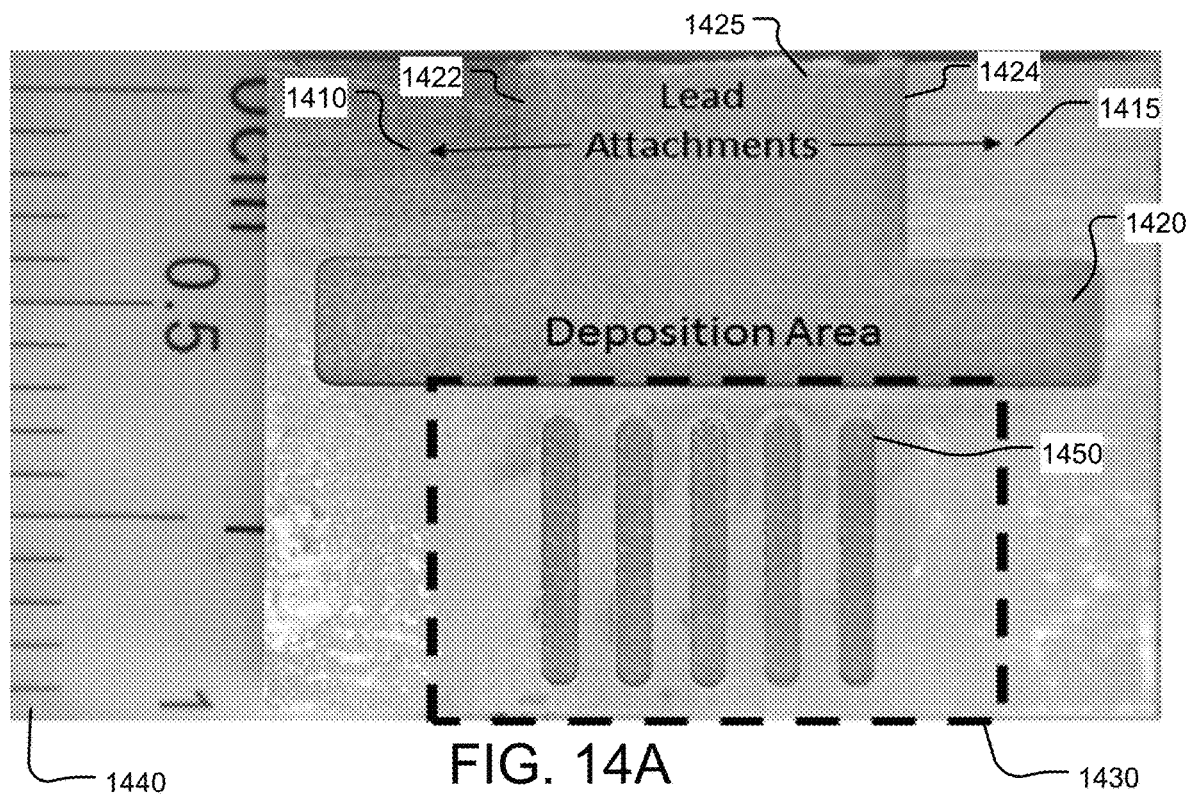
FIGS. 14A and 14B depicts a deposition from a saturated CuSO$_4$(aq) at 25° C., 30 mA/cm$^2$. Specifically, FIG. 14A was conducted without a second current; that is, a conventional electrodeposition).
Figure 14B:
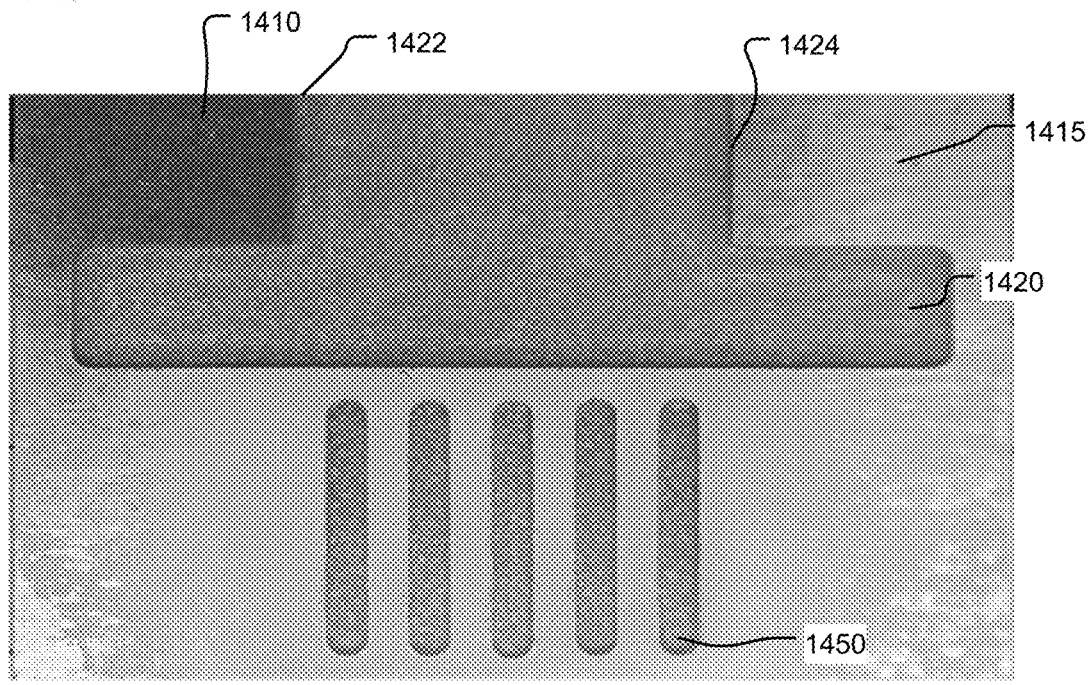

Referring first to FIGS. 14A & 14B, two 15 mm×18 mm copper electrodes were machined from an FR1 circuit board (a thin layer of copper over a non-conductive phenolic resin) with two lead attachments 1410, 1420, a deposition area 1420, and five 0.8-mm wide slots 1450. Lead attachment 1410 was on a first side 1422 of the slots 1450. A second lead attachment 1415 was on a second side 1421 of the slots 1450. Slots 1450 functioned as voids in the workpiece, so that current flow was blocked with a potential drop on either side of the slot 1450.

FIG. 14A shows the results of electrodeposition of copper at 30 mA/$cm^2$ without a second current; that is, under conventional electrodeposition. Darker areas 1425 developed toward the top of the deposition area 1420 where charge built up. These darker areas are due to a rougher deposit of copper and an increase in copper oxide.

FIG. 14B shows another workpiece resulting from the electrodeposition of copper at 30 mA/$cm^2$ with a second current of 5 MHz at 10 Volts peak-to-peak (Vpp) applied between a lead attachments 1410, 1415. The same electrodeposition conditions were used in FIG. 14B as in FIG. 14A, but this time with the second current applied across the workpiece, with the attributes of the current as introduced immediately above.

Figure 15A:
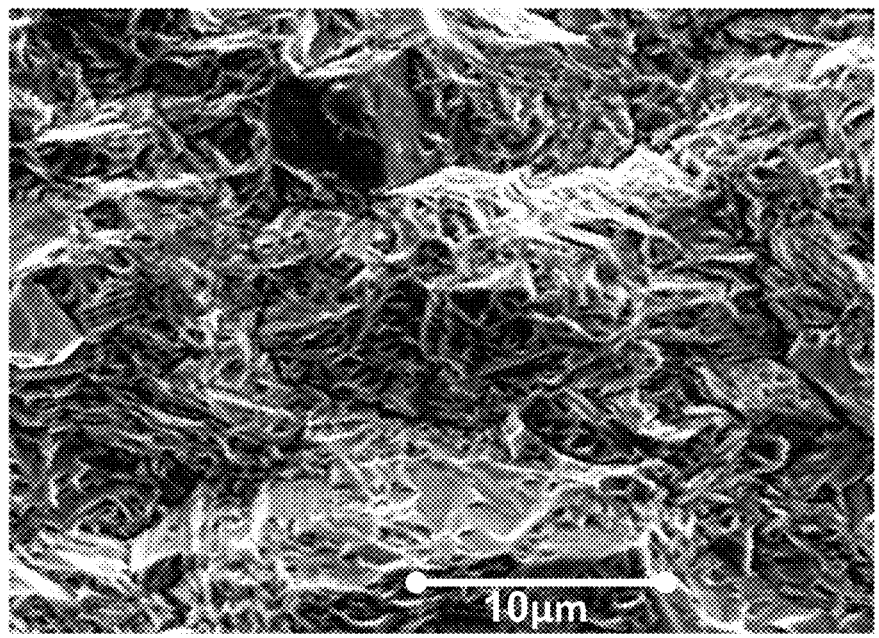
FIGS. 15A and 15B depict a deposition of copper from 1.25 M $CuSO_4$(aq) electrolyte at 25° C. and 15 mA/cm$^2$ for 1 hour. Specifically, in FIG. 15A no second current was applied; that is, it was a conventional electrodeposition. At FIG. 15B a second current of 1 MHz at 27 dbm (50Ω) was applied.
Figure 15B:
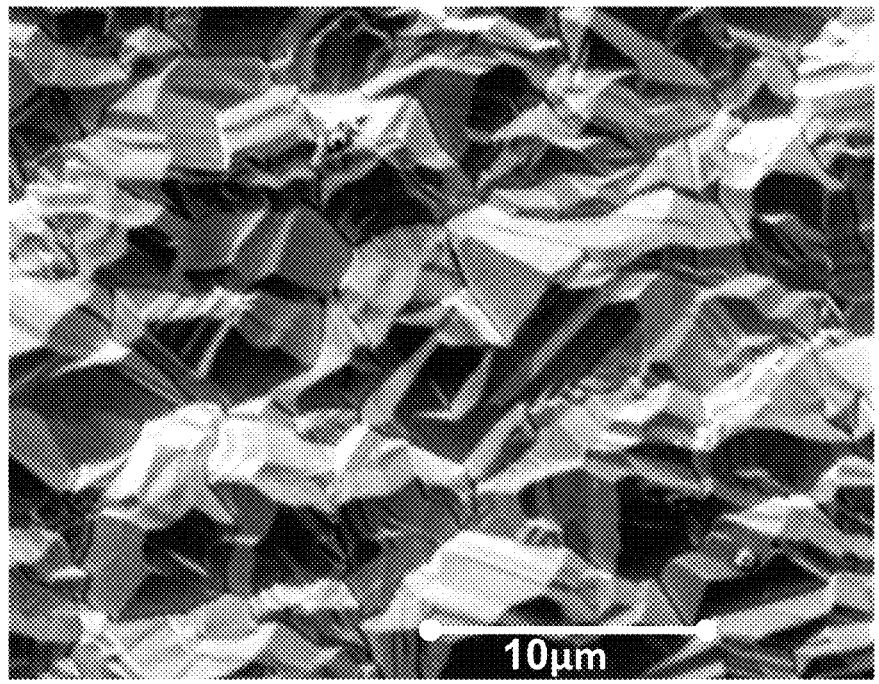

A comparison at the microscopic level of copper growth with and without second current is shown in FIGS. 15A and 15B. FIG. 15A depicts an electron micrograph of a deposit formed from a 1.25 M $CuSO_4$(aq) using conventional deposition. This electron micrograph showed rough growth at the surface, in which scattered the electron beam from the microscope. Porous edges grew outward, while voids were simultaneously filled in. The growth seen in FIG. 15A resulted from kinetic roughening and occurred when the nucleation rate was high relative to the actual growth rate. At longer deposition periods, these edges propagated faster than the voids were filled, leading to more dendritic morphology.

FIG. 15B depicts an electron micrograph of a deposit formed when a second current of −27 dbm at 1 MHz was applied to the workpiece under the same conditions as FIG. 15A. For ease of comparison, FIGS. 15A and 15B were set with the same size scale. All measurable porosity disappeared on the surface and the growth proceeded with limited nucleation (non-dendritic growth) followed by two-dimensional surface completion. When the parameters were slightly different, the opposite effect was observed. Also in FIG. 15B, the current efficiency of deposition remained unaltered by the second current. The second current lowered the nucleation rate while the overall rate of growth remained consistent as two-dimensional expansion. The electric field of second current increased the surface diffusion rate of adsorbed metal instead of immediate nucleation with complete charge transfer. Therefore, the entropy of the surface was lower than normal. The degree of crystallinity can be controlled by modulating the second current to achieve the desired deposit properties.

Conventionally, irregularities are managed with slower deposition current densities, chemical additives (levelers/brighteners), large electroplating baths, or anodes on all sides. Applying a second current instead provided a simple means to reduce reliance on or avoid these conventional practices. The uniform distribution of charge afforded by second current reduced the disproportionate growth normally observed at edges and points. Consequently, the uniformity of growth became less dependent upon the relative position of an anode.

By inducing high frequency movement of the electrons on the surface of the first electrode under the methods used in FIGS. 14B and 15B, the charge was more evenly distributed across the surface than using conventional electrodeposition in FIGS. 14A and 15A, resulting in uniform deposit across the entire surface of the workpiece. The surface-distributed charge arose from multiple mechanisms operating together. On average, the electrode was uniformly polarized, which led to a uniform concentration distribution of reactant species near the surface.

Adhesion of electrodeposited metal was challenging because native oxide layers form on metal surfaces in the presence of oxygen or moisture. These layers are conventionally removed using strong acids to etch the metal surface before new metal is deposited without allowing significant oxygen to enter the system at any point. Mechanically strong bond formation is a higher energy process. This is part of the reason deposited layers can grow on a substrate only to be easily peeled off later, and why the edges of two first electrodes may grow together with deposition but fall apart upon later handling.

By using electrolyte chemistry that supported reversible or semi-reversible corrosion, treatment with strong acids was avoided by first corroding the surface oxide layer into solution to expose bare metal at the surface of the first electrode. Corrosion-based surface exposure may be performed with the first current between the first electrode and a source for a countercharge, or independently of a source for a countercharge with just the second current running through the first electrode.

Figure 16:
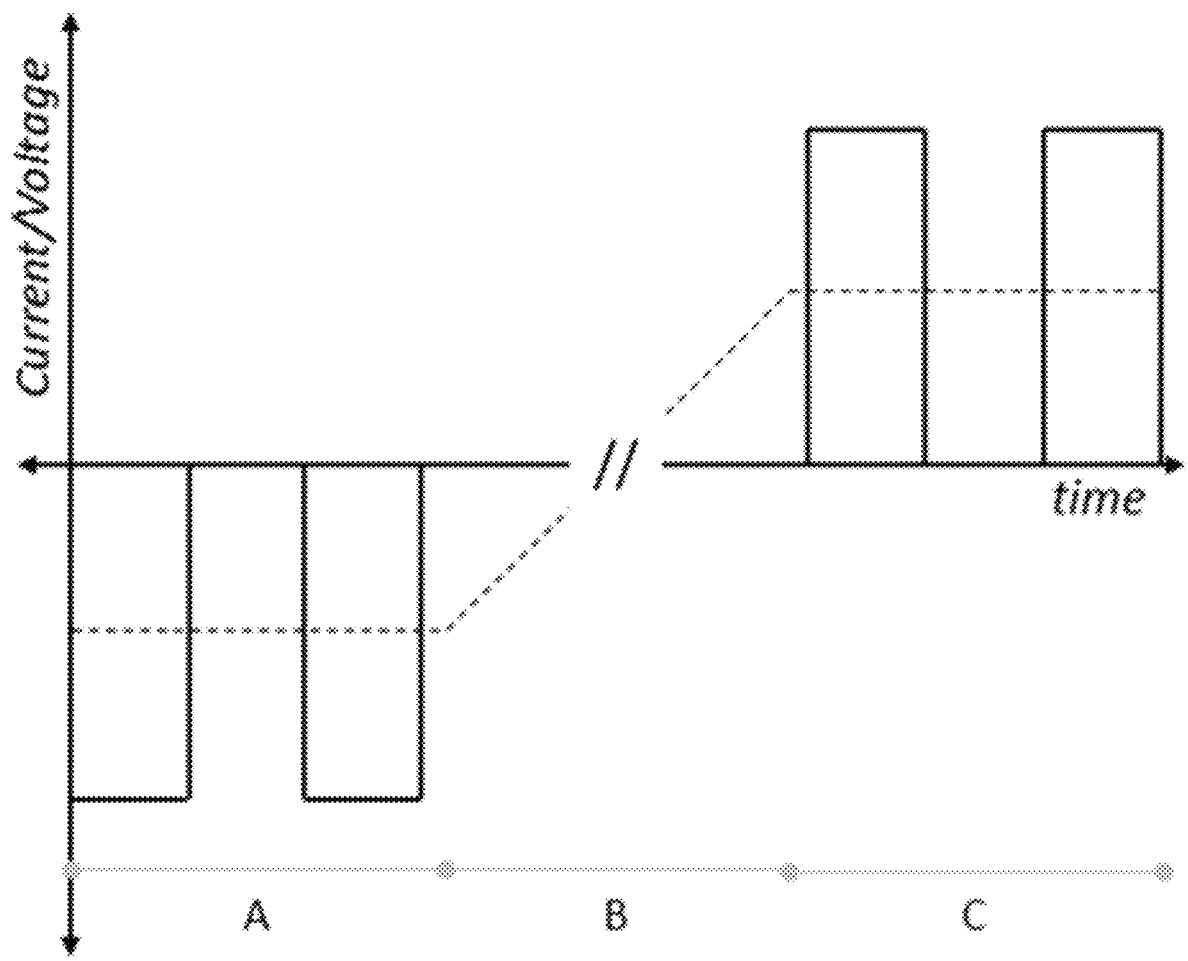
FIG. 16 depicts an electrochemical circuit pulsed adhesion scheme, which may be performed without a second current.

Superior adhesion of a metal onto a substrate was also obtained without conventional surface pre-treatments using DC or alternating AC/pulse corrosion first currents, shown in FIG. 16. During Period A, the pulses alternated between neutral and corrosion-inducing potentials. Corrosion at ≥100 $mA/cm^2$ encouraged the release of bulk pieces of the substrate via corrosion along grain boundaries. The pulses had a defined pulse length of uniform or non-uniform duty cycle and a DC offset indicated by the dashed line. Once the surface was roughened during Period A, the DC offset was transitioned to more a reducing potential over Period B, so the ratio of reducing to oxidizing current slowly increased. During Period C, the pulses were entirely neutral or reducing. The final magnitude of the reducing pulse equaled that at which deposition current was maintained thereafter.

The duration of Period C may be prolonged if significant roughening occurred during Period A. The frequency of pulses was usually between about 1 Hz and about 1 kHz (and lower for surfaces with significant polarization resistance). Faster frequencies become ineffective due to comparatively slow mass transport rates. DC current may instead be used for Periods A and C, only. Examples of systems suitable for DC current included the most non-reactive metals in aqueous solutions, or reactive metals in ionic liquids, in which the most highly oxidized metal species remains reducible to a metallic state.

Period B was effective at reducing thick passivation layers on the first electrode. Conventional pulse deposition or reverse-pulse deposition methods are not sufficient to remove the passivation layers on more reaction metals like Fe, Al and Ti. For example, on a passivated nickel surface, the passivation layer comprised a mixture of nickel oxide and nickel hydroxide atop the outer metallic boundary. Charges must transverse this layer through each oxidation state before reducing completely. In contrast, deposition onto non-passivating surfaces such as Au went by comparatively simple adsorption and charge transfer steps.

Example 2— Surface Repair

This example demonstrates the effectiveness of the second current in rejoining the surface of a first electrode. FIGS. 17A-L shows a progression of surface smoothing on a copper electrode 1700 of 1 $cm^2$. FIG. 17A is the first image in the series, which was cut down the middle 1710 with shears before the rejoining process began. Several horizontal imprints 1720 are labeled in FIG. 17A (the same imprints are also evident in the other views through FIG. 17J) are apparent from pliers used to straighten the workpiece after shearing The first electrode, in this case the sheared copper sample, is viewed from the perspective of the source for a countercharge through the electrolyte (one-half saturation $CuSO_4$(aq) at ambient temperature).

At the start of the process, the Cu surface received no chemical pre-treatment (FIG. 17A). To roughen the surface for demonstration of crack filling, the copper workpiece (first electrode) was exposed to a 100 mA first current for several minutes (FIG. 17B). At this high current density, the metal from the first electrode primarily corroded in small chunks, starting at the outer edges of the first electrode. After several minutes, the surface of the first electrode was substantially rough (FIG. 17C). This roughening was much more than needed to remove surface oxides and promote adhesion of deposited metal, but the extreme roughness provided a useful visual of the effects of the second current.

The first current was applied at 15 mA (−0.5 V) from the source of a countercharge through the electrolyte, while two second currents were applied across the copper workpiece (second electrode) (FIG. 17D). The first transverse current ($TC_1$) was sinusoidal at 1 MHz 3 Vpp (50 ohm) between leads positioned on the workpiece equidistant from the shear. The second transverse current ($TC_2$) had the same attributes as the first but phase offset by 90°. Two-dimensional growth dominated despite a perpendicular positioning of the source of a countercharge to the surface of the workpiece as shown in the sequence of images from FIG. 17D to 17I. Normal charge density at edges of roughness was avoided. Instead, the horizontal imprints 1520 were filled in, which is also shown in the sequence until they disappear after having been filled as shown in FIGS. 17K and 17L. As processing progressed, the original smooth surface was restored resulting a relatively smooth workpiece with the shear filled as well as the imprints (FIGS. 17J-17 L). As most of the surface of the first electrode 1700 was restored, remaining valleys had a planar bottom and growth proceeded vertically until the valley was filled in with new metal-metal bonds formed between metal from the electrolyte and the metal of the walls of the valleys.

An appropriate waveform and parameters should be selected to induce the filling effect. This example was performed with simple sinusoidal waves at a fixed voltage, frequency, and phase offset. Had parameter settings been dynamic and able to adapt to the changing surface over time, as with sensory feedback, the surface features of the first electrode may be filled and smoothened simultaneously. Other factors that may effect the deposition and bonding are the position of the leads inducing the current across the workpiece, as well as the position of the source of countercharge relative to the workpiece, among other factors.

With no second current, the sample would have only demonstrated the outcome of conventional electrodeposition. For example, from FIG. 17C onward, deposition would have propagated roughness instead of smoothing and filling.

Example 3—Second Current Controlled Adhesion

Figure 18A:
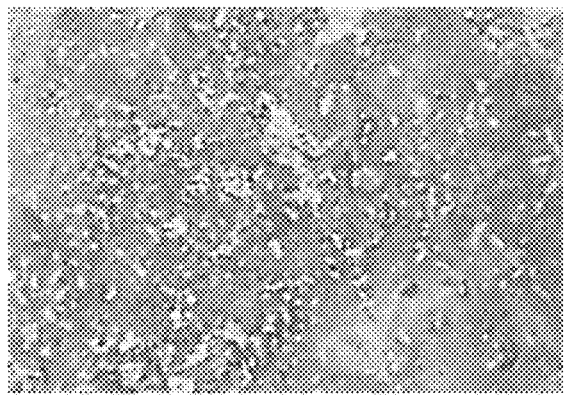
FIGS. 18A and 18B depict surface roughening of an originally smooth Cu/FR1 surface in 1.25 M $CuSO_4$(aq) at 25° C. using second current at 7 kV/30 mA (max limited) at 34 kHz (no counter electrode).
Figure 18B:
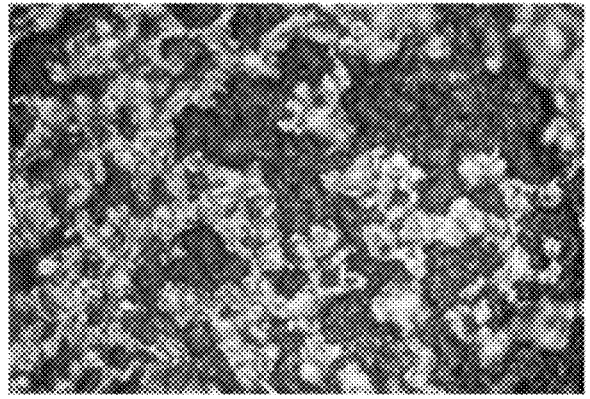

This example illustrates that the second (transvers) current can be used alone without absent deposition or corrosion under the first current. The second current alone was used at high potentials and modest frequencies to effect a high enough slew rate. FIGS. 18A and 18B are electron micrographs of a workpiece showing corrosion-based surface roughening caused by the transverse current. In particular, a relatively high voltage of 7 kV at 34 kHz, limited to 30 mA, induced significant surface roughening in less than 5 seconds. The surface had the passivation layer removed along with some metal from the workpiece. The process may be influenced toward finer removal of material, or the process may increase corrosion using a first current between the workpiece and a source for a countercharge, or by modulating the second current to higher frequencies or higher powers. Conventional surface pretreatments were unnecessary when applying the second current, particularly when the most highly oxidized metal species remained reducible in the electrolyte.

The transverse current reduced the level of porosity that would otherwise appear during electrodeposition. This effect also made new material adhere better by improving the deposit quality at the substrate interface. Epitaxial growth caused the new layer of deposited metal to adopt the crystal orientation of the workpiece. Controlling this mechanism promoted good adhesion, and was useful when the layer and substrate were the same material, or were two materials with similar lattice spacing. With two crystallographically dissimilar materials, forced epitaxial growth can cause significant strain stored at the interface that will be prone to cracking. Here, the transverse current was modulated to roughen the surface or reduce porosity while allowing the relief of strain during deposition.

Example 4— Pressed Powder Corroding Electrode

Figure 19A:
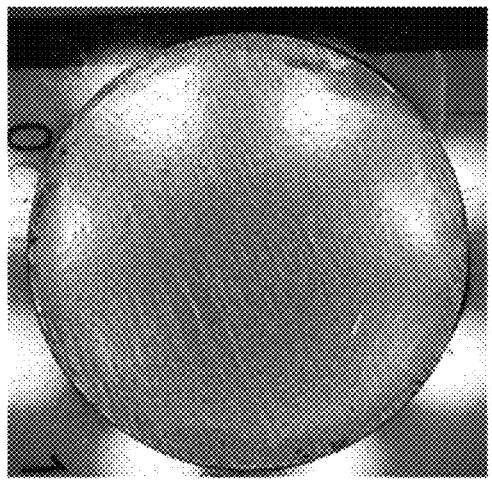
FIG. 19A depicts a corroding electrode formed from a pressed pellet containing Cu powder (about 10 μm average diameter) with 0.5% $CuSO_4$.
Figure 19B:
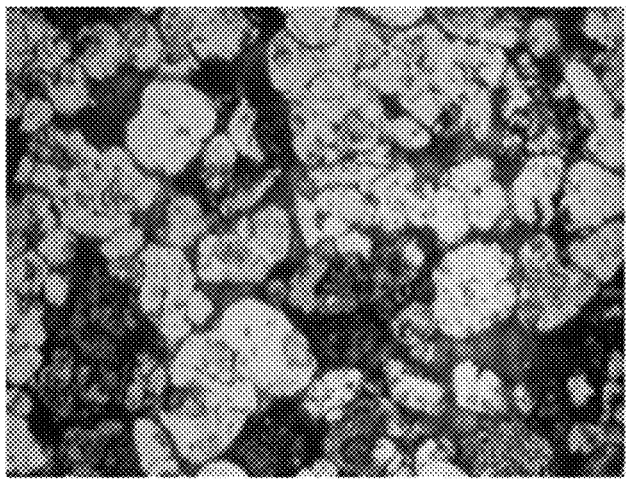
FIG. 19B presents the full view of the pellet.

Pressed power corroding electrodes were also investigated. FIG. 19A is photograph of a corroding electrode formed from pressed powder. The corroding electrode may be a source of countercharge, comprising mixed particles of various size, geometry, composition, and conductive or dielectric. The corroding electrodes included $CuSO_4$ with the metal particles, which were pressed together to replenishing the electrolyte as the electrode dissolved during operation. FIG. 19B is an electron micrograph of a deposit made using the corroding electrode of FIG. 19A.

Example 5—Bonding Using Computerized System

Figure 20:
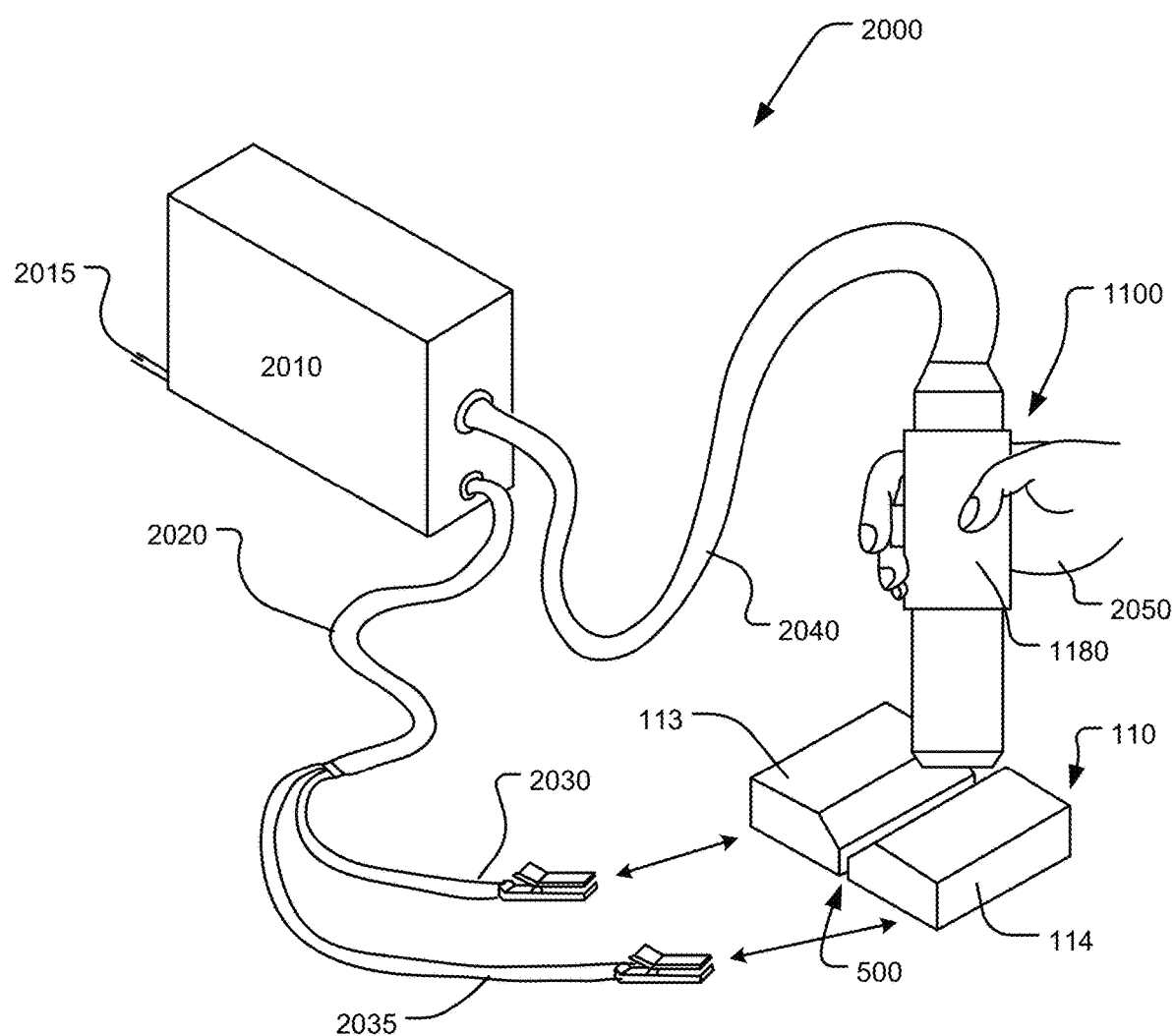
FIG. 20 summarizes unit 2000 in action as welding device with wand type applicator 1100 and auxiliary leads 2030, 2035.

To illustrate bonding using a computerized system described herein, reference is made to the device 2000 at FIG. 20. The electrolyte containing $AlCl_3$-EMIC is loaded into a reservoir of the main control unit (MCU) 2010 or the applicator 1100. The MCU 2010 is programmed to apply first current and second current power schemes selected for the Al—Fe electrolyte/corroding electrode combination. The device 2000 is powered from an external source such as a wall plug 2015.

Still referring to FIG. 20, The operator may attach two leads 2030, 2035 of the current collector cable 2040 to both portions 113, 114 of the first electrode 110 to polarize the first electrode 110 for the first circuit, and also to apply second current between the two leads 2030, 2035 through a surface of the first electrode 110. The portions 113, 114 are positioned relative to one another or in direct contact with one another to ensure a more even charge distribution across the first electrode 110. The user 2050 may forgo the leads 2030, 2035 for the sources of a countercharge built into the tip 1170, 1175 of the applicator 1100, as shown in FIG. 11. Alternatively, the user 2050 may use both, with the leads 2030, 2035 proving broad second current while the counterelectrodes of the applicator 1100 localize the second current across the area of the tip.

The electrolyte comprises polydisperse Fe particles having an average diameter between about 0.5 μm and about 1 μm, covered in 2 or 3 atomic layers of aluminum. The electrolyte also contains dissolved $AlCl_3$ at a molar ratio of about 1:1 with EMIC. See Example 12 for more details on deposition chemistry.

Within the applicator is a corroding electrode as a source of a countercharge comprising the same Al/Fe particles pressed into a 1-cm wide, 1-cm high pellet. As this electrode corrodes, the Al/Fe particle concentration of the electrolyte is replenished. The Al coating around each particle allows them to dissolve with an electroactive, reducible surface otherwise impossible for Fe in EMIC.

The material dimensions and composition are stable at temperatures below 80° C. Therefore, the operator may set the interior temperature of the applicator to 60° C. to promote deposition. The MCU's 2010 software may account for temperature and may modulate the applied power automatically.

The operator 2050 may manipulate the applicator 1100 to directly contact the junction 500 of the portions 113, 114 of the first electrode 110 with electrolyte from the tip. By manipulating the applicator 1100, the operator 2050 may activate one or more controls 1180 on the applicator 1100. These controls may execute the power sequences specified in the software controlling the MCU 2010. The sequence may include current to positively polarize the first electrode, removing the passivation layer on the surface. This step may be followed by a negative DC polarization of the first electrode with square wave second current at 1 kHz and 10 dbm and DC offset of 5 V. This waveform for the transverse current to imparts smoothness during deposition of the dissolved Al and Al—Fe particles. The transverse current also activates the gap defined by the two portions 113, 114 of the first electrode 110 for deposition.

Capacitance- and impedance-based feedback measurements may inform the MCU of changes in the deposition environment. The feedback can detect solids suspended or dissolved in electric field between the workpiece and the source of a countercharge. The feedback can detect the decreasing surface area on the workpiece, which indicates that the surface has been smoothened. The feedback can also detect that a junction has been closed with newly deposited material. The feedback may allow the MCU to automatically modulate the applied potentials and current density.

Once the gap is filled, the DC offset is decreased to 0 V while the second current switched to 1 MHz and −60 dbm to continue imparting smoothness to later layers over the junction. The operator 2050 may start, stop or regulate the flow of electrolyte and power through all circuits in this way. The junction 500 is replaced by deposited material with chemical and physical properties similar to or the same as the two original portions 113,114 of the workpiece 110.

Example 6—Repairing Chemical Tank

Methods of the present disclosure may be used to repair a crack in the exterior of a tank storing several tons of chemicals. The disclosed method avoids the dangers of hot work (welding, brazing, cutting) normally used for these repairs, which could ignite or react the chemicals in the tank. Also, the tank need not be removed from service for repair, avoiding the loss of productive time and minimizing environmental exposure.

To perform the method, the surface of the crack is cleaned to remove paint, grease and dirt. With the surface clean, the worker applies an applicator patch over the crack. The patch contains a viscous Fe electrolyte containing Fe particles having a diameter between about 100 nm and about 300 nm, and a Fe corroding electrode as the source of a countercharge and additional Fe particles. Other metal species may be included in the electrolyte to match the alloy of the tank. Two contacts on the pad are oriented on either side of the crack so the second current propagates transverse to the crack's length. The patch, and several others like it, may cover other cracks on the tank. All patches are connected to a remotely controllable MCU.

The worker leaves the vicinity of the tank and safely controls the MCU remotely. The MCU is programmed to first apply a corrosion-roughening step through the electrochemical circuit. The roughened surface is primed for new metal deposition. Next, the MCU proceeds with slow deposition with second current of 10 dbm at 4 GHz and DC offset of 0.5 V. The second current frequency is chosen because it is sufficiently fast while not stimulating dangerous chemicals stored in the tank. Power is lost from dissipation across the crack. Power is set to 10 dbm compensate for this dissipation.

Moreover, Fe particles in the electrolyte are sufficiently small to fill the width of the crack. The Fe particles are directed by the transverse current, the potential that it induces, the electrophoretic force of the 0.5-V DC offset in the waveform. In some instances, particularly at high frequencies that exceed the mobility of the charged species such as 4 GHz, the Fe particle may be too large to oscillate much at the high frequency. However, the transverse current can still induce a neutralizing effect ($V_{AVE}$ ca. 0) at sharp edges of the particles as well as the substrate. As a result, charged species are directed to deposit more uniformly regardless of surface features.

The repair can be made with applying only the needed energy to the tank. When the repairs are complete, the worker removes the patches from the tank. Repairs can be made more frequently because the disclosed methods are ease and safe compared to conventional dangerous hot work. The worker or his peers can assess the quality of the repair and maintain standards and process control following data review. And the quality and properties of the deposited metal are much higher than conventional welds, are better matched to the tank base material by selection of the metal species for deposit, and are more uniform than would otherwise be possible with conventional hot work repairs.

Example 7— Anti-Corrosion Method

This example describes a corrosion suppression system (CSS), which greatly extends the life of heat exchangers. A 12" length of copper alloy tubing (½" outer diameter) transports effluent at 80° C. from a water purification system to a heat exchanger. The effluent is highly saline water (120 g/kg) with dissolved ammonia and metal ions from a potable water stream of a reverse osmosis system. The inner surface of the tubing is thinly lined with a self-healing polymer coating, which protects the copper alloy from corrosion. The lining minimally affects the heat transfer of the effluent to the copper alloy. Without the lining, salt and ammonia would oxidize and corrode the copper alloy. Once pitting occurs from corrosion, the tubing would be much more susceptible to failure.

As effluent flows through the tubing, the CSS monitors and passes transverse current along the length of the tubing. For this monitoring mode, the transverse current is applied as sinusoidal waveform at 0 dbm, 50 kHz, and pulsed for 100 periods each 5 min, followed by a resting phase. The self-healing polymer evenly distributes the transverse field strength across the tubing. An electric field results from the passage of transverse current. The conductivity of the effluent attenuates this electric field. The exterior of the tubing is open to air with a dielectric constant of 1, while the polymer exhibits a value of 2.2. These parameters define the baseline for the impedance measurement. Changes in integrity of the lining, the temperature, the fluid composition, and the flow rate of effluent are detected from deviations in the baseline impedance measured on the transverse current.

After several days of continuous operation near the temperature and pressure limitations of the self-healing polymer, a defect develops in the lining that allows the effluent to directly contact the copper alloy. Normally, the copper alloy underneath the polymer would corrode and pit at the defect, compromising the mechanical integrity of the system. The CSS, however, detects the defect from a change in the baseline impedance caused by a sudden increase in the impedance signal when the effluent directly contacts the copper alloy. In response, the CSS switches from the monitoring mode using the periodic transverse current to a repair mode using a continuous transverse current at 0.2 dbm and 30 MHz. The higher power of the repair mode compensates for the signal attenuation. The higher frequency of the continuous transverse current outpaces the rate of the corrosion reaction, so that the progression of corrosion is halted and the defect is repaired. The wavelength of the transverse current is selected to be less than the length of the tubing. The polar symmetry of the sinusoidal waveform disrupts the flow of electrons and ions near the defect, which would normally facilitate corrosion. A net change is not induced in transverse current, because the mean potential at the defect remains at zero.

With the corrosion stabilized, the surrounding polymer is not further compromised. The self-healing polymer at the defect can recover, for example via internal hydrogen bonding catalyzed by solutes in the effluent. Once recovered, the self-healing polymer again isolates the copper alloy from the effluent. The impedance signal returns to is baseline. The CSS switches from the repair mode back to the monitoring mode using a pulsed transverse current.

Example 8— Two-Dimensional Computer Simulation of the Bonding Method

A two-dimensional computer simulation explored the charge distribution induced by transverse currents no offset and at a 180° offset. The simulation revealed that transverse currents induced non-uniformities in the electric field, similar to roughness in the physical topography of a workpiece. These non-uniformities would be counterproductive to uniform deposition. Modulating the electrodeposition and the transverse currents together overcame this simulated effect without dramatically increasing the total electric field.

Figure 21:
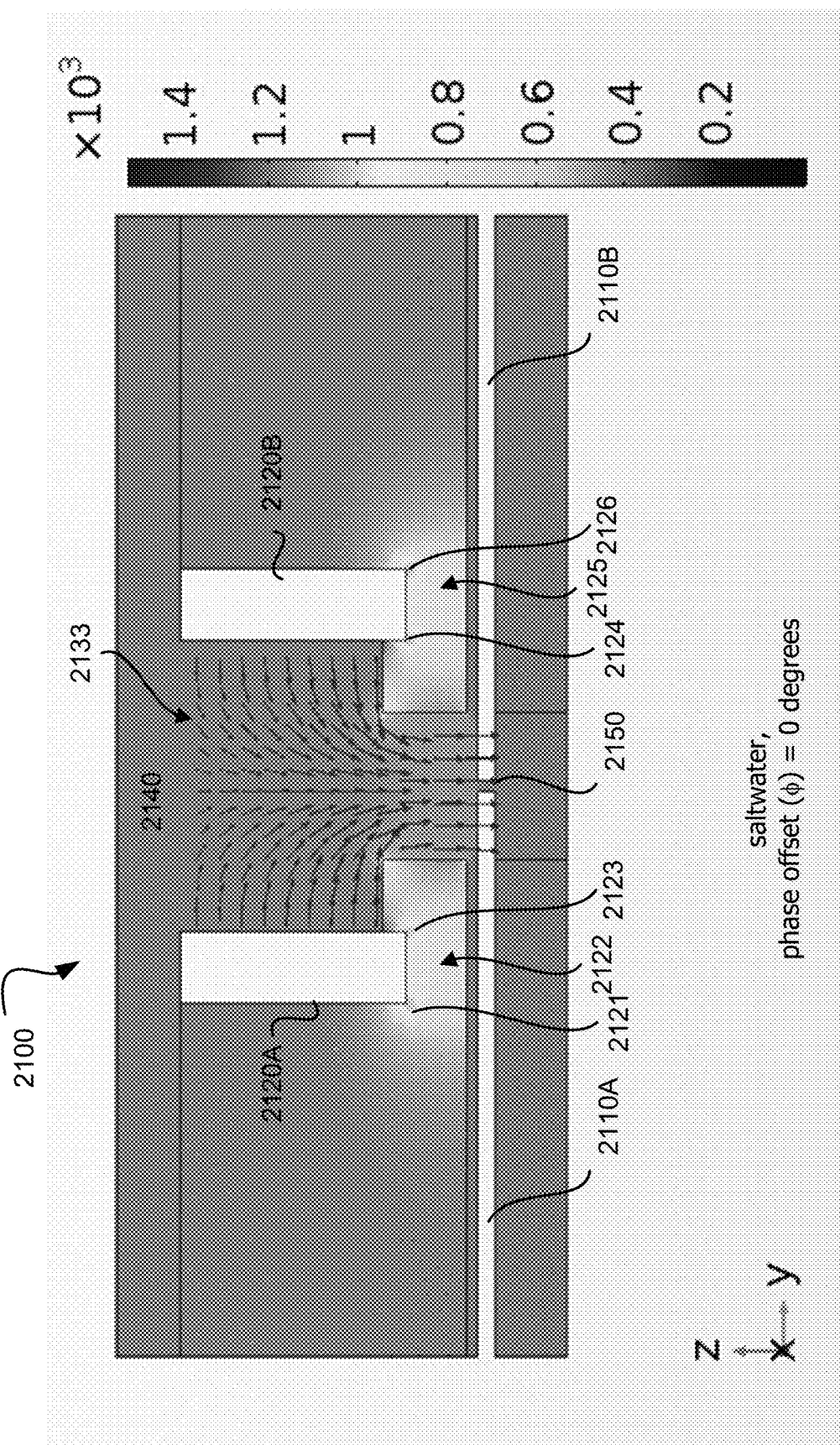
FIG. 21 shows the simulated electric field results for both electrodeposition and transverse currents in saltwater when the lower workpieces have a phase offset, phi of 0°.

Referring to FIG. 21, a simulated device 2100 comprised two anodes 2120A, 2120B and a cathodic workpiece in two segments (2110A, 2110B) having a gap 2150 between the segments 2110A, 2110B. The workpiece 2110A, 2110B was in electrical communication with the anodes 2110A, 2110B through an electrolyte 2140. In the simulation, the electrolyte 2140 was saltwater, the "conductivity(2)" parameter was 5, the time was 9.75 µs, the slice was the electric field norm (V/m), and the relative angle between the electrodeposition and transverse current (phi) was 0°. The arrows 2133 are the electric field lines.

This simulation of FIG. 21 resembles conventional pulse plating where both the left 2110A and right 2110B regions of the workpiece were pulsed evenly. Here, the transverse current pulsed the workpiece 2110A, 2110B without pulsing the anodes 2120A, 2120B. The magnitude of the electric field lines 2133 is illustrated by the length of the arrows. The electric field across the surface was uniform, particularly along the z-axis.

Figure 23:
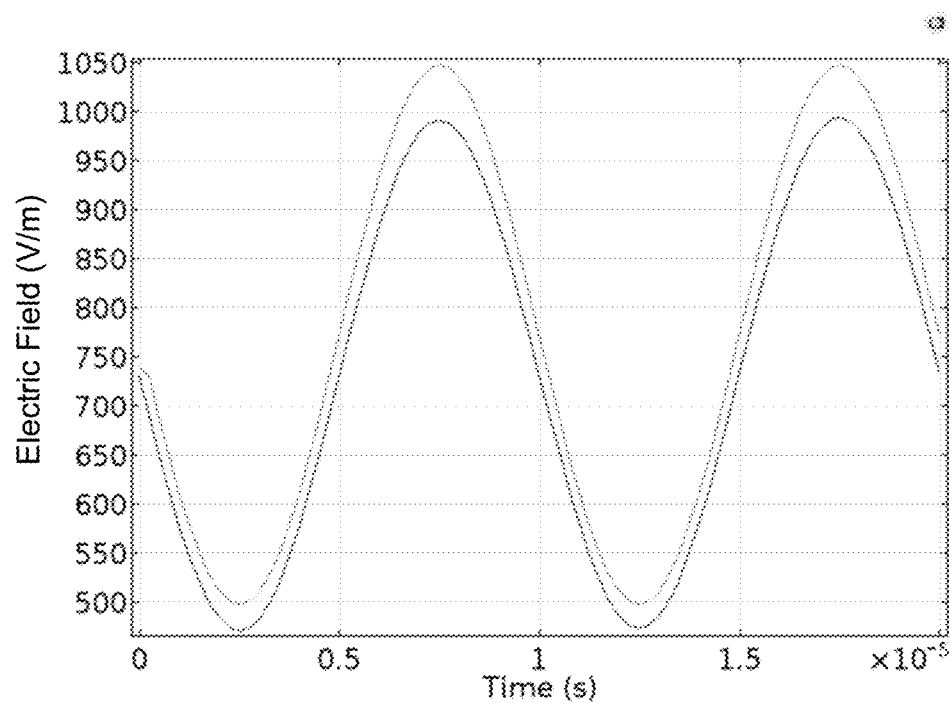
FIG. 23 shows the electric field oscillation minima and maxima during deposition at phi of 0°.

Low charge density is shown in blue and strong charge density showing in red. The charge density 2122, 2125 is greatest between the anodes 2120A, 2120B and the workpiece 2110A, 2110B, especially at the corners 2121, 2123 of anode 2120A and the corners 2124, 2126 of anode 2120B. Little charge density was seen in the gap 2150. The electric field lines 2133 were perpendicular to the workpiece 2110A, 2110B. Referring to FIG. 23, the oscillation minima and maxima were between about 450 V/m and about 1050 V/m.

Figure 22:
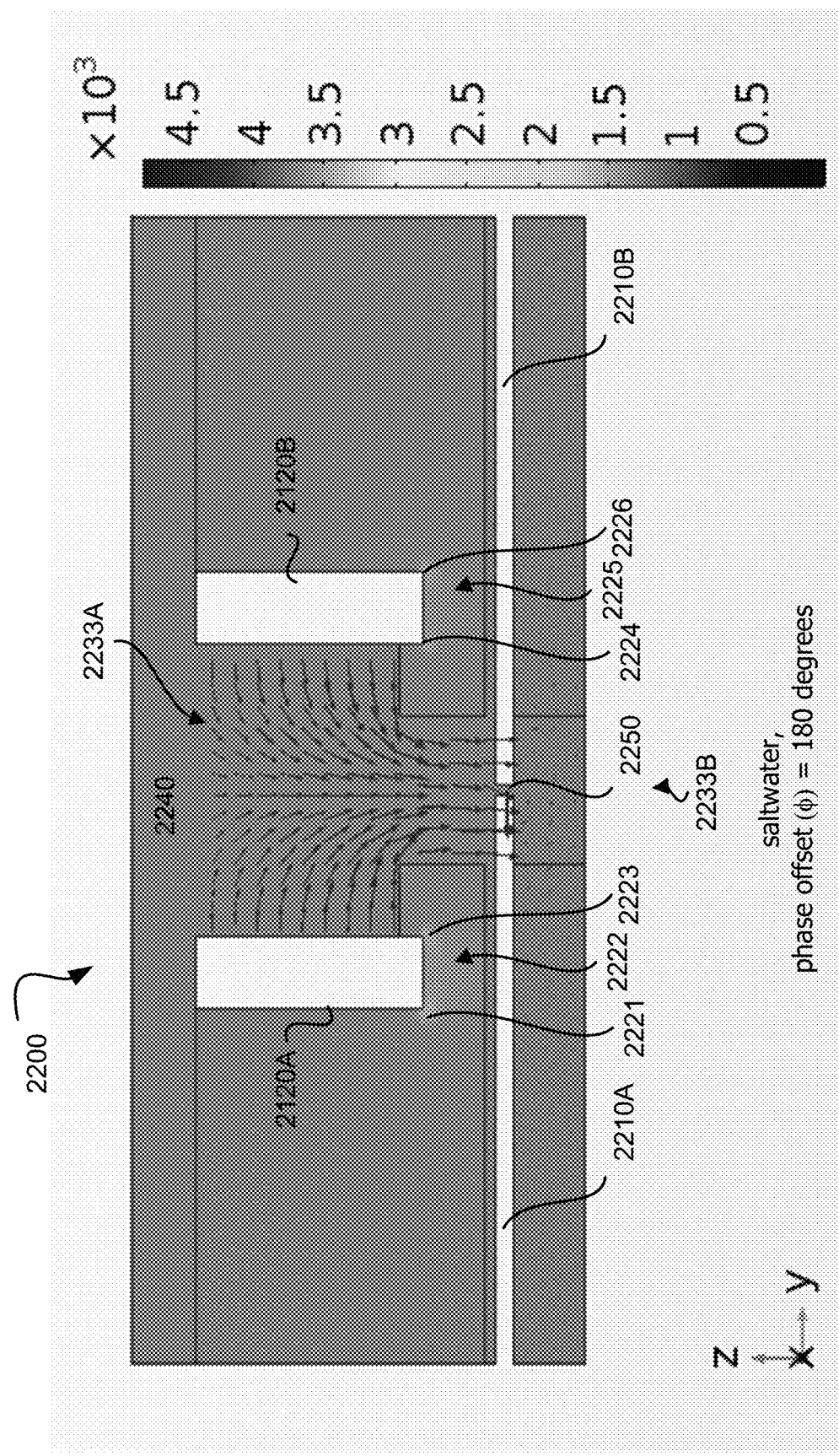
FIG. 22 shows the simulated electric field results for both electrodeposition and transverse currents in saltwater when the lower workpieces have a phase offset, phi of 180°.

Referring now to FIG. 22, a simulated device 2200 comprised two anodes 2220A, 2220B and a cathodic workpiece in two segments 2210A, 2210B having a gap 2250 between the segments 2210A, 2210B. The workpiece 2210A, 2210B was in electrical communication with the anodes 2210A, 2210B through an electrolyte 2240. As with the simulation from FIG. 21, the electrolyte 2240 was saltwater, the "conductivity(2)" parameter was 5, the time was 9.75 µs, and the slice was the electric field norm (V/m). In the simulation of FIG. 22 the relative angle between the electrodeposition and transverse current (phi) was 180°, where the left 2210A and right 2210B regions of the workpiece were pulsed so that the voltage on the left had the same magnitude but opposition polarity as the voltage on the right. The arrows are the electric field lines above 2233A the workpiece and on the backside of the workpiece 2233B.

The electric field 2233A was very strong along the y-axis. As the transverse current cycled through a full period, the magnitude of the electrodeposition field arrows 2233A above the workpiece 2210A, 2210B became uneven, particularly along the z-axis. This behavior worked against a uniform deposit, even as the field strength along the y-axis aided uniform deposition. An electric field 2233B was also induced on the backside of the workpiece 2210A, 2210B near the gap 2250. The charge density 2222, 2225 was greatest between the anodes 2220A, 2220B and the workpiece 2210A, 2210B, especially at the corners 2221, 2223 of anode 2220A and the corners 2224, 2226 of anode 2220B. Charge density was also seen in the gap 2250, where the electric field lines 2233A bent toward to the workpiece 2210A, 2210B near the gap 2250.

Figure 24:
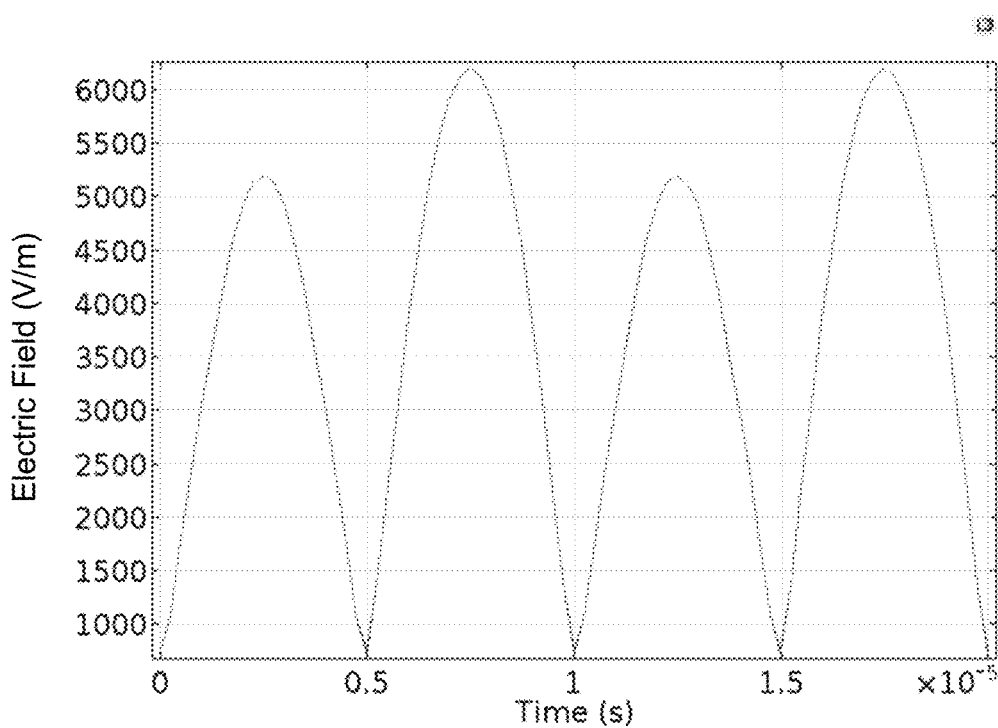
FIG. 24 shows the electric field oscillation minima and maxima during deposition at phi of 180°.

Referring to FIG. 24, the maxima increased to over 6000 V/m. Such high field strength along the z-axis may cause roughness on the workpiece and burnout via oxidation and oxygen adsorption. However, by inversely modulating the electrodeposition against the transverse current, the electric field strength perpendicular to the workpiece can be stabilized even when the transverse current increases. This modulation leads to smoother deposits without decreasing the average rate of deposition.

Example 9— Bonding Method Using Copper Metal Bonding Method

This example showed copper joining workpieces of copper and steel and analyzes how the electrodeposition and transverse currents combine in the signal generator. In one experiment, two 5"×1" pieces of 0.08" thick copper sheet were joined along their longest dimensions. In a related experiment, two pieces of steel were joined using an electrodeposition current of −300 mA. Samples prepared using conventional electrodeposition methods and the bonding method disclosed herein were compared to each other.

A high-density polyethylene (HDPE) applicator with a dielectric constant of about 2 was used. The electrolyte was aqueous saturated $CuSO_4$ with no additives. Two copper anodes (5"×0.54"×0.125") were used without isolating bags. Electrodeposition proceeded with and without AC waveform modulation of the electrodeposition current relative to the transverse current. When present, the transverse current was applied with a sinusoidal waveform having an amplitude of 120 mA to balance the electric field parallel to the surface. The equivalent impedance of the transverse current and electrodeposition at the cathodes was 2.4 ohm when combined.

Figure 25:
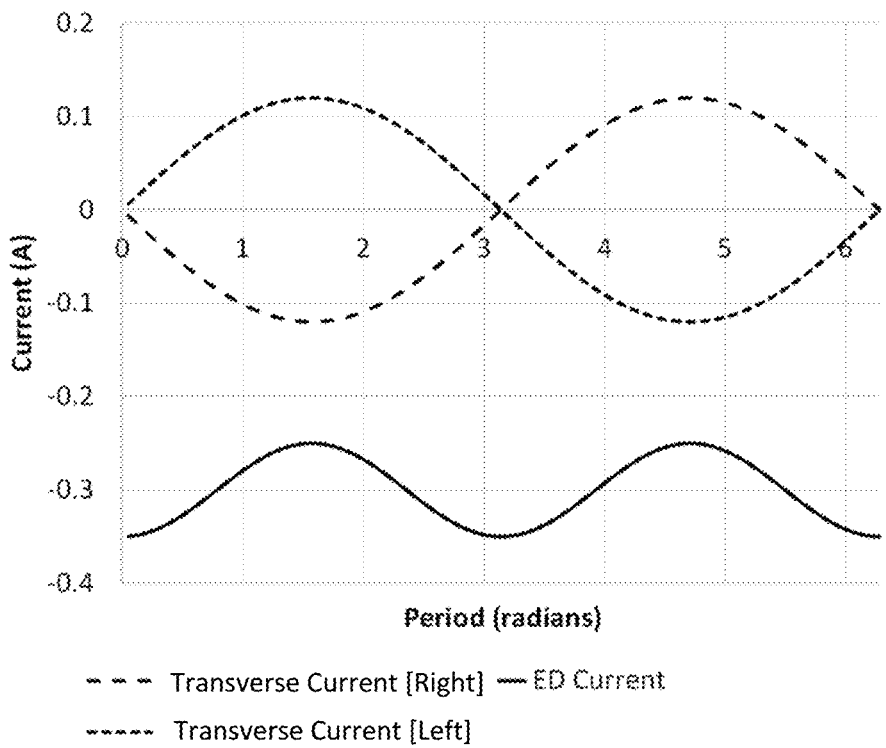
FIG. 25 shows the Transverse Current Right, Transverse Current Left, and the electrodeposition current sent on separate channels.

Referring to FIG. 25, the right transverse current was applied via an electrical contact, Channel A (ChA), to the right workpiece. The left transverse current was applied to the left workpiece via Channel B (ChB). ChA and ChB included two equal transverse currents at a 180° phase offset at 100 kHz. As the strength of the ChA-ChB signal increased, the electrodeposition current decreased, so that the total current perpendicular to the surface remained within acceptable tolerances and did produce rough deposits.

Figure 26:
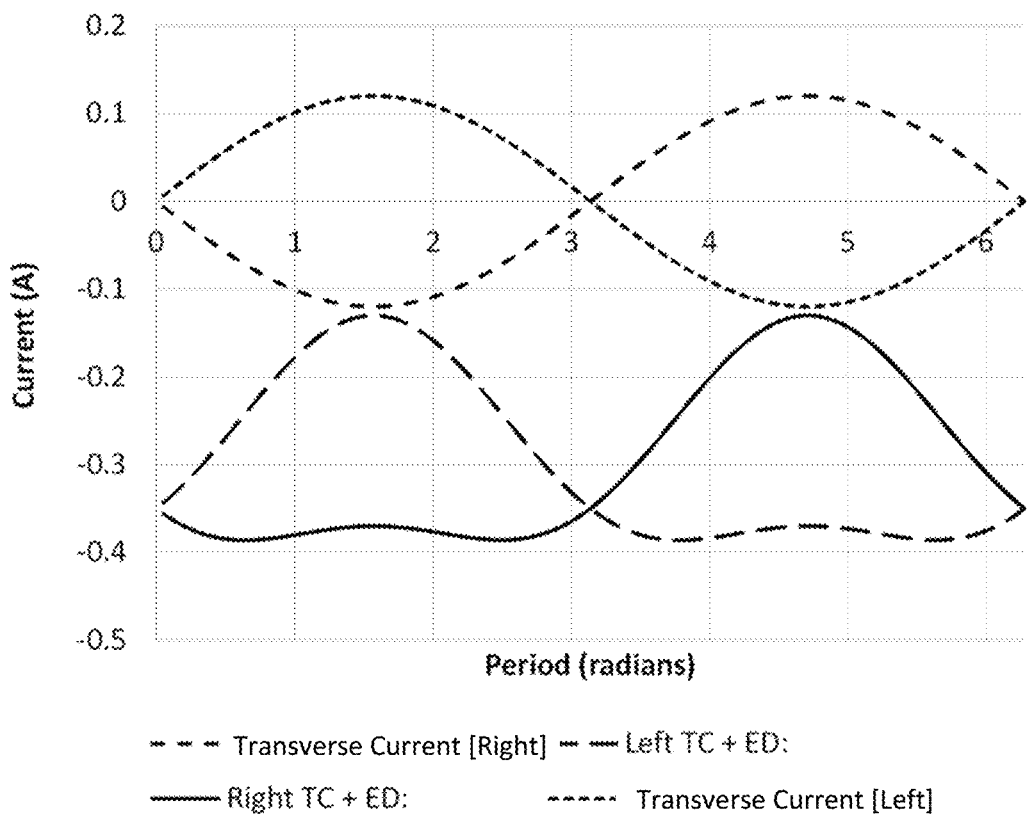
FIG. 26 compares the original transverse current signals to the new combined signal, where the Transverse Current Right, Transverse Current Left, and the electrodeposition have been combined.

A composite waveform resulted when the electrodeposition current was combined with the transverse current in the left and right channels. FIG. 26 compared the original transverse current to the new composite waveform. The difference between ChA and ChB were the same between both waveforms. The vector of the field changed at 0-π compared to π-2π. This change distinguished the signals of the disclosed methods from those used in conventional pulse plating, which does not have the described field changes. Here, the net current remained negative, facilitating continuous electrodeposition.

Figure 27:
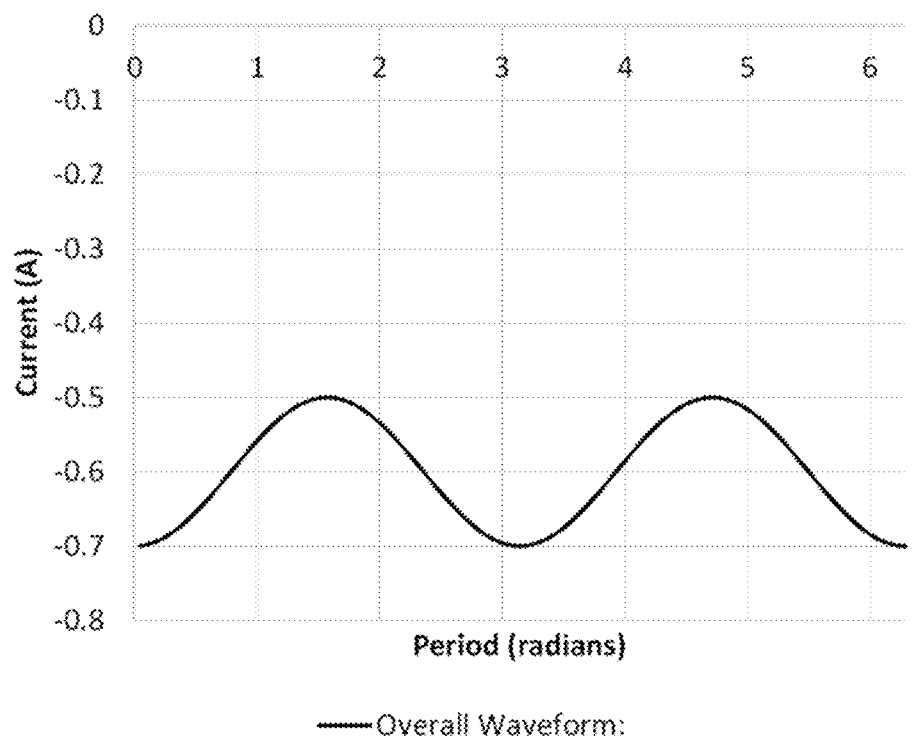
FIG. 27 shows combined left and right signals for the transverse current.

Referring to FIG. 27, the signal could be mistaken for conventional pulse plating in a scalar interpretation. However, this interpretation does not consider the vector of the signals constituents resulting from the electrodeposition and transverse currents. In conventional pulse plating, the anode experiences the same but opposite polarity pulsing as the cathode. In contrast, in the disclosed bonding method the anode experienced only some pulsing in FIG. 27. Specifically, the anode experienced only the pulsing of the uncombined electrodeposition current.

Figure 28:
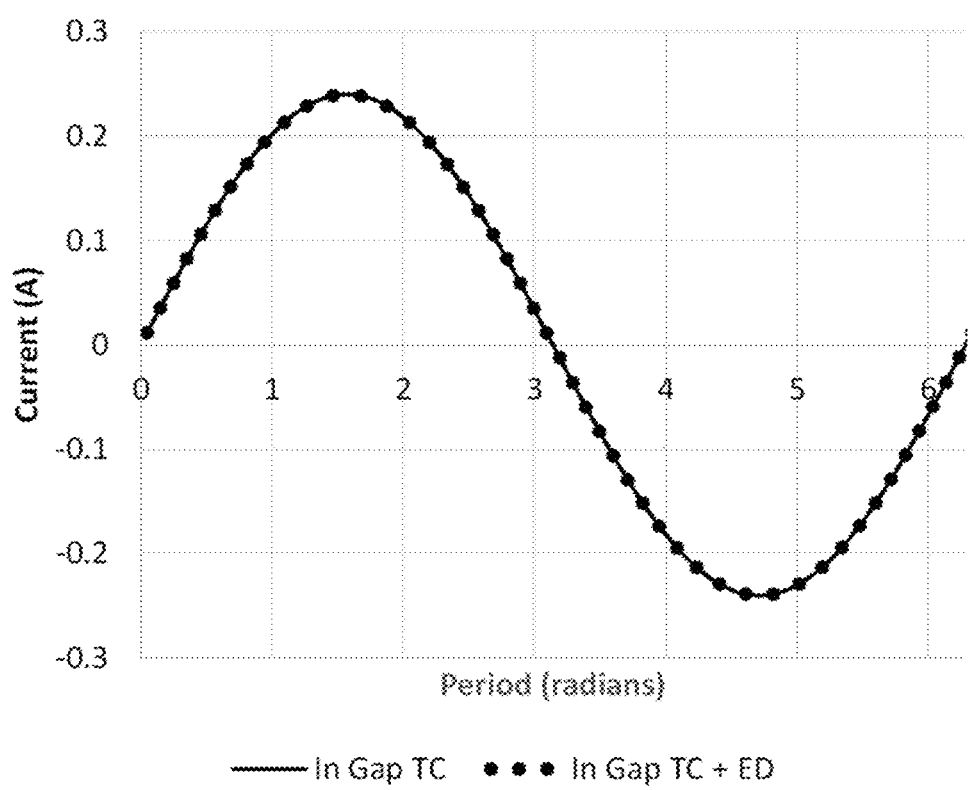
FIG. 28 shows that the parallel current imparted inside the junction between the two pieces being joined is the same when comparing the original transverse current signals to the combined transverse current electrodeposition signal.

Referring to FIG. 28, the parallel current imparted inside the junction between the two workpieces was the same compared to the original right and left transverse currents and to the combined transverse-electrodeposition signals. Modifying waveforms of the electrodeposition and the transverse currents may alter the duty cycle in the junction. For example, a duty cycle of 80% positive current and 20% negative current promotes the deposition of material inside the junction from one side of the junction to the other side of the junction. This duty cycle may be changed gradually during the process, so that the balance of positive and negative current promotes more growth from the other side of the junction.

Figure 29:
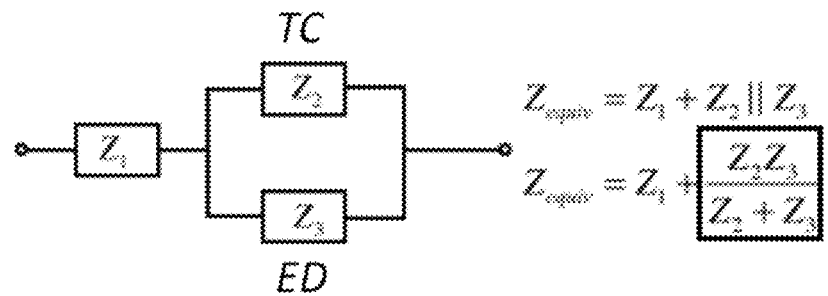
FIG. 29 is an equation showing that an equivalent impedance is assumed with transverse current and electrodeposition signals applied in parallel.
Figure 30:
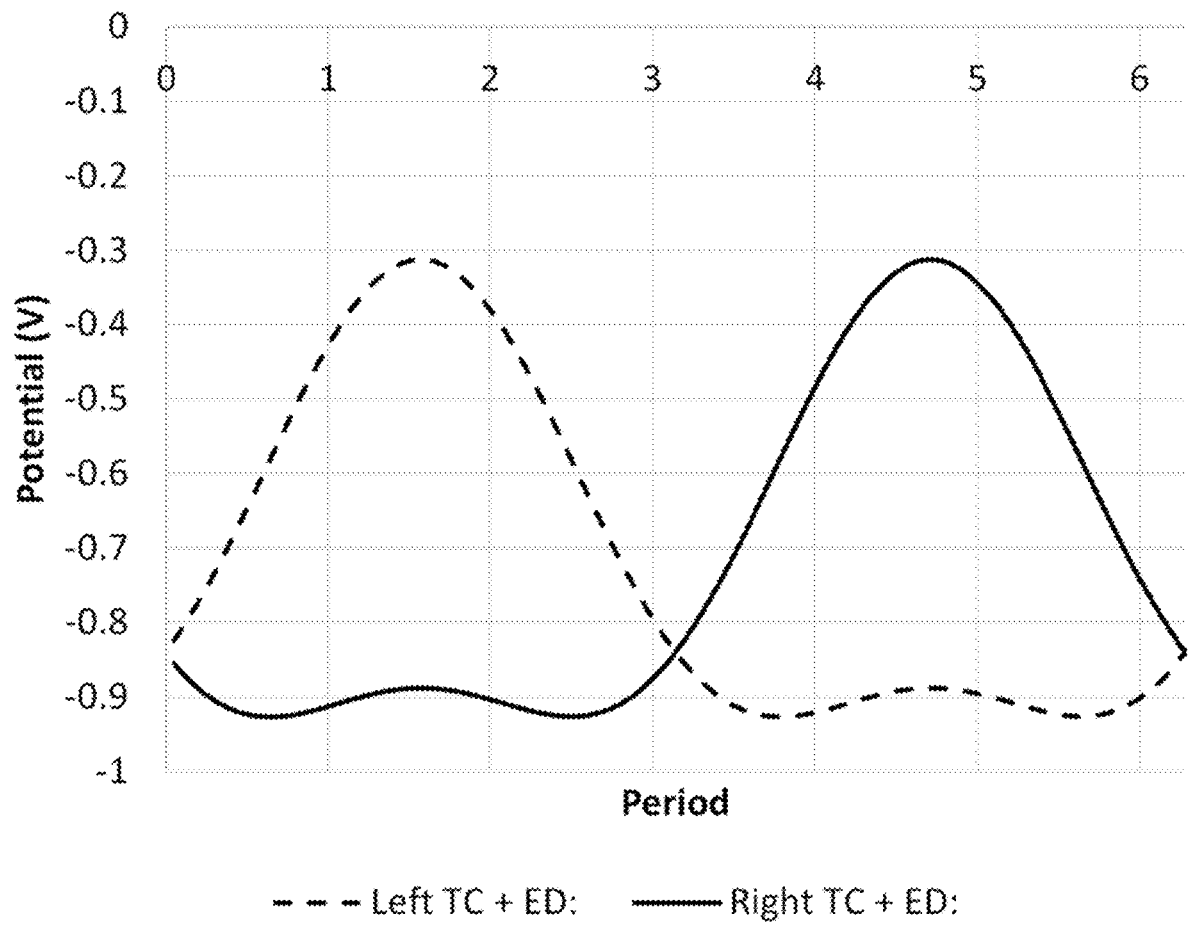
FIG. 30 shows the calculated potentials for ChA and ChB using the equivalent impedance.

Referring to FIG. 29, an equivalent impedance $Z_1$ was assumed for the transverse current $Z_2$ and the electrodeposition current $Z_3$ applied in parallel. The transverse current operated with an impedance of 6 ohms, due to the impedance of the AC signal generator, the cables, and mostly the low impedance of the electrodes. The electrodeposition current operated with an impedance of 4 ohms, due to the resistance of the electrolyte, the impedance of the bias-tee that combined the transverse current and the electrodeposition signals, and the polarization resistance at all electrodes. At FIG. 30, the calculated potentials for ChA and ChB used the equivalent impedance. The exact potential varied with hardware, temperature, concentration, and pH of the electrolyte.

Figure 31:
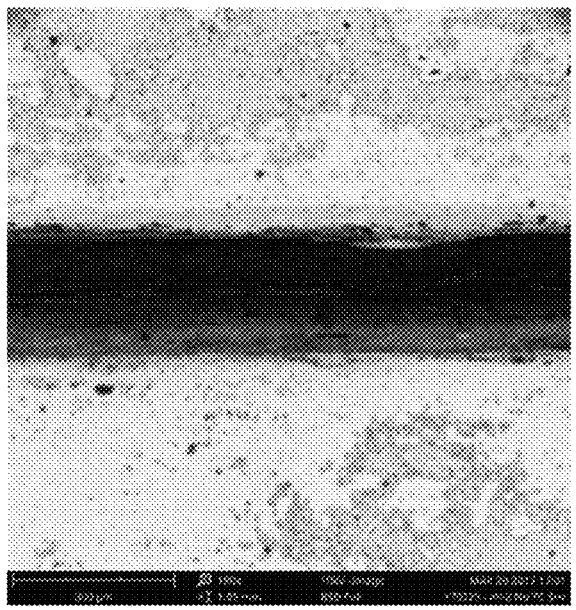
FIG. 31 is an electron micrograph depicting a gap in a workpiece where metal grows faster at the edges facing the inside of the gap than from the bottom of the gap. The result of this growth are weak joints and poor bonding.
Figure 32:
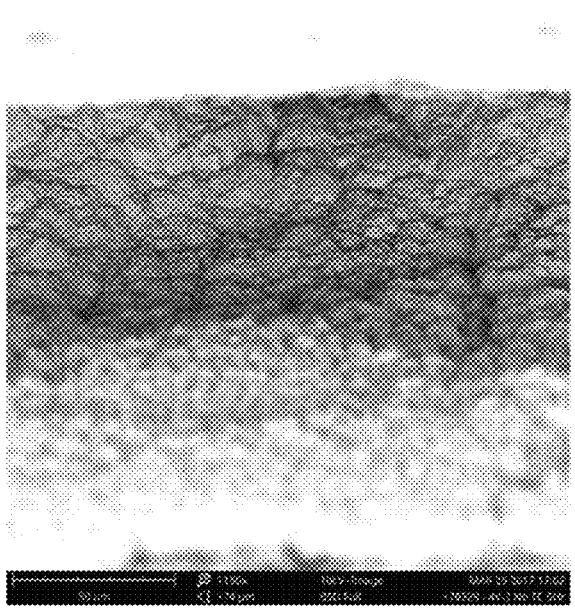
FIG. 32 is also an electron micrograph depicting the poor joining of the two sides of a gap in a workpiece.
Figure 33:
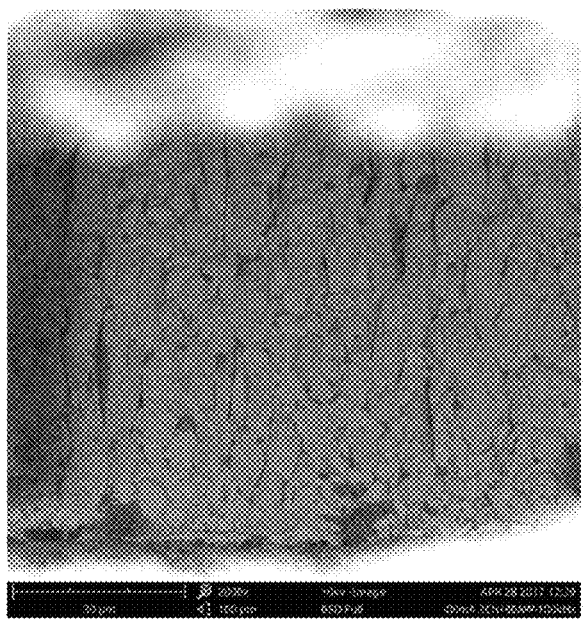
FIG. 33 is an SEM image of the bottom of a workpiece deposited with copper using transverse current, oriented to what was the gap between the joined pieces.
Figure 34:
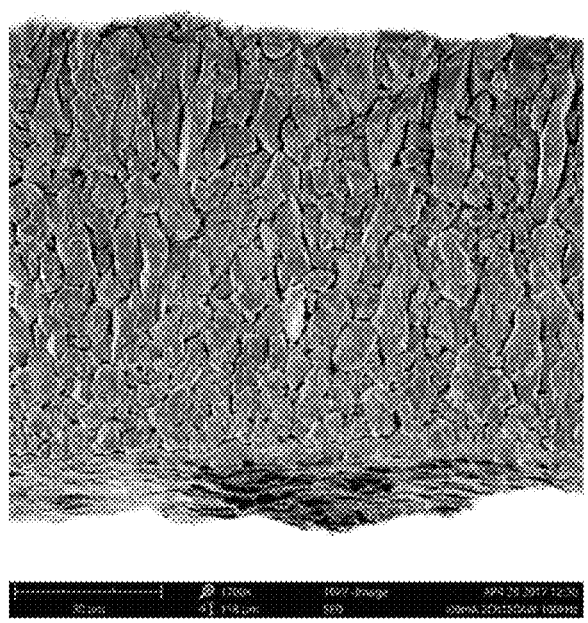
FIG. 34 is also an SEM image of the bottom a workpiece deposited with copper using transverse current, oriented to show that the gap has been filed.

The original 5" long sample of joined copper workpieces was cut in half to access adhesive strength of deposited metal. FIGS. 31 and 32 show SEM images of the bottom of a copper sample treated conventionally, which accelerated growth of metal at the edges facing the anode. The gap between the two workpieces filled poorly and the joint was weak. FIGS. 33 and 34 show SEM images of the bottom of a copper sample treated with the bonding method disclosed herein. The strong electric field within the gap caused metal fill the gap flat and uniform. This flat geometry was much stronger than the convex geometry conventionally achieved. Elongated metal grains in the deposited metal aligned with the electric field from the transverse current. Modulating the electrodeposition current relative to the transverse current controlled of the field strength perpendicular to the surface, while allowing the field strength parallel to the surface to fluctuate. Further, the transverse current suppressed the accelerated deposition of metal that would normally occur at the anode-facing edges of the workpiece. This suppression prevented the gap from being pinched shut at the top before filling with metal, resulting in joint strength far superior to conventional and previously known methods.

Example 10— Incident-Reflection Method

This example demonstrated reflection of an incident transverse current (iTC) on a surface of a workpiece to generate a reflected transverse current (rTC). The iTC and rTC signals interacted to affect the deposition using the disclosed bonding method.

A sample was prepared from a FR1 circuit board coated with copper foil on both sides. Electrodeposition occurred at −1 V, using two copper anodes on either side of the circuit board. The transverse current was applied through two channels via an electrical contact on each side of the circuit board. Both channels applied a transverse current at 100 kHz and 1.5 Vpp with a 180° phase offset. The two sides of the circuit board had no direct electrical contact.

The incident transverse current (iTC) originated from the left side of the circuit board. The iTC signal changed as it travelled across the surface of the circuit board, because the electrodeposition and the electrolyte absorbed energy from the iTC. The remaining, unabsorbed energy in the iTC continued to travel across the surface until it encountered the right side of the circuit board. The iTC reflected back, generating the reflected transverse current (rTC). When iTC encountered rTC, their energies superimposed, like ripples in a pond. When the superimposition provided more energy at a point, the electrodeposition increased at the point as a function of the rate of the electrochemical reaction. The frequency and power of the iTC could be swept nonlinearly to promote a uniform electric field across the surface of the workpiece. Alternatively, the frequency and power of the iTC can target particular features or topographies on the surface of the workpiece.

Figure 35:
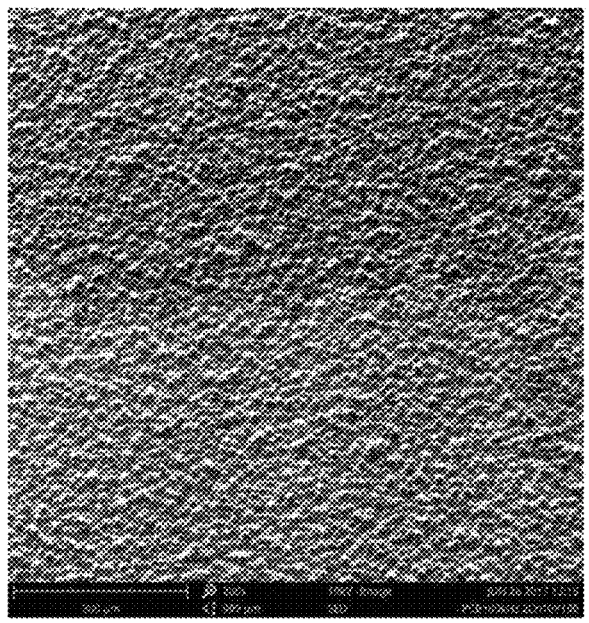
FIG. 35 was generated from a secondary electron detector, showing contrast between surface textures.
Figure 36:
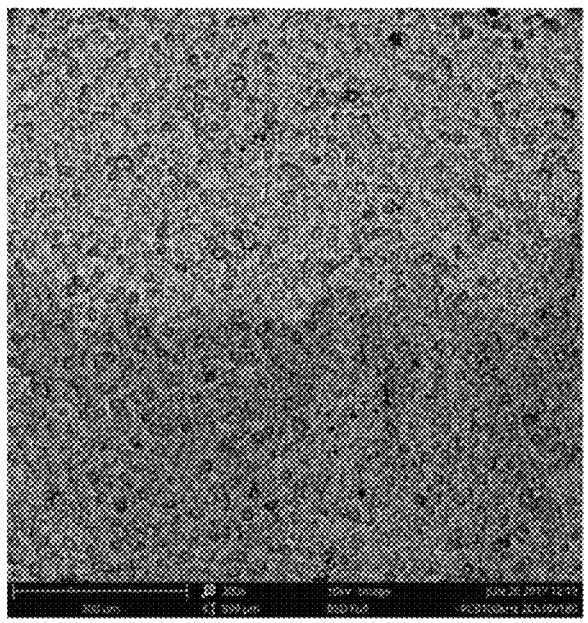
FIG. 36 was generated from a backscattered electron detector, showing contrast between the relative differences in atomic weight of different elements.

Referring to FIGS. 35 and 36, the deposited copper had a different finish, texture and morphology than the copper of the circuit board. FIG. 35 was generated from a secondary electron detector (SED), showing contrast between surface textures. FIG. 36 was generated from a backscattered electron detector (BSD), showing contrast between the relative differences in atomic weight of different elements. The SED showed the two regions differed in fine textures, though broader morphology was similar between regions. The BSD showed the regions differed in average elemental composition.

Figure 37A:
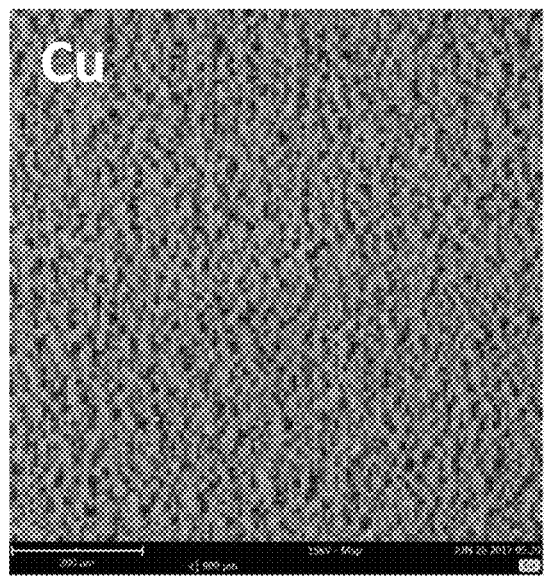
FIGS. 37A-D are the elemental analysis for the samples in FIGS. 35 and 36. Elemental mapping in FIG. 37A shows uniform copper distribution across the two regions. Overall, oxygen concentration was low (FIGS. 37C and D), but the oxygen levels were slightly greater on the bottom region (FIG. 37B).
Figure 37B:
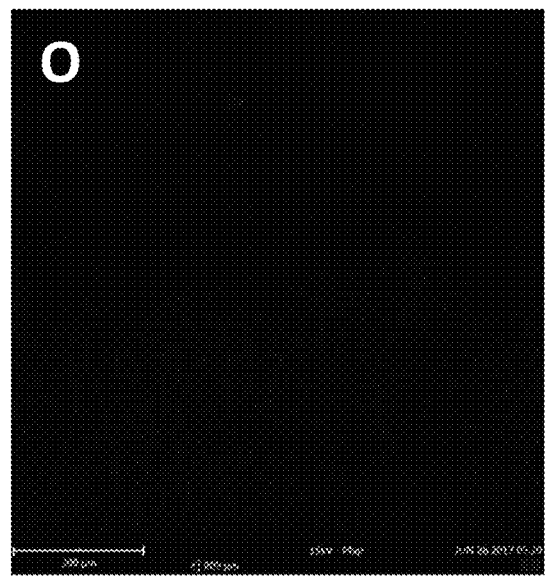
Figure 37C:
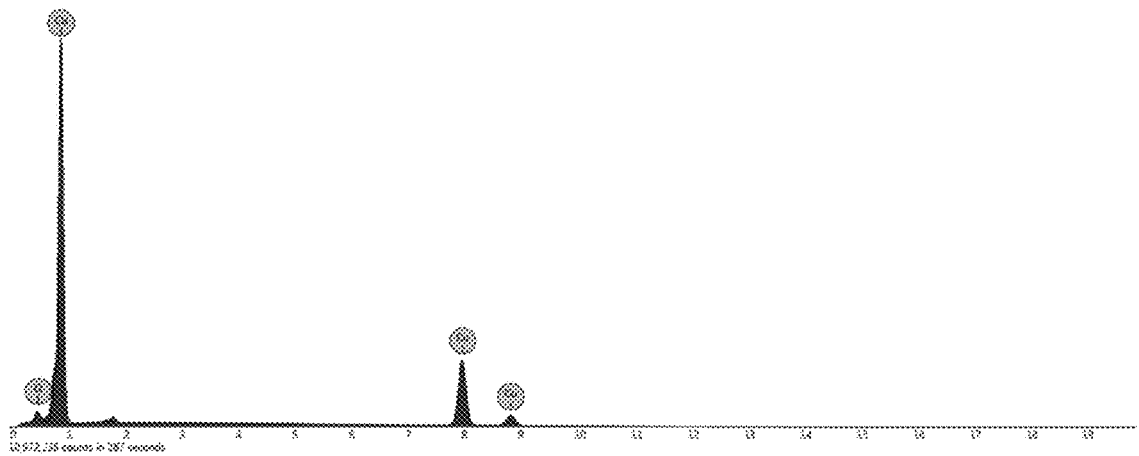
Figure 37D:
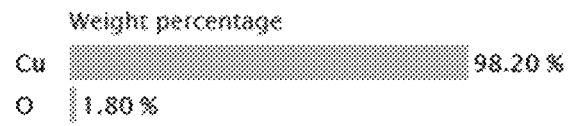

FIGS. 37A-C the purity of the copper was uniform, although morphology and nucleation differed between areas just a few microns apart. Elemental mapping in FIG. 37A showed uniform copper distribution across the two regions. Overall, oxygen concentration was low (FIGS. 37C and D), but the oxygen levels were slightly greater on the bottom region (FIG. 37B). This concentration difference is not because the lower area deposited more oxygen into the bulk, but instead because the surface area was greater due to

Example 11—Al—Fe Deposit

This example demonstrated successful deposition of a difficult alloy from an ionic liquid via co-deposition of particles. Particles originated from solution or from a corroding anode. The corroding anode was the preferred source because a greater number of particles were occluded during deposition.

The ionic liquid was a 1:20 molar ratio of trimethylamine hydrochloride (TMA-HCl) and urea. The anode was an Al—Fe composite having Al particles with an average diameter between about 0.5 µm and about 2 µm, and Fe particles with an average diameter between about 10 µm and about 1 mm. In some samples, an Fe sheet anode was also used with the Al particles mixed into the electrolyte. The cathode substrate was a steel coupon (¾"×¾"). The solution temperature was between about 100° C. and about 150° C. An electrodeposition current of −1.4 V was used.

Figure 38A:
FIGS. 38A-E shows aluminum particles embedded into an iron layer from ionic liquid. A vertical cross section of the sample was analyzed.
Figure 38B:
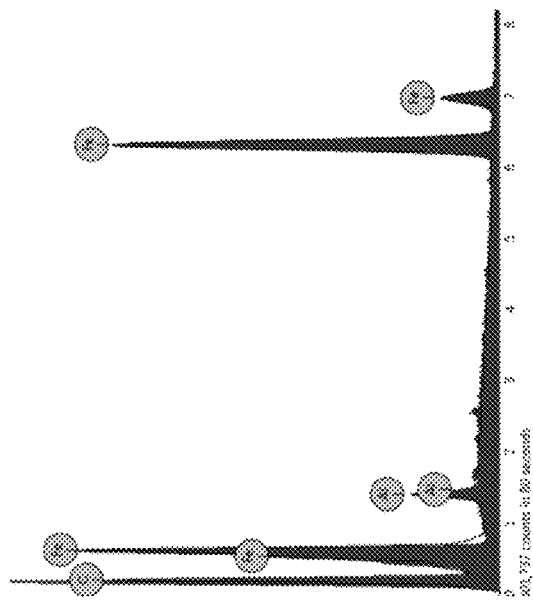
Figure 38E:
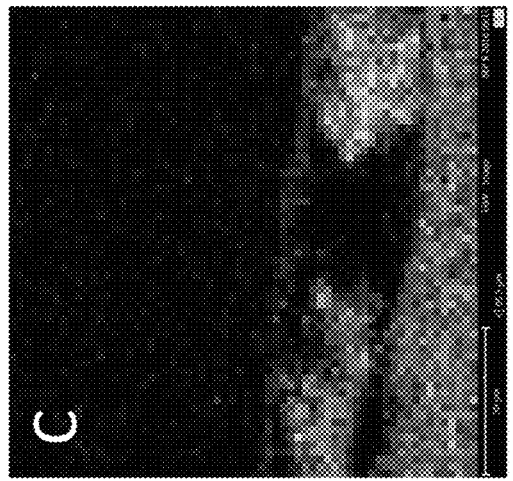
Figure 38D:
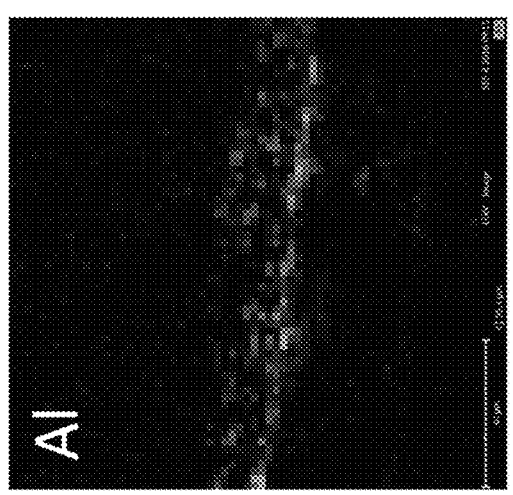
Figure 38C:
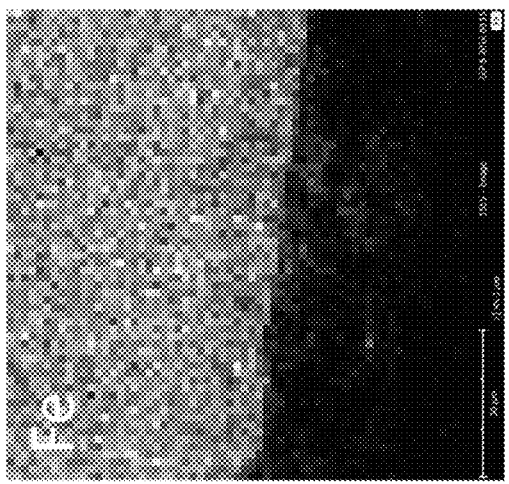

FIG. 38A is the elemental analysis of a vertical cross-section of the deposit showing iron, aluminum, and carbon. FIG. 38B was a scanning electron micrograph composite of the iron, aluminum, and carbon signals, showing the codeposition of aluminum (orange) and iron (yellow) at the surface of the steel substrate (yellow and blue). FIGS. 38C-E are the two-dimensional elemental maps for each iron (FIG. 38C), aluminum (FIG. 38D), and carbon (FIG. 38E).

Example 12— Deposition from an Aluminum Corroding Anode

This example demonstrated another deposition of the Fe—Al alloy, here using a corroding anode as the metal source. In this example, the electrolyte was an ionic liquid containing an about 1:1 molar ratio of ethylmethylimidazolium (EMIC) and $AlCl_3$. The active species in this electrolyte was $Al_2Cl_7$. The Al was dissolved in solution, and the iron originated from a corroding particle anode or a plate anode (See Example 11 above). The workpiece was copper (½"×¾"). The solution temperature was 30° C. The electrodeposition current was −1.6 V±0.2 V.

Figure 39C:
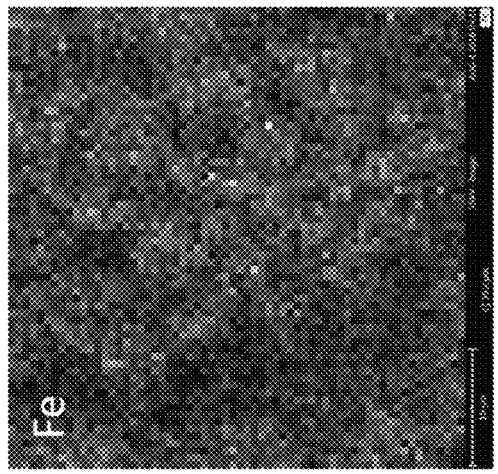
FIGS. 39A-D shows the approximately 1:1 aluminum-iron alloy deposited from the ionic liquid onto copper.
Figure 39B:
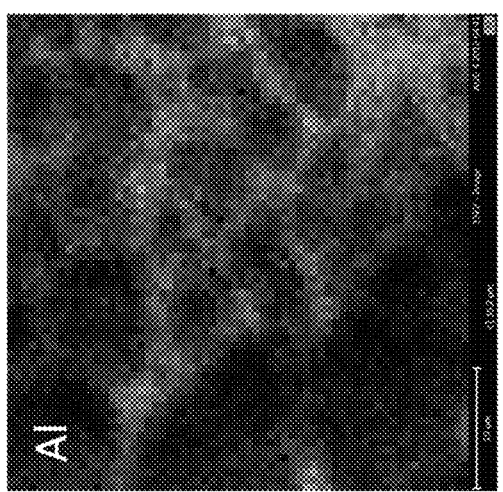
Figure 39A:
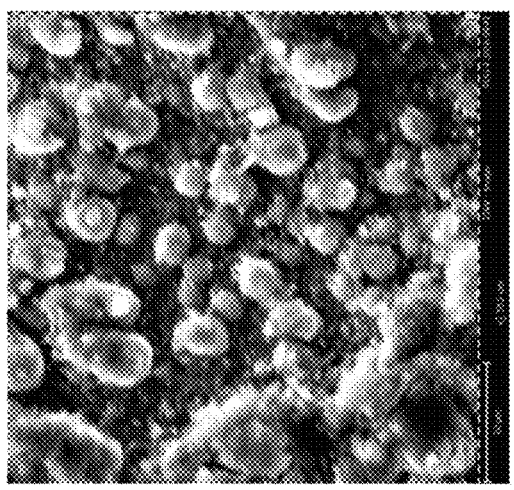
Figure 39D:
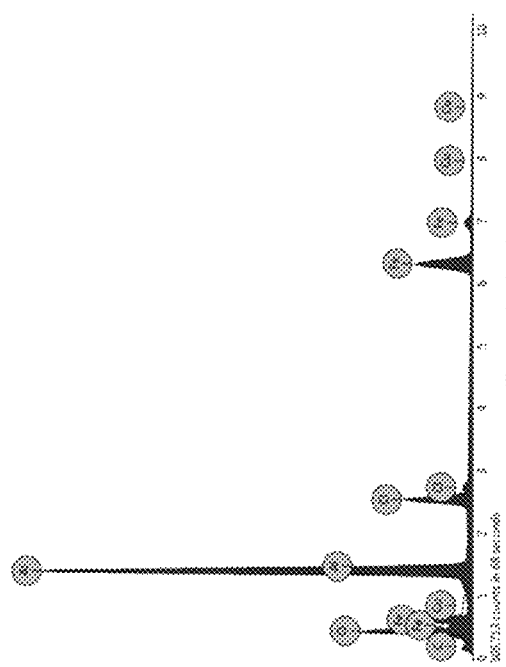

FIG. 39A is a scanning electron micrograph of the deposition. FIGS. 39B and 39C are the two-dimensional elemental maps for aluminum and iron in the sample, respectively, showing an approximately 1:1 aluminum-iron alloy deposited from the ionic liquid onto the copper workpiece. FIG. 39D is an elemental analysis confirming that the sample contained iron, aluminum, copper, carbon, oxygen, and chlorine.

Example 13— Fe—Zn Alloy Deposit

This example demonstrated Zn—Fe alloy deposition from an ionic liquid using a pressed powder electrode. An ionic liquid was prepared from a 1:2 molar ratio of choline chloride and urea. The zinc and iron sources for the deposit came from the anode and dissolved salts. The anodes tested were an iron anode, a zinc anode, or a Zn—Fe anode made of pressed powder or other preparation. A solution of 0.2 M $ZnCl_2$ prepared in the ionic liquid. Up to 0.3 M $FeCl_3$ was also added to the solution. The workpiece was mild steel (¾"×¾"). The solution temperature was 85° C. The electrodeposition current was −1.8 V.

Figure 40A:
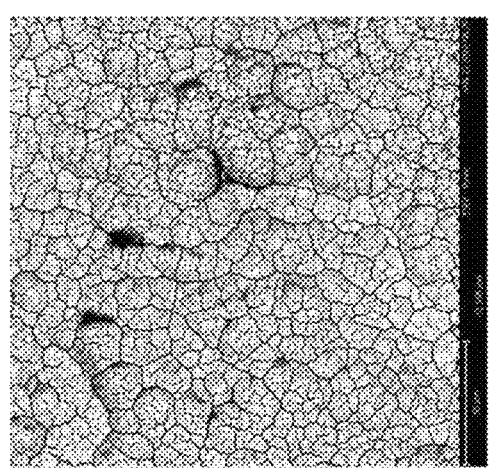
FIGS. 40A-H show a 5:4 (mol/mol) iron-zinc alloy was deposited from ionic liquid.
Figure 40B:
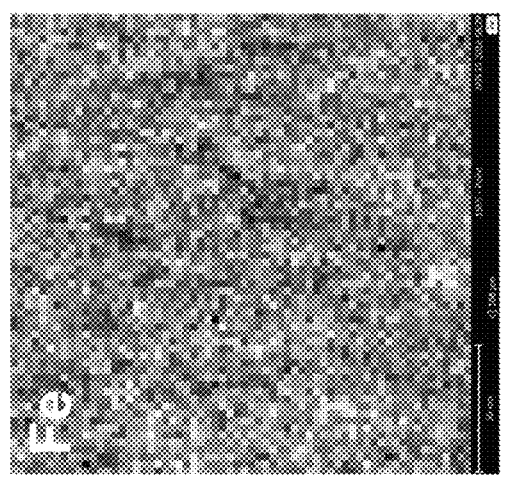
Figure 40C:
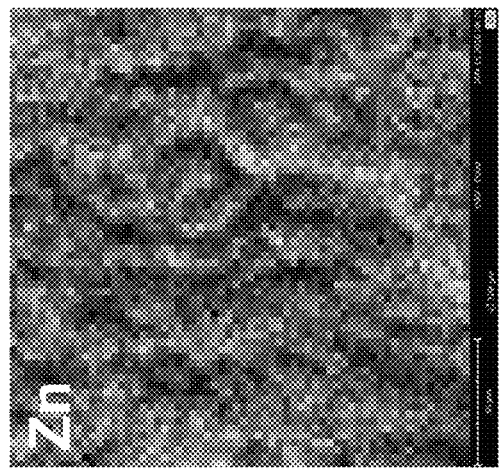
Figure 40D:
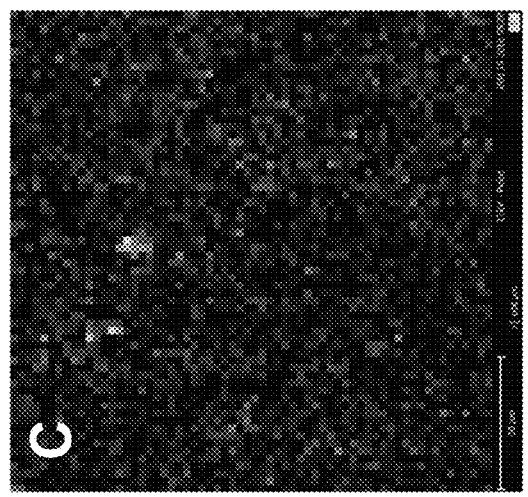
Figure 40E:
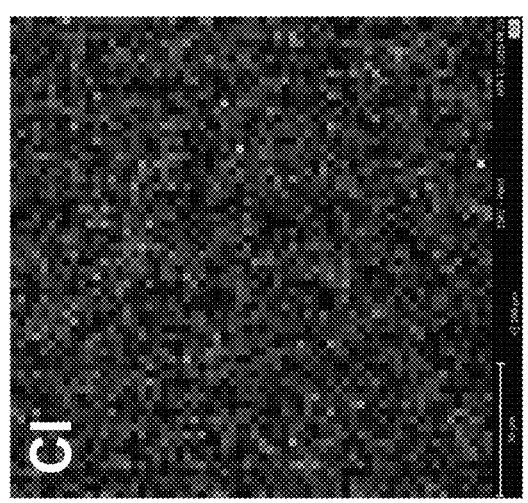
Figure 40F:
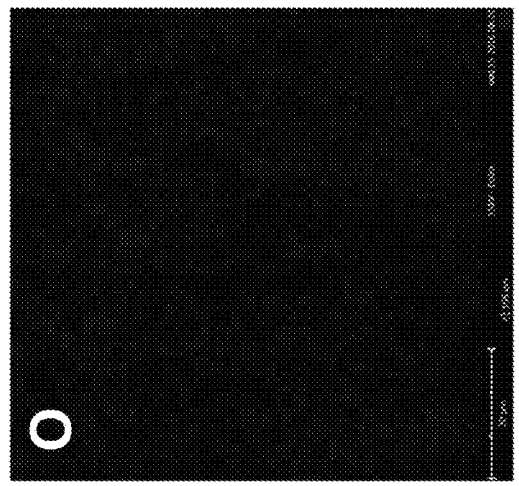
Figure 40H:
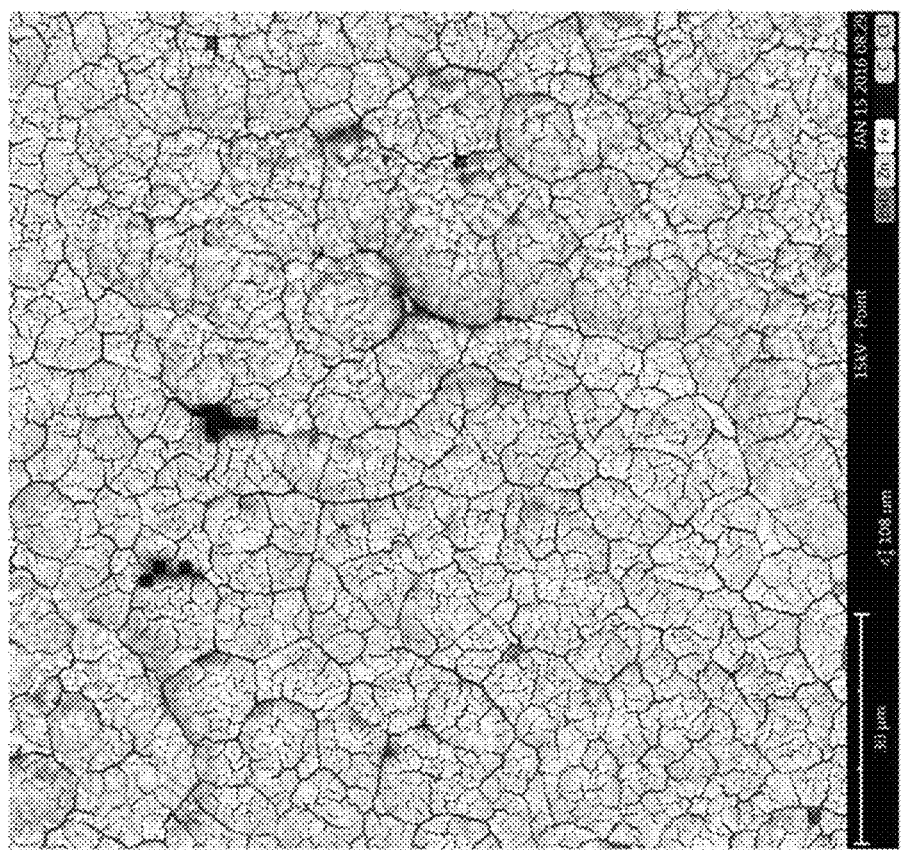
Figure 40G:
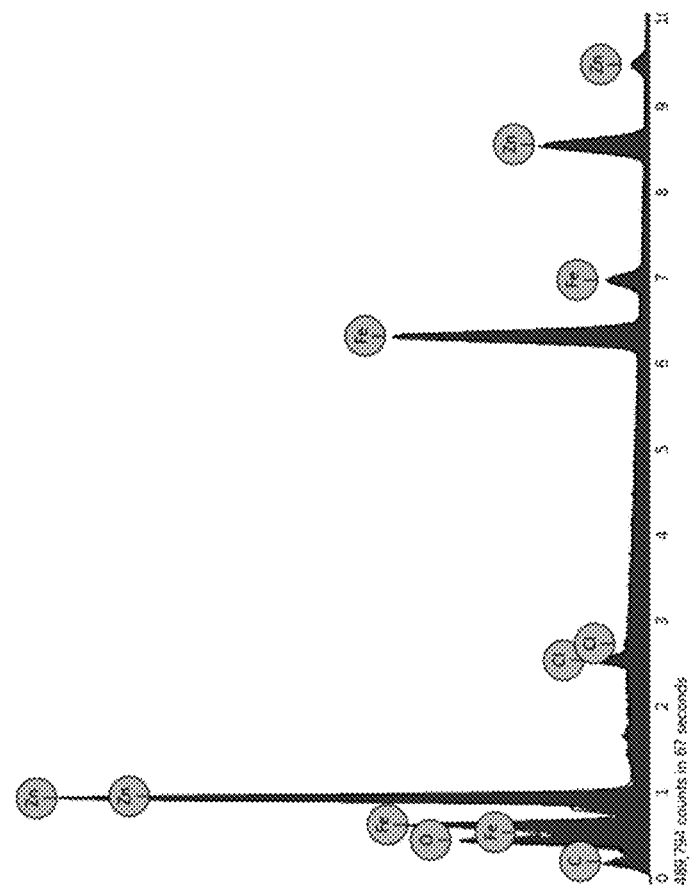

FIGS. 40A-H show a 5:4 (mol/mol) iron-zinc alloy was deposited from ionic liquid. FIG. 40H shows an electron micrograph composite of the electron micrograph (FIG. 40A), and the two-dimensional elemental contents for iron (FIG. 40B, yellow), zinc (FIG. 40C, light blue), carbon (FIG. 40D, cyan), chlorine (FIG. 40E, green), and oxygen (FIG. 40F, dark blue), showing the codeposition of zinc and iron to form the alloy. FIG. 40G shows the elemental distribution in the sample, showing that the sample contained iron, zinc, carbon, oxygen, and chlorine

Example 14— Plating Copper onto a Woven Workpiece

Figure 41B:
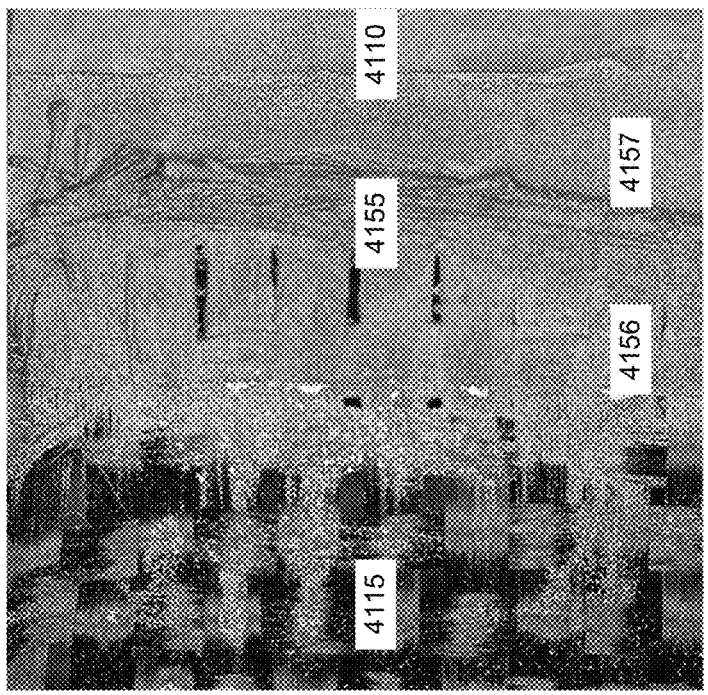
FIGS. 41A & B are photographs of copper bonded to carbon cloth from conventional electrodeposition (FIG. 41A) and from the disclosed methods using a transverse current (FIG. 41B).

This example compared copper bonding to carbon cloth via conventional electrodeposition at (FIG. 41A) and the disclosed bonding methods using transverse current (FIG. 41B). For each sample, copper (3"×1"×0.032") with a <110> crystal face was joined to 3 k woven carbon fiber cloth (3"×1"). The electrolyte was saturated $CuSO_4$(aq). The anodes were also Cu <110>. The bonding current density was 0.6+/−0.02 $mA/mm^2$. When present, the transverse current was applied through two channels, using a 180° phase offset, 5 Vpp, 100 kHz with a saw waveform. One channel was configured for the copper workpiece and the one channel was configured for the carbon cloth.

Figure 41A:
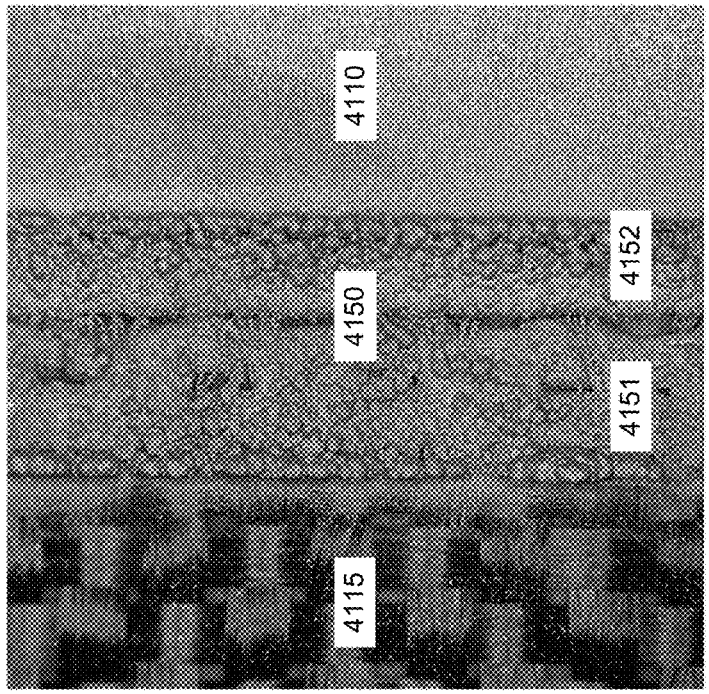

Referring to FIG. 41A, the junction 4150 between the carbon cloth 4115 and the copper workpiece 4110 did not receive as much new copper as the areas 4151, 4152 farther away. The junction 4150 had gaps where the weave of the underlying carbon cloth 4115 is still visible. As such, the joint between the two workpieces 4110, 4115 was very weak. Deposition near the junction 4151, 4152 was rough. Deposition on the copper workpiece 4110 was smoother and more nearly matched the <110> crystal phase of the copper workpiece 4110.

Referring to FIG. 41B for which a transverse current was applied during bonding, the junction 4155 between the carbon cloth 4115 and the copper workpiece 4110 received ample new copper. The junction 4155 had no gaps. The weave of the underlying carbon cloth 4155 was not visible. As such, the joint between the two workpieces 4110, 4115 had a strength similar to that of the original copper workpiece 4110. Moreover, the areas 4156 and 4157 adjacent to the junction 4155 also had thick deposits of new copper. The deposition across both the workpieces 4110, 4115 was smooth and nearly matched the <110> crystal phase of the copper workpiece 4110.

The bonding method of this example can also be applied to a non-conductive woven workpiece, such as a woven para-aramid synthetic fiber (Dupont™ Kevlar®). Because Kevlar® is not conductive like copper or semi-conductive like carbon, the woven workpiece is first impregnated with a metal salt, such as $NiCl_2$(aq), before further processing. Any non-conductive woven workpiece, such as cotton cloth or polyester cloth, may be pretreated in this way. The treated woven workpiece is processed using a method described to deposit aluminum, titanium, or another metal or alloy. Kevlar® or other non-conductive workpiece may be shaped into panels or shaped to a mold before deposition, so that the metallization locks the fabric into place.

Example 15— Further Examples of Joining Separate Workpieces

A. Joining Copper to Nickel

A copper <110> workpiece (3"×1"×0.032") was joined to nickel <200> (about 2.5"×1"×0.062") using copper. The electrolyte was saturated $CuSO_4$(aq). The anodes were also Cu <110>. The electrodeposition current density was 0.6 mA/mm$^2$. The transverse current was applied through two channels, with one channel configured to the copper workpiece and the other channel configured to the nickel workpiece. The transverse current was applied with a 180° phase offset at 5 Vpp and 100 kHz in saw tooth waveform. These were the same parameters for the transverse current conditions as the copper-carbon cloth at Example 14.

Figure 42:
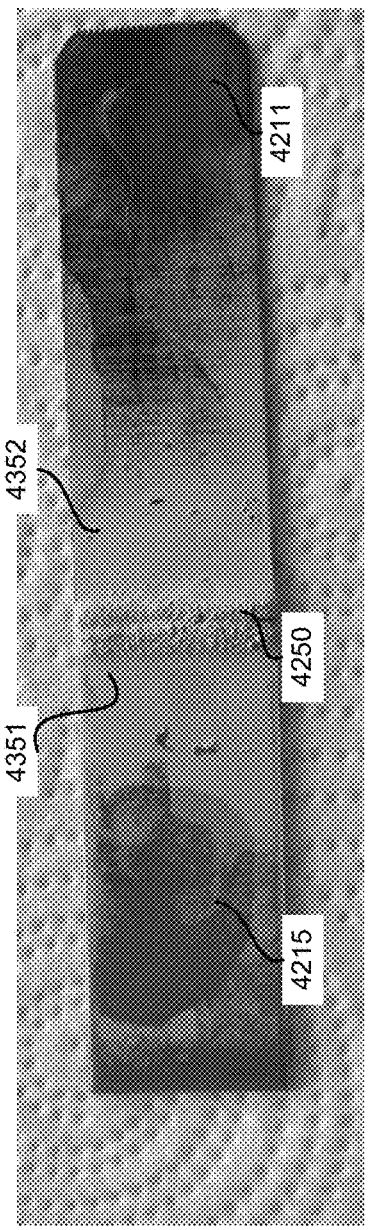
FIG. 42 is a photograph showing copper <110> joined to nickel <200> with copper following the disclosed method.

Referring to FIG. 42, the junction 4250 between the nickel 4215 and the copper workpiece 4210 received ample new copper. The junction 4250 had no gaps. As such, the joint between the two workpieces 4210, 4215 was mechanically strong. Moreover, the areas 4251 and 4252 adjacent to the junction 4250 also had thick deposits of new copper. The deposition across both the workpieces 4210, 4215 was smooth, although the junction 4250 received the most new material.

The differences in thickness and the similarity in conductivity between the nickel 4215 and the copper 4211 workpieces probably contributed to the junction 4250 not being as strong as the junction 4155 between copper 4110 and carbon cloth 4115 (FIG. 41B, Example 14). The thickness of the nickel workpiece 4215 was twice that of the copper workpiece 4211, while the conductivity between copper 4211 and nickel 4215 was closer than the conductivity of copper to carbon fiber. The Vpp could be decreased to lessen spikes in the electrodeposition field perpendicular to the surface, while maintaining a large potential difference in the junction. The phase offset of the transverse current to the electrodeposition current could be reduced to 90°. This reduction would also lessen the size of spikes in current density at the edge of the nickel workpiece. The frequency could be increased into the MHz region to suppress faster growth at edges, especially at the nickel edge which is already thicker.

B. Joining Brass to Aluminum

In another experiment, brass (3"×1"×0.032") was joined with copper to aluminum alloy 7075 T6 (about 2.5"×1"×0.032"). The electrolyte was saturated CuSO$_4$ (aq). Because an aqueous electrolyte was used, the aluminum was coated in zinc before the bonding. The anodes were Cu <110>. Electrodes has a 1-mm spacing. The electrodeposition current density was 0.36+/−0.02 mA/mm$^2$ for one hour. The transverse current was applied via a single channel at 10 Vpp/1 App and 100 Hz.

Figure 43A:
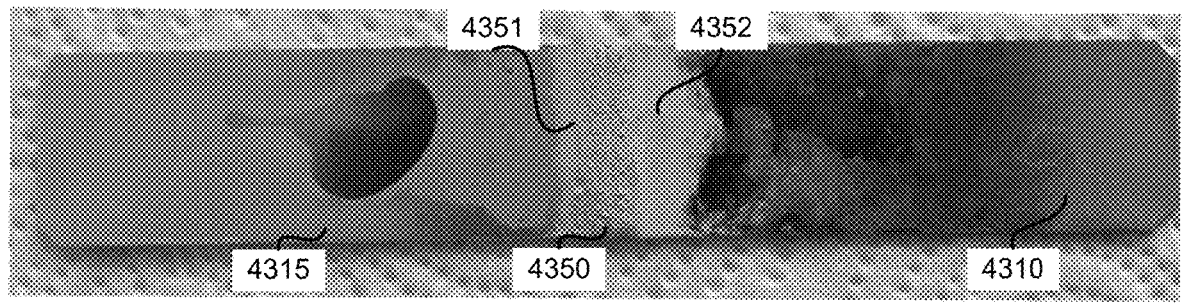
FIG. 43A is a photograph showing brass joined with Al 7075 T6 with copper following the disclosed method.
Figure 43B:
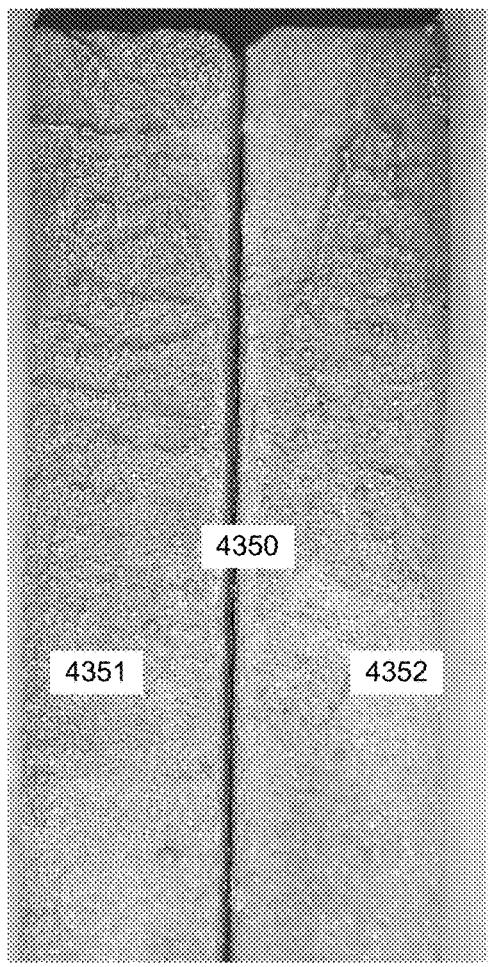
FIG. 43B is a magnification of the joint between the brass and aluminum sections.

Referring to the photograph at FIG. 43A, the junction 4350 between the aluminum 4215 and the brass workpiece 4310 received ample new copper. The junction 4350 had no gaps. As such, the joint between the two workpieces 4310, 4315 was mechanically strong. Moreover, the areas 4351 and 4352 adjacent to the junction 4350 also had thick deposits of new copper. The deposition across both the workpieces 4310, 4315 was smooth, although the junction 4350 received the most new material. FIG. 43B magnifies the junction 4350. The regions 4351, 4352 adjacent to the juncture 4350 show ripples from convection in the electrolyte during deposition.

Figure 43C:
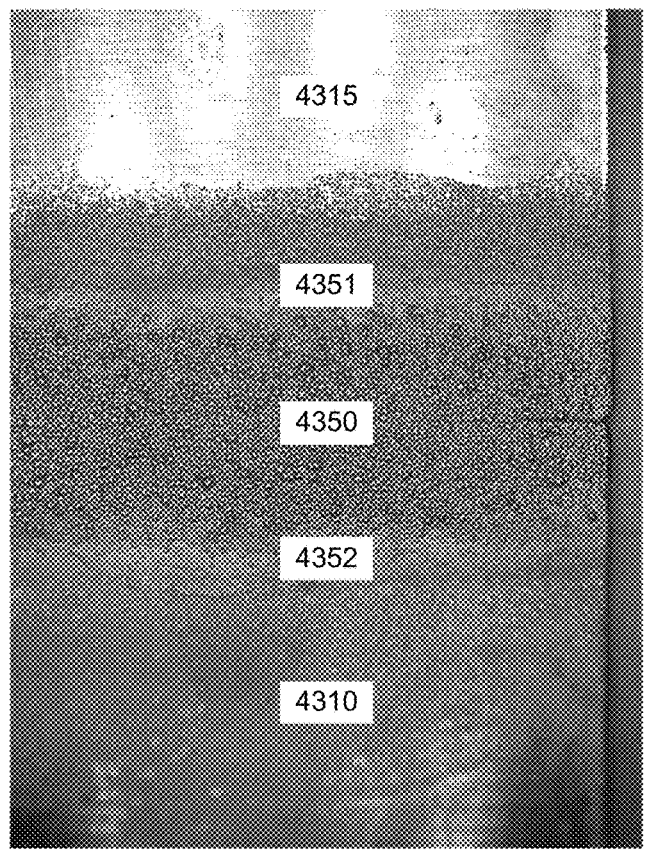
FIG. 43C is a photograph showing the workpiece after an additional round of deposition at the joint.

FIG. 43C shows the junction 4350 between the aluminum 4215 and the brass workpiece 4310 after an additional hour of electrodeposition at 1.21+/−0.02 mA/mm$^2$. The transverse current was applied via a single channel at 1.5 Vpp/50 mApp and 100 Hz with a forward ramp waveform. This waveform more strongly influenced the diffusion of charged species in electrolyte than expected. Power shifted to the electrodeposition circuit with an increase in current density of about 3.3. The transverse current dropped to about 18 mW$_{PEAK}$. This combination of electrodeposition and transverse currents increased the roughness of the deposit at the junction 4350 and in the regions 4351, 4352 near the junction.

C. Joining Copper Sheets

This example shows copper workpieces joined with copper under differing conditions using the disclosed bonding method. Copper sheets (5"×2") were cut in half, deposited with material, and then bent along their junction to test mechanical strength. Perpendicular shearing & Bending along both axis of the junction.

Figure 44C:
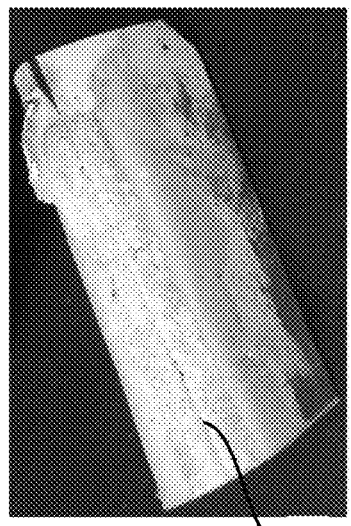
FIGS. 44A-E show copper workpieces joined with copper under differing conditions using the disclosed method.
Figure 44E:
Figure 44B:
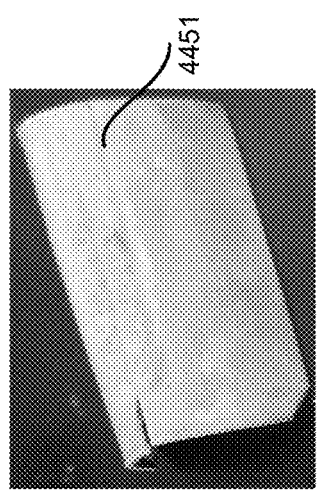
Figure 44A:
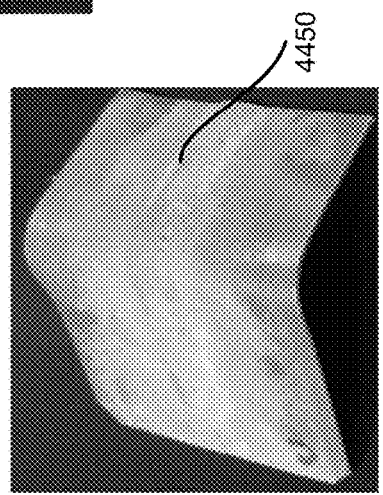

FIGS. 44A & 44B show copper sheets joined with the transverse current perpendicular to the junction. The samples were prepared with anodes on both sides of the workpieces. The bonding currents were 0.60+/−0.02 mA/mm$^2$ and 0.15+/−0.02 mA/mm$^2$. The transverse current applied through a single channel configured at the middle of the workpieces about 0.75 inches from the junction. The transverse current had a sine waveform at 20 Vpp/800 milliamperes peak-to-peak (mApp) and 100 Hz. The process ran for 15 hours. These samples were mechanically strong and had a slightly dull finish.

Figure 44D:
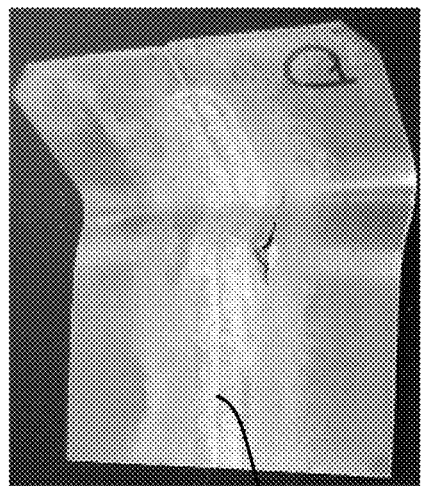

FIGS. 44C & 44D show copper sheets joined under conditions which produced a shiny finish, but displayed greater bending fatigue. Anodes were placed on both sides of the workpieces. The bonding current was 0.60+/−0.02 mA/mm$^2$ and 0.15+/−0.02 mA/mm$^2$. The transverse current was applied through a single channel with a sinusoidal waveform, 10 Vpp/66 microamperes peak-to-peak (μApp) with a 5-V DC offset, a frequency of 100 Hz, for 15 hours.

FIG. 44E shows a sample with good strength and a rough finish. The electrodeposition current was 0.60+/−0.02 mA/mm$^2$. The transverse current was applied through a single channel with a sinusoidal waveform at 10 Vpp/66 μApp with a 5 V DC offset, a frequency of 100 Hz, for 15 hours.

D. Joining Steel to Steel Via Fe—Sn Alloy

In a further example, two pieces of mild steel (5"×1"×0.032") are joined with Fe—Sn from a corroding particle anode. The transverse current is applied through a single channel is applied at 10 MHz for 8 hours using a Teflon™ applicator.

Example 16— Joining Aluminum Workpieces with Nickel Gel Electrolyte

This example explores the effects of the frequency of transverse current on electron density during the bonding process.

Two pieces of aluminum, each 1"×5"×0.032", are joined using a nickel sulfate (NiSO$_4$) gel electrolyte. The edges of the aluminum workpiece are zincated before deposition to promote nickel adhesion despite the native aluminum oxide layer. A Teflon™ applicator holds the electrolyte over the junction between the workpieces and delivers the transverse current to frequencies up to 10 GHz with losses less than 15 dbm. The applicator includes nickel anodes and two electrical contact points with the workpieces, one on each workpiece less than 1 cm on either side of the junction between the workpieces. The phase-matched transverse current is applied at the midpoint of the length of each workpiece at 1.42 Vpp. The transverse current is cycled on for 0.1 s and off for 0.5 s, enough to affect a strong joining without generating a an unwanted, continuous radio frequency.

The viscous electrolyte allows deposition nickel outside a conventional bath and propagates the transverse current at lower conductivity with less attenuation than water. The propagation speed of the transverse current is calculated to be 6×10$^9$ cm/sec, based fast impedance measurements of the effective permittivity for the electrolyte (about 25).

Figure 45:
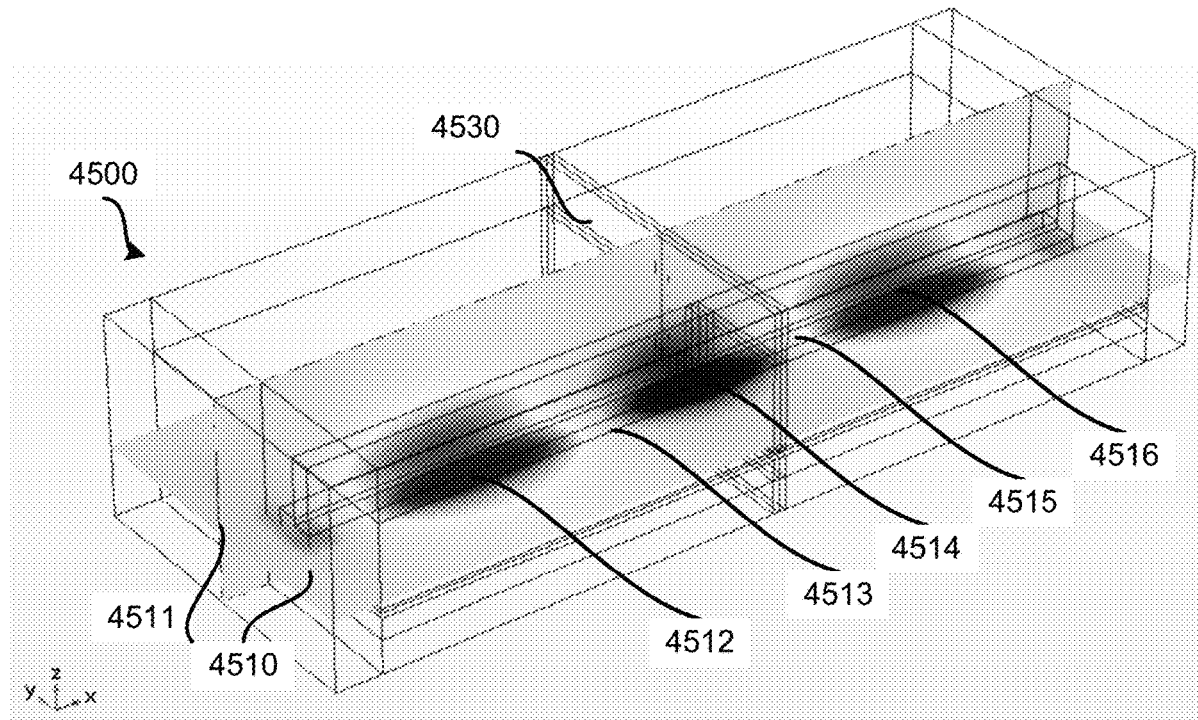
FIG. 45 depicts the calculated electric energy distribution (V/m) across a workpiece under 1-GHz transverse current, where red and blue areas show electric field strength at opposite polarities.

FIG. 45 shows the electric field strength at an instant in time for a device 4500 containing the aluminum workpieces 4510, 4511 at an applicator 4530, which defines the "origin." The energy distribution of a 1-GHz transverse current produces a standing wave with nodes 4513, 4515 and anti-nodes 4512, 4514, 4516. With no DC offset to the electrodeposition or the transverse currents, electrodeposition occurs at the red areas 4512, 4516; Corrosion occurs at the blue area 4514, which has the opposite polarity of the red areas 4512, 4516. With a DC offset less than or equal to the Vpp of the transverse current, the Vpp remains unchanged.

Figure 46:
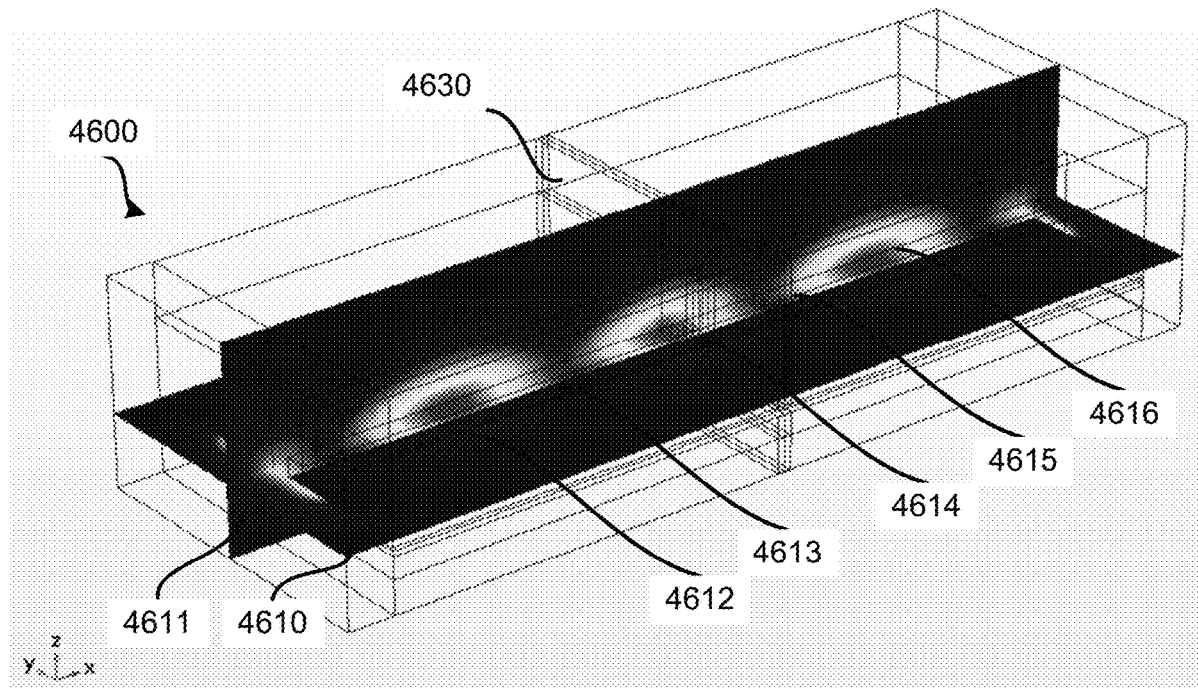
FIG. 46 depicts the calculated electric energy density time average ($J/m^3$) across a workpiece under 1-GHz transverse current, where red is the densest and dark blue is the least dense.

FIG. 46 shows the time-averaged energy density for a 1-GHz transverse current in a device 4600 containing the aluminum workpieces 4610, 4611 at an applicator 4630, which defines the "origin." The standing wave has nodes 4613, 4615 and antinodes 4612, 4614, 4616. When the Vpp of the transverse current is greater than the voltage of the DC offset, more deposition or corrosion occurs at nodes 4613, 4615 than at the anti-nodes 4612, 4614, 4616.

Figure 47:
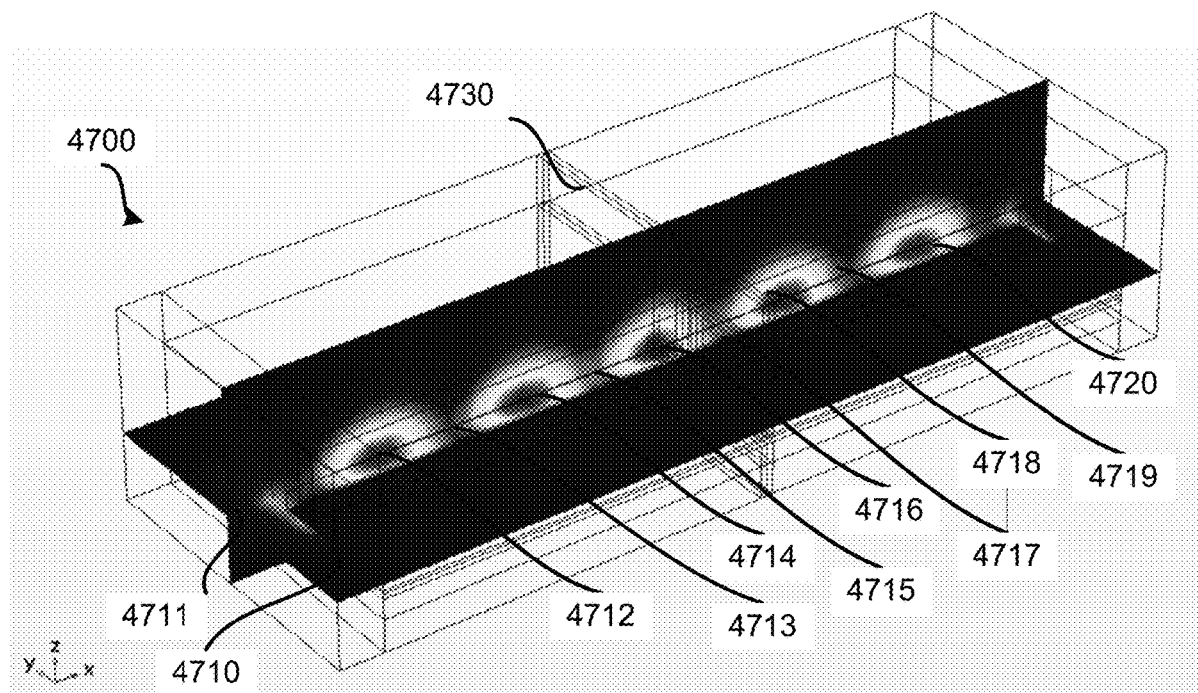
FIG. 47 depicts the calculated electric energy density time average ($J/m^3$) across a workpiece under 1.35-GHz transverse current, where red is the densest and dark blue is the least dense.

Referring to FIG. 47, a transverse current is applied at a frequency of 1.35 GHz in a device 4700, to workpieces 4710, 4711 at an applicator 4730, which defines the "origin." The standing wave produces nodes 4713, 4715, 4717, 4719 and anti-nodes 4712, 4714, 4716, 4718, 4720.

Figure 48:
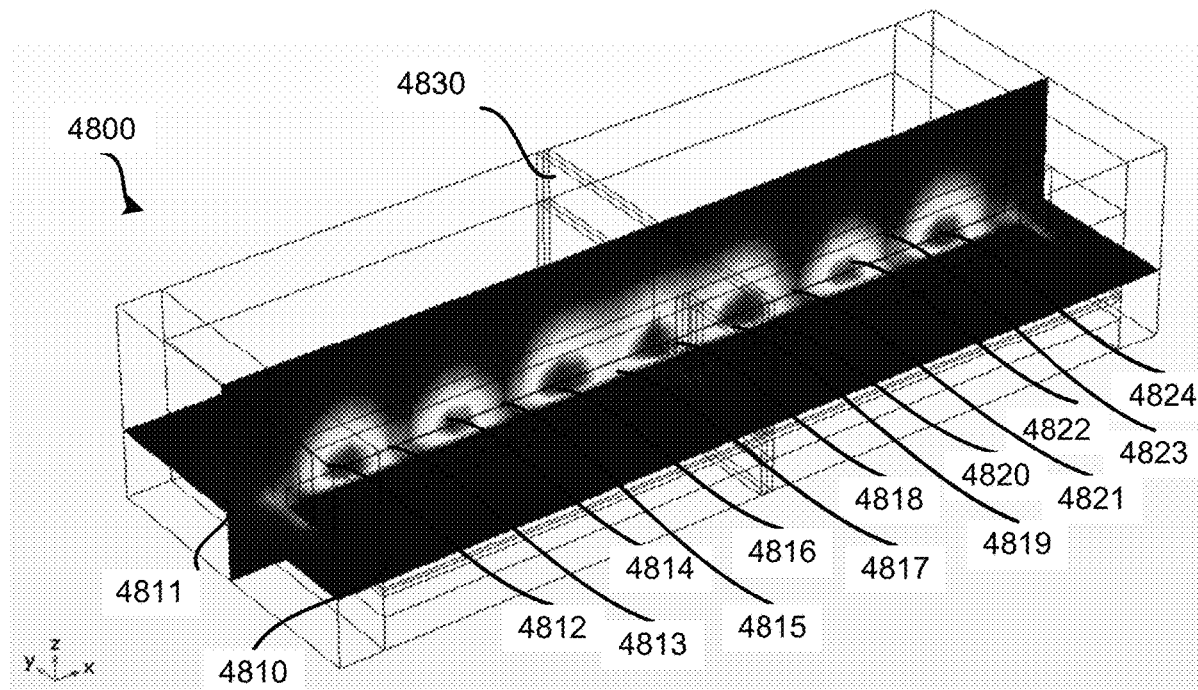
FIG. 48 depicts the calculated electric energy density time average ($J/m^3$) across a workpiece under 1.6-GHz transverse current, where red is the densest and dark blue is the least dense.

Referring to FIG. 48, a transverse current is applied at a frequency of 1.6 GHz in a device 4800, to workpieces 4810, 4811 at an applicator 4530, which defines the "origin." The standing wave produces nodes 4813, 4815, 4817, 4819, 4821, 4823 and anti-nodes 4812, 4814, 4816, 4818, 4820, 4822, 4824.

Figure 49:
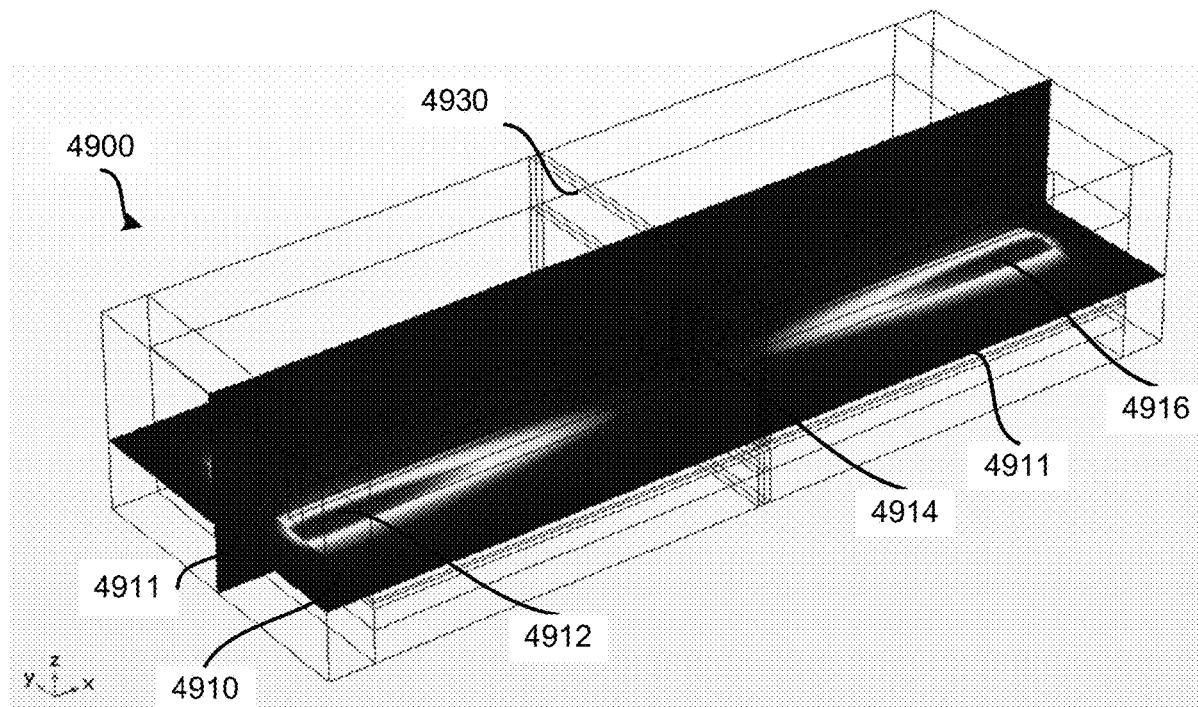
FIG. 49 depicts the calculated electric energy density time average ($J/m^3$) across a workpiece under 220-MHz transverse current, where red is the densest and dark blue is the least dense.

Referring to FIG. 49, a transverse current is applied at a frequency of 220 MHz in a device 4900, to workpieces 4910, 4911 abutting at an applicator 4530, which defines the "origin." The ratio of the transverse current wave and the junction length causes the workpieces at the origin 4914 to behave like an electrical short with low impedance. The ends of the workpiece 4912, 4916 terminate and behave like an open circuit, causing energy buildup. The length of the junction corresponds to half the transverse current wavelength, and the second frequency corresponds to one full period of the transverse current wavelength.

Figure 50:
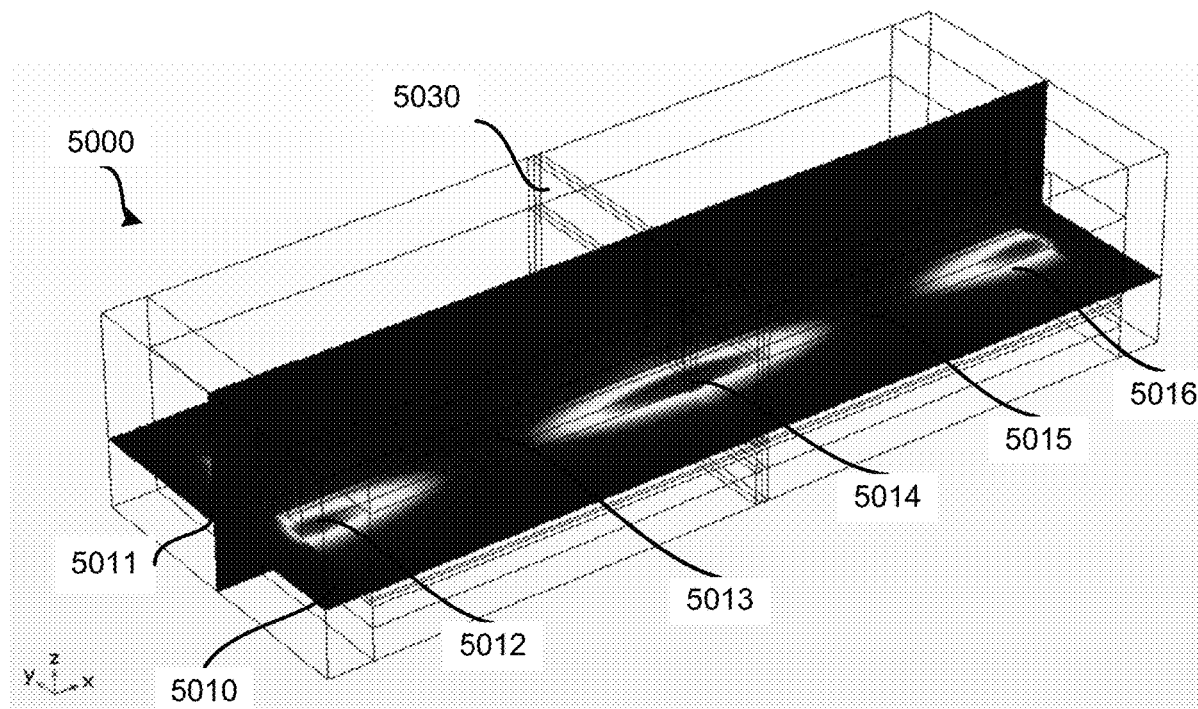
FIG. 50 depicts the calculated electric energy density time average ($J/m^3$) across a workpiece under 480-MHz transverse current, where red is the densest and dark blue is the least dense.

Referring to FIG. 50, a transverse current is applied at a frequency of 480 MHz in a device 5000, to workpieces 5010, 5011 at an applicator 4530, which defines the "origin." The workpieces 5010, 5011 at the origin 5014 experience a large increase in impedance, with localized energy buildup. The high energy density at the edges 5012, 5016 is weaker at 1 λ.

Comparatively, the anti-node distribution for the 1.33-GHz transverse current is preferred for deposition (FIG. 47). The 1-GHz is too broad and intense (FIG. 45) and the energy distribution of 1.6-GHz transverse current is too uneven (FIG. 48). Above 1-GHz, the periodic transverse current artificially changes the rate of deposition points along the junction, increasing the parallel electric field strength and preventing high current density areas. At frequencies of 1, 1.33 or 1.6 GHz, the transverse current origin corresponds to an anti-node 100% of the time. There, the transverse current signal may be turned so the workpiece surface at the origin is does not experience an anti-node. The higher frequency transverse current may cause stronger bonds between the two workpieces because energy is better distributed, while the lower frequencies could cause a redistribute metal.

In laboratory samples, anti-nodes on either side of the junction are not be identical. Differences in the phase on the electrodes arise from these asymmetries. These differences change as new metal is deposited. Cycling the transverse current helps avoid forming artificial rough spots.

Shifting the transverse current through several frequencies changes the standing wave, so that nodes and antinodes fall on different positions of the workpieces. The corrosion and deposition processes are then distributed over the surface of the workpiece. A smooth finish is achieved on a deposit, particularly for high frequencies and without electrodeposition signal modulation.

Example 17—Battery Healing

This example explores battery healing using the disclosed method. Li-metal coin cells are constructed inside a glove box under an anhydrous and oxygen-free inert argon atmosphere. The anode comprises Li-foil and the electrolyte is a 1:1 mixture of ethylene carbonate and dimethyl carbonate with dissolved LiPF$_6$ at a concentration between 0.2 M and 1.0 M. The coin cells are loaded into a charge-discharge cell to deliver impedance-regulated AC energy from a battery control unit to the coin cell. During both charge and discharge cycles (deposition and dissolution), the transverse current signal is applied over the standard charge/discharge potentials. Both processes involve Li diffusion through the solid electrolyte interphase. Electrical contact is made between the charge-discharge cell and the coin cell.

In one instance, a centered 1-mm pin contacts the anode surface. The pin is centered inside a 1-mm thick conductive ring with a radius equal to the coin cell's anode surface. Filling the space between the pin and the coin cell is a polytetrafluoroethylene (PTFE) disk. The three components are brought into direct contact with the anode face of the coin cell inside the charge-discharge cell. The transverse current signal originates at the pin. The ring may be connected to ground or to a second transverse current channel. The dielectric PTFE facilitates uniform propagation of AC signal.

In another instance, both the pin and ring are separate transverse current channels, providing a transverse current of 2.4 GHz at a 180° phase offset. At the pin originates a −12 dbm sinusoidal wave and along the ring originates a −8 dbm sinusoidal wave. Over two minutes, the powers at each channel are reversed, shifting the interference patterns moves that sweeps the current density over the surface and encourages lateral movement of ions through the solid electrolyte interphase. This sweeping discourages fixed ion channels from forming.

In still another instance, the transverse current channel at the pin uses no repeating waveform. Instead a continuously variable waveform is emitted that accounts for the constant constructive and destructive interference between incident energy from the pin and reflected energy from the outer edges of the anode. At areas of constructive interference, the localized potential exceeds the thermodynamic boundary for Li deposition or dissolution. Areas of destructive interference do not exceed this boundary, so deposition or dissolution lessens. As the transverse current signal changes, the locations of these constructive and destructive points change at a controlled rate similar to the ionic mobility of lithium ions.

With the pin contact, transverse current (incident AC energy) from the charge-discharge cell is distributed radially and uniformly from the center to the outer edge of the Li-foil. When the wavelength of the incident energy is long compared to the radius of the anode, the AC potential is roughly the same across the entire surface. When the wavelengths are similar to dimensions of the anode, reflections affect the energy density and surface potential changes.

During the charging process, when Li-ions migrate from the electrolyte through the solid electrolyte interphase and deposit onto the Li anode, the electromagnetic field is increased parallel to the foil surface. This increase aids lateral movement of Li+ ions in the solid electrolyte interphase. The uniformity of the solid electrolyte interphase may be better maintained to achieve stability over increased number of charge/discharge cycles.

Having described several embodiments, it will be recognized by those skilled in the art that various modifications, alternative constructions, and equivalents may be used without departing from the spirit of the disclosure. And several well-known processes and elements have not been described to avoid unnecessarily obscuring the embodiments disclosed. So the above description should not be taken as limiting the document.

Those skilled in the art will appreciate that the disclosed embodiments teach for example and not by limitation. Therefore, the matter in the above description or shown in the drawings should be interpreted as illustrative and not in a limiting sense. These claims should cover all generic and specific features described, and all statements of the present method and system, which, as a matter of language, might be said to fall therebetween.

Exemplary Embodiments

The following is a listing of exemplary embodiments for methods and apparatuses disclosed herein:

1. A method comprising:
inducing a first current between a source of a countercharge and a first electrode, the first current being through an electrolyte;
inducing a second current across the first electrode, the second current being transverse to the first current, and the second current inducing a relativistic charge across the first electrode.
2. The method of claim 1, wherein the first electrode is a working electrode.
3. The method of claims 1-2, the electrolyte comprising a metal, the first electrode having a void with a metal edge, the relativistic charge causing a metal-metal bond to form between metal from the electrolyte and the metal edge to thereby fill the void.
4. The method of claim 3, wherein the void is a crack, crevice, or fracture in the first electrode.
5. The method of claim 3, the void forming a gap between a first portion of the first electrode, the first portion having a first edge of the metal edge, and a second portion of the first electrode, the second portion with a second edge of the metal edge proximate the first edge, the relativistic charge causing the metal-metal bond to form between metal from the first edge and metal from the electrolyte and between metal from the second edge and metal from the electrolyte, the bonded metals thereby bridging the gap to form a unified electrode of the first portion and the second portion.
6. The method of claims 1-5, wherein the source of a counter charge is an electrode counter to the first electrode.
7. The method of claims 1-6, wherein the electrolyte comprises a metal and one or more species selected from the group consisting of water, ammonium salts, metal chlorides, metal sulfates, ionic liquids, ionogels, and any combination thereof.
8. The method of claim 7, wherein the electrolyte comprises an ionic liquid, and the ionic liquid is a room temperature ionic liquid.
9. The method of claim 8, wherein the room-temperature ionic liquid is 1-ethyl-3-methylimidazolium chloride.
10. The method of claims 1-9, wherein the electrolyte comprises metal particles.
11. The method of claims 1-10, wherein the second current is chosen from an alternating current (AC) second current, or a combination of an AC second current and a direct current (DC) second current.
12. The method of claim 11, wherein the second current is the combination of the AC second current and the DC second current, the DC second current offsetting the AC second current by an amount less than an electrochemical breakdown of the electrolyte.
13. The method of claims 1-12, the second current having a waveform comprising a plurality of waveforms based on harmonics of one or more frequencies at which the electrolyte or the first electrode exhibits absorption of the one or more frequencies.
14. The method of claim 13, the second current having a phase offset of about 90° between an onset frequency voltage and an output amperage.
15. The method of claims 1-14, further comprising applying a signal cancellation to reduce a far-field radiation from the first electrode.
16. The method of claims 1-15, the second current having a period similar to a diffusion rate of a component in the electrolyte.
17. A method comprising:
inducing an electric field between a source of a countercharge and a first electrode, the electric field having field lines through an electrolyte;
inducing a potential across a surface of the first electrode, the induced potential bending the field lines proximate the surface such that metal from the electrolyte follows a path of the bent field lines to deposit the metal onto the surface.
18. The method of claim 17, wherein the first electrode is a working electrode.
19. The method of claims 17-19, the first electrode having a void with a metal edge, the induced potential causing a metal-metal bond to form between metal from the electrolyte and the metal edge to thereby fill the void.
20. The method of claim 19, wherein the void is a crack, crevice, or fracture in the first electrode.
21. The method of claim 19, the void forming a gap between a first portion of the first electrode, the first portion having a first edge of the metal edge, and a second portion of the first electrode, the second portion with a second edge of the metal edge proximate to the first edge, the relativistic charge causing the metal-metal bond between metal from the first edge and metal from the electrolyte and between metal from the second edge and metal from the electrolyte, the bonded metals to thereby bridging the gap to form a unified electrode of the first portion and the second portion.
22. The method of claims 17-21, wherein the source of a counter charge is an electrode counter to the first electrode.
23. The method of claims 17-22, wherein the electrolyte comprising one or more species selected from the group consisting of water, quaternary ammonium salts, metal chlorides, ionic liquids, ionogels, and any combination thereof.
24. The method of claim 23, wherein the electrolyte comprises an ionic liquid, and the ionic liquid is a room temperature ionic liquid.
25. The method of claim 24, wherein the room-temperature ionic liquid is 1-ethyl-3-methylimidazolium chloride.

26. The method of claims 17-25, wherein the electrolyte comprises metal particles.

27. The method of claims 17-26, wherein the second current is chosen from an alternating current (AC) second current, or a combination of an AC second current and a direct current (DC) second current.

28. The method of claims 17-27, the induced potential having a waveform comprising a plurality of waveforms based on harmonics of one or more frequencies at which the electrolyte or the first electrode exhibits absorption at the one or more frequencies.

29. The method of claim 28, the induced potential having a phase offset of about 90° between an onset frequency and an output amperage.

30. The method of claims 17-29, further comprising applying a signal cancellation to reduce a far-field radiation from the first electrode.

31. The method of claims 17-30, the induced potential having a period similar to a diffusion rate of a component in the electrolyte.

32. A method comprising: inducing a potential across a surface of an electrode in the presence of a chemical potential between an electrolyte and the surface of the electrode, the induced potential relativistically charging the surface of the electrode.

33. The method of claim 32, the relativistic charge causing a metal-metal bond to form between metal from the electrolyte and metal on the surface.

34. The method of claim 33, the electrode having a void with a metal edge, the relativistic charge causing the metal-metal bond between metal from the electrolyte and the metal edge to thereby fill the void.

35. The method of claim 34, the void forming a gap between a first portion of the electrode, the first portion having a first edge of the metal edge, and a second portion of the electrode, the second portion with a second edge of the metal edge proximate to the first edge, the relativistic charge causing the metal-metal bond to form between metal from the first edge and metal from the electrolyte and between metal from the second edge and metal from the electrolyte, the bonded metals to thereby bridging the gap to form a unified electrode of the first portion and the second portion.

36. The method of claims 32-35, wherein the electrolyte comprises metal and one or more species selected from the group consisting of water, quaternary ammonium salts, metal chlorides, ionic liquids, ionogels, and any combination thereof.

37. The method of claims 32-36, wherein the electrolyte comprises metal particles.

38. The method of claims 32-37, wherein the induced potential is chosen from an alternating current (AC) induced potential, or a combination of an AC induced potential and a direct current (DC) induced potential.

39. The method of claim 38, wherein the induced potential is the combination of the AC induced potential and the DC induced potential, the DC induced potential offsetting the AC induced potential by an amount less than an electrochemical breakdown of the electrolyte.

40. The method of claims 32-39, the induced potential having a waveform comprising a plurality of waveforms based on harmonics of one or more frequencies at which the electrolyte or the electrode exhibits absorption at the one or more frequencies.

41. The method of claim 40, wherein the induced potential comprises a phase offset of about 90° between an onset frequency and an output amperage.

42. The method of claims 32-41, further comprising applying a signal cancellation to reduce a far-field radiation from the electrode.

43. The method of claims 32-42, the induced potential having a period similar to a diffusion rate of a component in the electrolyte.

44. The method of claims 1-43, wherein the first electrode comprises at least two galvanically reactive metals meeting a junction, the second current reducing corrosion at the junction.

45. The method of claim 44, wherein the second current distributes charge away from grain boundaries on the surface of the first electrode and avoids corrosive pitting at the surface of the first electrode.

46. The method of claims 1-43, wherein the first current has a positive potential sufficient to corrode away a rough feature at the surface of the first electrode.

47. The method of claim 46, wherein the first current is applied with a low current density, a pulsed current density, or a combination of a low, pulsed current density.

48. The method of claims 1-31, wherein metal from the electrolyte bonds to a vacant site on the surface of the first electrode or the source for a countercharge and not to a previously bonded metal.

49. The method of claim 48, wherein a membrane is disposed between the source for a countercharge and the first electrode, the source for a countercharge comprising $LiM_xO_y$, the first electrode comprising carbon or $Li^0$, the metal from the electrolyte comprising Li+, and the previously-bonded metal comprising $Li^0$.

50. A corroding electrode comprising one or more metal species selected from the group consisting of metal particles, metal ions, and combinations thereof;
wherein the corroding electrode dissolves when a first current is applied between the corroding electrode and a first electrode through an electrolyte, thereby suspending the one or more metal species into the electrolyte.

51. The corroding electrode of claim 50, further comprising one or more ceramic particles or dielectric polymers.

52. The corroding electrode of claims 50-51, wherein the corroding source of a countercharge is formed by being pressed together into a solid body.

53. The corroding electrode of claims 50-52, wherein the metal particles have grain sizes selected to grain sizes of the first electrode.

54. The corroding electrode of claims 50-53, comprising metal particles having rough or non-symmetric dimensions.

55. The corroding electrode of claims 50-54, comprising metal particles having spherical dimensions and a uniform surface energy.

56. The corroding electrode of claims 50-55, comprising metal particles having an elongated dimension, which aligns with a second current induced across the first electrode, the second current being transverse to the first current, and the second current inducing a relativistic charge across the first electrode.

57. The method of claims 1-31, wherein the source of a countercharge is a corroding electrode of claims 50-56.

58. A device comprising:
a source of a countercharge, and
a first electrode in electrical communication through an electrolyte with the source of a countercharge;
wherein a first current is induced through the electrolyte between the source of a countercharge and the first electrode; and wherein a second current is induced across the first electrode, the second current being transverse to the first current, and the second current inducing a relativistic charge across the first electrode.

59. The device of claim 58, wherein the first electrode is a working electrode.

60. The device of claims 58-59, the electrolyte comprising a metal, the first electrode having a void with a metal edge, the relativistic charge causing a metal-metal bond to form between metal from the electrolyte and the metal edge to thereby fill the void.

61. The device of claim 60, wherein the void is a crack, crevice, or fracture in the first electrode.

62. The device of claim 60, the void forming a gap between a first portion of the first electrode, the first portion having a first edge of the metal edge, and a second portion of the first electrode, the second portion with a second edge of the metal edge proximate the first edge, the relativistic charge causing the metal-metal bond to form between metal from the first edge and metal from the electrolyte and between metal from the second edge and metal from the electrolyte, the bonded metals thereby bridging the gap to form a unified electrode of the first portion and the second portion.

63. The device of claims 58-62, wherein the source of a countercharge is an electrode counter to the first electrode.

64. The device of claims 58-63, wherein the electrolyte comprises a metal and one or more species selected from the group consisting of water, quaternary ammonium salts, metal chlorides, ionic liquids, ionogels, and any combination thereof.

65. The device of claim 64, wherein the electrolyte comprises an ionic liquid, and the ionic liquid is a room temperature ionic liquid.

66. The device of claim 65, wherein the room-temperature ionic liquid is 1-ethyl-3-methylimidazolium chloride.

67. The device of claims 58-66, wherein the electrolyte comprises metal particles.

68. The device of claims 58-67, wherein the second current is chosen from an alternating current (AC) second current, or a combination of an AC second current and a direct current (DC) second current.

69. The device of claim 68, wherein the second current is the combination of the AC second current and the DC second current, the DC second current offsetting the AC second current by an amount less than an electrochemical breakdown of the electrolyte.

70. The device of claims 58-69, further comprising a waveform generator to provide the second current with a waveform comprising a plurality of waveforms based on harmonics of one or more frequencies at which the electrolyte or the first electrode exhibits absorption of the one or more frequencies.

71. The device of claims 58-70, further comprising a signal canceler to reduce a far-field radiation from the first electrode.

72. The device of claims 58-71, the second current having a period similar to a diffusion rate of a component in the electrolyte.

73. A device comprising:
a source of a countercharge, and
a first electrode in electrical communication through an electrolyte with the source of a countercharge;
wherein an electric field is induced between the source of a countercharge and the first electrode, the electric field having field lines through the electrolyte; and
wherein a potential is induced across a surface of the first electrode, the induced potential bending the field lines proximate the surface such that metal from the electrolyte follows a path of the bent field lines to deposit the metal onto the surface.

74. The device of claim 73, wherein the first electrode is a working electrode.

75. The device of claims 73-75, the first electrode having a void with a metal edge, the induced potential causing a metal-metal bond to form between metal from the electrolyte and the metal edge to thereby fill the void.

76. The device of claim 75, wherein the void is a crack, crevice, or fracture in the first electrode.

77. The device of claim 75, the void forming a gap between a first portion of the first electrode, the first portion having a first edge of the metal edge, and a second portion of the first electrode, the second portion with a second edge of the metal edge proximate to the first edge, the relativistic charge causing the metal-metal bond between metal from the first edge and metal from the electrolyte and between metal from the second edge and metal from the electrolyte, the bonded metals to thereby bridging the gap to form a unified electrode of the first portion and the second portion.

78. The device of claims 73-77, wherein the source of a countercharge is an electrode counter to the first electrode.

79. The device of claims 73-78, wherein the electrolyte comprises one or more species selected from the group consisting of water, quaternary ammonium salts, metal chlorides, ionic liquids, ionogels, and any combination thereof.

80. The device of claim 79, wherein the electrolyte comprises an ionic liquid, and the ionic liquid is a room temperature ionic liquid.

81. The device of claim 80, wherein the room-temperature ionic liquid is 1-ethyl-3-methylimidazolium chloride.

82. The device of claims 73-81, wherein the electrolyte comprises metal particles.

83. The device of claims 73-82, wherein the second current is chosen from an alternating current (AC) second current, or a combination of an AC second current and a direct current (DC) second current.

84. The device of claims 73-83, further comprising a waveform generator to provide the induced potential with a waveform comprising a plurality of waveforms based on harmonics of one or more frequencies at which the electrolyte or the first electrode exhibits absorption at the one or more frequencies.

85. The device of claims 73-84, further comprising a signal canceler to reduce a far-field radiation from the first electrode.

86. The device of claims 73-85, the induced potential having a period similar to a diffusion rate of a component in the electrolyte.

87. A first electrode, wherein a potential is induced across a surface of the first electrode in the presence of a chemical potential between an electrolyte and the surface of the first electrode, the induced potential relativistically charging the surface of the first electrode.

88. The first electrode of claim 87, the relativistic charge causing a metal-metal bond to form between metal from the electrolyte and metal on the surface.

89. The first electrode of claim 88, the first electrode having a void with a metal edge, the relativistic charge causing the metal-metal bond between metal from the first electrolyte and the metal edge to thereby fill the void.

90. The first electrode of claim 89, the void forming a gap between a first portion of the first electrode, the first portion having a first edge of the metal edge, and a second portion of the first electrode, the second portion with a second edge of the metal edge proximate to the first edge, the relativistic charge causing the metal-metal bond to form between metal from the first edge and metal from the electrolyte and between metal from the second edge and metal from the electrolyte, the bonded metals to thereby bridging the gap to form a unified electrode of the first portion and the second portion.

91. The first electrode of claims 87-90, wherein the electrolyte comprises metal and one or more species selected from the group consisting of water, quaternary ammonium salts, metal chlorides, ionic liquids, ionogels, and any combination thereof.

92. The first electrode of claims 87-91, wherein the electrolyte comprises metal particles.

93. The first electrode of claims 87-92, wherein the induced potential is chosen from an alternating current (AC) induced potential, or a combination of an AC induced potential and a direct current (DC) induced potential.

94. The first electrode of claim 93, wherein the induced potential is the combination of the AC induced potential and the DC induced potential, the DC induced potential offsetting the AC induced potential by an amount less than an electrochemical breakdown of the electrolyte.

95. The first electrode of claims 87-94, the induced potential having a waveform comprising a plurality of waveforms based on harmonics of one or more frequencies at which the electrolyte or the electrode exhibits absorption at the one or more frequencies.

96. The first electrode of claims 87-95, the induced potential having a period similar to a diffusion rate of a component in the electrolyte.

97. A device comprising:
a main control unit comprising a power supply and a power modulator;
an electrode applicator unit, comprising at least one source of a countercharge and a plurality of channels for flowing an electrolyte through the electrode applicator unit, the electrode applicator unit being connected to the main control unit;
a current collector cable connected to the main control unit; and
a power control unit connected to the main control unit, which power control unit applies a first current between a first electrode and the at least one source of a countercharge through the electrolyte, the power control unit inducing a second current across the first electrode, the second current being transverse to the first current, and the second current inducing a relativistic charge across the first electrode.

98. The device of claim 97, wherein the main control unit further comprises a computer for executing instructions stored on a computer readable medium.

99. The device of claim 98, wherein the power modulator and the power control unit are controlled by the computer.

100. The device of claims 97-99, wherein the main control unit further comprises an electrolyte storage tank, at least one pump, and tubing connected to the electrolyte storage tank, the at least one pump, and the electrode applicator unit; thereby flowing the electrolyte from the electrolyte storage tank through the tubing into the plurality of channels of the electrode applicator unit.

101. The device of claims 97-100, wherein the electrode applicator unit further comprises a heating unit or a cooling unit for modulating a temperature of the electrolyte within the channels of the electrode applicator unit.

102. The device of claims 97-101, wherein the current collector cable further comprises leads for attaching to the first electrode.

103. The device of claim 56-86 or 97-102, wherein the at least one source of a countercharge comprises a corroding electrode of claims 50-56.

104. The device of claim 56-86 or 97-102, wherein the device performs a method of claims 1-49.

What is claimed is:

1. An apparatus comprising:
a waveform generator electrically connected to an electrochemical cell, the waveform generator inducing an alternating current electric waveform on an anode of the electrochemical cell in the presence of a charge or a discharge potential in the electrochemical cell, the alternating current waveform distributing charge current or discharge current transverse to an interface between the anode and an electrolyte of the electrochemical cell.

2. The apparatus of claim 1 wherein the alternating current waveform is a sinusoidal variable frequency waveform.

3. The apparatus of claim 1 wherein the waveform generator further induces a second alternating current waveform on the anode at a second location different from a first location where the first alternating current waveform is applied.

4. The apparatus of claim 3 wherein the second alternating current waveform is offset 180 degrees in phase from the first alternating current waveform.

5. The apparatus of claim 3 wherein the second alternating current waveform is at a different power from the first alternating current waveform.

6. The apparatus of claim 5 wherein the waveform generator further:
inducing the first alternating current waveform at a first power;
inducing the second alternating current waveform at a second power different from the first power; and
subsequently inducing the first alternating current waveform at the second power and the second alternating current waveform at the first power.

7. The apparatus of claim 3 wherein the first location is a center of the anode and the second location is a ring of the anode.

8. The apparatus of claim 1 wherein the waveform generator induces the alternating current waveform on a center area of a circularly shaped anode.

9. The apparatus of claim 1 wherein the alternating current waveform is a variable frequency waveform.

10. The apparatus of claim 1 wherein the alternating current waveform is a continuously variable frequency waveform.

11. The apparatus of claim 1 wherein the charge or discharge current distribution across the interface reduces development of non-uniformities in a solid electrolyte interphase between the anode and the electrolyte.

12. The apparatus of claim 1 wherein the charge or discharge current distribution across the interface discourages channels from developing in the solid electrolyte interphase associated with dendrite growth.

13. The apparatus of claim 1 wherein the electrochemical cell is a part of a Lithium-Ion battery.

* * * * *